(12) United States Patent
Long et al.

(10) Patent No.: US 8,951,972 B2
(45) Date of Patent: *Feb. 10, 2015

(54) FGFR1 EXTRACELLULAR DOMAIN COMBINATION THERAPIES FOR LUNG CANCER

(75) Inventors: Li Long, Lafayette, CA (US); Thomas Brennan, San Jose, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 13/296,168

(22) Filed: Nov. 14, 2011

(65) Prior Publication Data

US 2012/0237511 A1 Sep. 20, 2012

Related U.S. Application Data

(60) Provisional application No. 61/421,462, filed on Dec. 9, 2010.

(51) Int. Cl.

| | |
|---|---|
| A61K 38/00 | (2006.01) |
| A61K 39/00 | (2006.01) |
| A61P 35/00 | (2006.01) |
| C07K 16/00 | (2006.01) |
| C12P 21/00 | (2006.01) |
| A61K 38/17 | (2006.01) |
| A61K 39/395 | (2006.01) |
| A61K 45/06 | (2006.01) |
| A61K 38/38 | (2006.01) |
| A61K 31/337 | (2006.01) |
| A61K 31/4745 | (2006.01) |
| A61K 31/475 | (2006.01) |
| A61K 31/513 | (2006.01) |
| A61K 31/519 | (2006.01) |
| A61K 31/555 | (2006.01) |
| A61K 31/704 | (2006.01) |
| A61K 31/7048 | (2006.01) |
| A61K 33/24 | (2006.01) |

(52) U.S. Cl.
CPC ........... *A61K 38/179* (2013.01); *A61K 39/3955* (2013.01); *A61K 45/06* (2013.01); *A61K 38/38* (2013.01); *A61K 31/337* (2013.01); *A61K 31/4745* (2013.01); *A61K 31/475* (2013.01); *A61K 31/513* (2013.01); *A61K 31/519* (2013.01); *A61K 31/555* (2013.01); *A61K 31/704* (2013.01); *A61K 31/7048* (2013.01); *A61K 33/24* (2013.01)
USPC ................... 514/19.3; 424/134.1; 424/185.1; 424/192.1; 514/1.1; 530/388.8; 435/69.7

(58) Field of Classification Search
CPC ................................................ A61K 2300/00
See application file for complete search history.

(56) References Cited

U.S. PATENT DOCUMENTS

| | | | |
|---|---|---|---|
| 5,229,501 A | 7/1993 | Keifer et al. | |
| 5,288,855 A | 2/1994 | Bergonzoni et al. | |
| 5,474,914 A | 12/1995 | Spaete | |
| 5,486,462 A | 1/1996 | Rutter et al. | |
| 5,707,632 A | 1/1998 | Williams et al. | |
| 5,750,371 A | 5/1998 | Senoo et al. | |
| 5,767,250 A | 6/1998 | Spaete | |
| 5,863,888 A | 1/1999 | Dionne et al. | |
| 6,255,454 B1 | 7/2001 | Keifer et al. | |
| 6,344,546 B1 | 2/2002 | Dionne et al. | |
| 6,350,593 B1 | 2/2002 | Williams et al. | |
| 6,355,440 B1 | 3/2002 | Williams et al. | |
| 6,384,191 B1 | 5/2002 | Williams et al. | |
| 6,517,872 B1 | 2/2003 | Yayon et al. | |
| 6,656,728 B1 | 12/2003 | Kavanaugh et al. | |
| 6,844,168 B1 | 1/2005 | Keifer et al. | |
| 7,135,311 B1 | 11/2006 | David et al. | |
| 7,297,774 B2 | 11/2007 | Ullrich et al. | |
| 7,645,609 B2 | 1/2010 | Follstad | |
| 7,678,890 B2 | 3/2010 | Bosch et al. | |
| 7,947,811 B2 * | 5/2011 | Pereira et al. ............ | 530/388.22 |
| 7,982,014 B2 | 7/2011 | Williams et al. | |

(Continued)

FOREIGN PATENT DOCUMENTS

| | | |
|---|---|---|
| EP | 0 545 343 A1 | 6/1993 |
| EP | 2083081 A1 | 7/2009 |

(Continued)

OTHER PUBLICATIONS

U.S. Appl. No. 13/227,398, filed Sep. 7, 2011, Williams et al.

(Continued)

*Primary Examiner* — Elly-Gerald Stoica

(74) *Attorney, Agent, or Firm* — Casimir Jones, S.C.

(57) ABSTRACT

Methods of treating cancer comprising administering a fibroblast growth factor receptor 1 (FGFR1) extracellular domain (ECD) and/or an FGFR1 ECD fusion molecule in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, and bevacizumab are provided. Dosage packs comprising an FGFR1 ECD and/or an FGFR1 ECD fusion molecule and/or at least one additional therapeutic agent selected from docetaxel, paclitaxel, vincristine, carboplatin, cisplatin, oxaliplatin, doxorubicin, 5-fluorouracil (5-FU), leucovorin, pemetrexed, and bevacizumab are also provided. In some embodiments, a dosage pack comprises instructions for administering FGFR1 ECD and/or FGFR1 ECD fusion molecule with at least one additional therapeutic agent.

6 Claims, 26 Drawing Sheets

(56) References Cited

U.S. PATENT DOCUMENTS

| | | | |
|---|---|---|---|
| 8,119,770 | B2* | 2/2012 | Blanche et al. ............... 530/350 |
| 8,173,134 | B2 | 5/2012 | Bosch et al. |
| 8,338,569 | B2 | 12/2012 | Marshall et al. |
| 2004/0063910 | A1 | 4/2004 | Kavanaugh et al. |
| 2004/0115768 | A1 | 6/2004 | Follstad |
| 2005/0187150 | A1 | 8/2005 | Mohammadi et al. |
| 2006/0234347 | A1 | 10/2006 | Harding et al. |
| 2006/0286102 | A1 | 12/2006 | Jin et al. |
| 2007/0248604 | A1 | 10/2007 | Desnoyers et al. |
| 2007/0248605 | A1 | 10/2007 | Hestir et al. |
| 2010/0087627 | A1 | 4/2010 | Marshall et al. |
| 2010/0111873 | A1* | 5/2010 | Russell et al. ............... 424/9.2 |
| 2010/0158911 | A1 | 6/2010 | Williams et al. |
| 2011/0281302 | A1 | 11/2011 | Williams et al. |
| 2012/0128672 | A1 | 5/2012 | Keer |
| 2012/0251538 | A1 | 10/2012 | Harding et al. |
| 2012/0301921 | A1 | 11/2012 | Williams et al. |
| 2013/0136740 | A1 | 5/2013 | Harding et al. |

FOREIGN PATENT DOCUMENTS

| | | |
|---|---|---|
| EP | 1910542 B1 | 12/2009 |
| WO | WO 91/00916 | 1/1991 |
| WO | WO 91/11459 | 8/1991 |
| WO | WO 02/094852 A2 | 11/2002 |
| WO | WO 2004/110487 A1 | 12/2004 |
| WO | WO 2005/113596 A2 | 12/2005 |
| WO | WO 2005/115363 A2 | 12/2005 |
| WO | WO 2006/081430 A2 | 8/2006 |
| WO | WO 2006/113277 A2 | 10/2006 |
| WO | WO 2007/014123 A2 | 2/2007 |
| WO | WO 2007/059574 A1 | 5/2007 |
| WO | WO 2007/134210 A2 | 11/2007 |
| WO | WO 2008/065543 A2 | 6/2008 |
| WO | WO 2008/118877 A2 | 10/2008 |
| WO | WO 2011/060333 A1 | 5/2011 |
| WO | WO 2012/125812 A1 | 9/2012 |
| WO | WO 2012/177481 A2 | 12/2012 |
| WO | WO 2013/074492 A1 | 5/2013 |

OTHER PUBLICATIONS

Akimoto et al., "Fibroblast growth factor 2 promotes microvessel formation from mouse embryonic aorta" Am. J. Physiol. Cell Physiol., vol. 284, No. 2, 2003, pp. C371-C377.

Anderson et al., "Apert syndrome mutations in fibroblast growth factor receptor 2 exhibit increased affinity for FGF ligand" Human Molecular Genetics, vol. 7, No. 9, 1998, pp. 1475-1483.

Auguste et al., "Inhibition of fibroblast growth factor—fibroblast growth factor receptor activity in glioma cells impedes tumor growth by both angiogenesis-dependent and -independent mechanisms" Cancer Research, vol. 61, Feb. 15, 2001, pp. 1717-1726.

Baker et al., "Metabolic control of recombinant protein N-glycan processing in NSO and CHO cells" Biotechnology and Bioengineering, vol. 73, No. 3, May 5, 2001, pp. 188-202.

Ballinger et al., "Semirational design of a potent, artificial agonist of fibroblast growth factor receptors" Nature Biotechnology, vol. 17, Dec. 1999, pp. 1199-1204.

Celli et al., "Soluble dominant-negative receptor uncovers essential roles for fibroblast growth factors in multi-organ induction and patterning" The EMBO Journal, vol. 17, No. 6, Mar. 16, 1998, pp. 1642-1655.

Chellaiah et al., "Mapping ligand binding domains in chimeric fibroblast growth factor receptor molecules" J. Biol. Chem., vol. 274, No. 49, Dec. 3, 1999, pp. 34785-34794.

Cheon et al., "High-affinity binding sites for related fibroblast growth factor ligands reside within different receptor immunoglobulin-like domains" Proc. Natl. Acad. Sci., vol. 91, Feb. 1994, pp. 989-993.

Compagni et al., "Fibroblast growth factors are required for efficient tumor angiogenesis" Cancer Research, vol. 60, Dec. 15, 2000, pp. 7163-7169.

Couglin et al., "Acidic and basic fibroblast growth factors stimulate tyrosine kinase activity in vivo" J. Biol. Chem., vol. 263, No. 2, Jan. 15, 1988, pp. 988-993.

Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.

Feige et al., "Glycosylation of the basic fibroblast growth factor receptor" J. Biol. Chem., vol. 263, No. 28, Oct. 5, 1988, pp. 14023-14029.

Gowardhan et al., "Evaluation of the fibroblast growth factor system as a potential target for therapy in human prostate cancer" British Journal of Cancer, vol. 92, Jan. 18, 2005, pp. 320-327.

Grossman et al., "Expression of human thyrotropin in cell lines with different glycosylation patterns combined with mutagenesis of specific glycosylation sites" J. Biol. Chem., vol. 270, No. 49, Dec. 8, 1995, pp. 29378-29385.

Guillonneau et al., "Fibroblast growth factor (FGF) soluble receptor 1 acts as a natural inhibitor of FGF2 neurotrophic activity during retinal degeneration" Molecular Biology of the Cell, vol. 9, Oct. 1998, pp. 2785-2802.

Hanneken et al., "Identification of soluble forms of the fibroblast growth factor receptor in blood" Proc. Natl. Acad. Sci., vol. 91, Sep. 1994, pp. 9170-9174.

Hanneken et al., "Soluble forms of the high-affinity fibroblast growth factor receptor in human vitreous fluid" Investigative Opthalmology & Visual Science, vol. 36, No. 6, May 1995, pp. 1192-1196.

Hanneken et al., "Structural characterization of the circulating soluble FGF receptors reveals multiple isoforms generated by secretion and ectodomain shedding" FEBS Letters, vol. 489, 2001, pp. 176-181.

Harding et al., "Role of VEGF, PDGF and FGF in glioblastoma progression as determined by soluble decoy receptor expression in preclinical models" Cell Genesys, Inc., Abstract No. 3030, presented at the AACR Annual Meeting, Apr. 16-20, 2005, 1 page.

Johnson et al., "Diverse forms of a receptor for acidic and basic fibroblast growth factors" Molecular and Cellular Biology, vol. 10, No. 9, Sep. 1990, pp. 4728-4736.

Johnson et al, "The human fibroblast growth factor receptor genes: a common structural arrangement underlies the mechanisms for generating receptor forms that differ in their third immunoglobulin domain" Molecular and Cellular Biology, vol. 11, No. 9, Sep. 1991, pp. 4627-4634.

Kan et al., "Divalent cations and heparin-heparan sulfate cooperate to control assembly and activity of the fibroblast growth factor receptor complex" J. Biol. Chem., vol. 271, No. 42, Oct. 18, 1996, pp. 26143-26148.

Kaufman et al., "Characterization of ligand binding to immobilized biotinylated extracellular domains of three growth factor receptors" Anal. Biochem., vol. 211, No. 2, Jun. 1993, pp. 261-266.

Keifer et al., "Molecular cloning of a human basic fibroblast growth factor receptor cDNA and expression of a biologically active extracellular domain in a baculovirus system" Growth Factors, vol. 5, 1991, pp. 115-127.

Kleeff et al., "Adenovirus-mediated transfer of a truncated fibroblast growth factor (FGF) type I receptor blocks FGF-2 signaling in multiple pancreatic cancer cell lines" Pancreas, vol. 28, No. 1, Jan. 2004, pp. 25-30.

Kwabi-Addo et al., "The role of fibroblast growth factors and their receptors in prostate cancer" Endocrine-Related Cancer, vol. 11, No. 4, Dec. 2004, pp. 709-724.

Lee et al., "Purification and complementary DNA cloning of a receptor for basic fibroblast growth factor" Science, vol. 245, No. 4913, Jul. 7, 1989, pp. 57-60.

Levi et al., "Matrix metalloproteinase 2 releases active soluble ectodomain of fibroblast growth factor receptor 1", XP-002413740, Proc. Natl. Acad. Sci., USA, vol. 93, pp. 7069-7074, (Jul. 1996).

Li et al., "Cell transformation by fibroblast growth factors can be suppressed by truncated fibroblast growth factor receptors" Molecular and Cellular Biology, vol. 14, No. 11, Nov. 1994, pp. 7660-7669.

Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.

(56) References Cited

OTHER PUBLICATIONS

Lopez et al., "A novel type I fibroblast growth factor receptor activates mitogenic signaling in the absence of detectable tyrosine phosphorylation of FRS2" J. Biol. Chem., vol. 275, No. 21, May 26, 2000, pp. 15933-15939.
Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.
Mansukhani et al., "A murine fibroblast growth factor (FGF) receptor expressed in CHO cells is activated by basic FGF and Kaposi FGF" Proc. Natl. Acad. Sci., vol. 87, Jun. 1990, pp. 4378-4382.
Ogawa et al., "Anti-tumor angiogenesis therapy using soluble receptors: enhanced inhibition of tumor growth when soluble fibroblast growth factor receptor-1 is used with soluble vascular endothelial growth factor receptor" Cancer Gene Therapy, vol. 9, Aug. 2002, pp. 633-640.
Olsen et al., "Insights into the molecular basis for fibroblast growth factor receptor autoinhibition and ligand-binding promiscuity" Proc. Natl. Acad. Sci., vol. 101, No. 4 Jan. 27, 2004, pp. 935-940.
Ornitz et al., "Heparin is required for cell-free binding of basic fibroblast growth factor to a soluble receptor and for mitogenesis in whole cells" Molecular and Cellular Biology, vol. 12, Jan. 1992, pp. 240-247.
Ornitz et al., "Receptor specificity of the fibroblast growth factor family" J. Biol. Chem., vol. 271, No. 25, Jun. 21, 1996, pp. 15292-15297.
Otto et al., "Sialylated complex-type $N$-glycans enhance the signaling activity of soluble intercellular adhesion molecule-1 in mouse astrocytes" J. Biol. Chem., vol. 279, No. 34, Aug. 20, 2004, pp. 35201-35209.
Pasquale et al., "Identification of a developmentally regulated protein-tyrosine kinase by using anti-phosphotyrosine antibodies to screen a cDNA expression library" Proc. Natl. Acad. Sci., vol. 86, Jul. 1989, pp. 5449-5453.
Powers et al., "Fibroblast growth factors, their receptors and signaling", XP-002165147, Endocrine-Related Cancer, 7, pp. 165-197, (2000).
Plotnikov et al., "Structural basis for FGF receptor dimerization and activation" Cell, vol. 98, Sep. 3, 1999, pp. 641-650.
Plotnikov et al., "Crystal structures of two FGF-FGFR complexes reveal the determinants of ligand-receptor specificity" Cell, vol. 101, May 12, 2000, pp. 413-424.
Powell et al., "Fibroblast growth factor receptors 1 and 2 interact differently with heparin-heparan sulfate" J. Biol. Chem., vol. 277, No. 32, Aug. 9, 2002, pp. 28554-28563.
Roghani et al., "Heparin increases the affinity of basic fibroblast growth factor for its receptor but is not required for binding" J. Biol. Chem., vol. 269, No. 6, Feb. 11, 1994, pp. 3976-3984.
Ruta et al., "A novel protein tyrosine kinase gene whose expression is modulated during endothelial cell differentiation" Oncogene, 1988, vol. 3, pp. 9-15.
Shamim et al., "Sequential roles for Fgf4, En1 and Fgf8 in specification and regionalization of the midbrain" Development, vol. 126, Feb. 1999, pp. 945-959.
Smith et al., "The asparagine-linked oligosaccharides on tissue factor pathway inhibitor terminate with $SO_4$—4GalNAc$\beta$1,4GlcNAc$\beta$1,2Man$\alpha$" J. Biol. Chem., vol. 267, No. 27, Sep. 25, 1992, pp. 19140-19146.
St. Bernard et al., "Fibroblast growth factor receptors as molecular targets in thyroid carcinoma" Endocrinology, vol. 146, No. 3, 2005, pp. 1145-1153.
St. Bernard et al., "Fibroblast growth factor receptors as molecular targets in thyroid carcinoma" Endocrinology, vol. 10, Nov. 24, 2004, pp. 1-26 and 6 pgs. figures.
Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.
Trueb et al., "Characterization of FGFRL1, a novel fibroblast growth factor (FGF) receptor preferentially expressed in skeletal tissues" J. Biol. Chem., vol. 278, No. 36, Sep. 5, 2003, pp. 33857-33865.
Tucker et al., "A novel approach for inhibiting growth factor signalling in murine tooth development" Eur. J. Oral Sci., vol. 106 (suppl. 1), 1998, pp. 122-125.
Tuominen et al., "Expression and glycosylation studies of human FGF Receptor 4" Protein Expression and Purification, vol. 21, Mar. 2001, pp. 275-285.
Ueno et al., "A truncated form of fibroblast growth factor receptor 1 inhibits signal transduction by multiple types of fibroblast growth factor receptor" J. Biol. Chem., vol. 267, No. 3, Jan. 25, 1992, pp. 1470-1476.
Van Den Nieuwenhof et al., "Recombinant glycodelin carrying the same type of glycan structures as contraceptive glycodelin-A can be produced in human kidney 293 cells but not in Chinese hamster ovary cells" Eur. J. Biochem., vol. 267, Aug. 2000, pp. 4753-4762.
Wagner et al., "Suppression of fibroblast growth factor receptor signaling inhibits pancreatic cancer growth in vitro and in vivo" Gastroenterology, vol. 114, Apr. 1998, pp. 798-807.
Wang et al., "Purification and characterization of a functional soluble fibroblast growth factor receptor 1" Biochem. Biophys. Res. Comm., vol. 203, No. 3, Sep. 30, 1994, pp. 1781-1788.
Wang et al., "A natural kinase-deficient variant of fibroblast growth factor receptor 1" Biochemistry, vol. 35, 1996, pp. 10134-10142.
Werner et al., "Differential splicing in the extracellular region of fibroblast growth factor receptor 1 generates receptor variants with different ligand-binding specificities" Molecular and Cellular Biology, vol. 12, No. 1, Jan. 1992, pp. 82-88.
Williams et al., "Activation of the FGF receptor underlies neurite outgrowth stimulated by L1, N-CAM, and N-Cadherin" Neuron, vol. 13, Sep. 1994, pp. 583-594.
Ye et al., "FGF and Shh signals control dopaminergic and serotonergic cell fate in the anterior neural plate" Cell, vol. 93, May 29, 1998, pp. 755-766.
Office Action mailed Mar. 5, 2009, U.S. Appl. No. 11/791,889.
Amendment and Response to Restriction Requirement dated Jun. 5, 2009, in U.S. Appl. No. 11/791,889.
Office Action mailed Aug. 5, 2009, in U.S. Appl. No. 11/791,889.
Reply to Office Action dated Sep. 15, 2009, in U.S. Appl. No. 11/791,889.
Notice of Allowance and Fee(s) Due mailed Oct. 30, 2009, in U.S. Appl. No. 11/791,889.
PCT Notification of Transmittal of the International Search Report and the Written Opinion of the International Searching Authority, or the Declaration; International Search Report; and Written Opinion of the International Searching Authority, mailed Sep. 18, 2007, for International Application No. PCT-US2006-028597.
Patent Cooperation Treaty International Preliminary Report on Patentability, issued Jan. 22, 2008, in International Application No. PCT-US2006-028597.
Application for Entry into the European Phase with amended claims filed after receipt of European Search Report, filed Feb. 22, 2008, in European Application No. 06 800 260.9.
Amended claims filed after receipt of European Search Report, filed Mar. 17, 2008, in European Application No. 06 800 260.9.
Examination Report, mailed Jun. 10, 2008, in European Application No. 06 800 260.9.
Reply to Examination Report, filed Aug. 13, 2008, in European Application No. 06 800 260.9.
Examination Report, mailed Sep. 8, 2008, in European Application No. 06 800 260.9.
Reply to Examination Report, filed Dec. 17, 2008, in European Application No. 06 800 260.9.
Result of consultation by telephone of Dec. 17, 2008, with applicant-representative, mailed Dec. 30, 2008, in European Application No. 06 800 260.9.
Examination Report, mailed Jan. 22, 2009, in European Application No. 06 800 260.9.
Reply to Examination Report, filed Mar. 6, 2009, in European Application No. 06 800 260.9.
Reply to Examination Report, filed May 22, 2009, in European Application No. 06 800 260.9.

(56) References Cited

OTHER PUBLICATIONS

European Search Report, mailed Jun. 5, 2009, in European Application No. 09 075 061.3.
Examination Report, mailed Sep. 25, 2009, in European Application No. 09 075 061.3.
Reply to Examination Report, filed Feb. 25, 2010, in European Application No. 09 075 061.3.
Office Action mailed Nov. 17, 2010, in U.S. Appl. No. 12/652,720.
Response to Restriction Requirement and Supplemental Preliminary Amendment dated Feb. 17, 2011, in U.S. Appl. No. 12/652,720.
Notice of Allowance and Fee(s) Due mailed Mar. 11, 2011, in U.S. Appl. No. 12/652,720.
Restriction Requirement mailed Nov. 18, 2011, in U.S. Appl. No. 13/157,712.
Preliminary Amendment and Response to Species Election dated Dec. 16, 2011, in U.S. Appl. No. 13/157,712.
Notice of Allowance and Fee(s) Due mailed Jan. 13, 2012, in U.S. Appl. No. 13/157,712.
Harding et al., "Preclinical Efficacy of FP-1039 (FGFR1:Fc) in Endometrial Carcinoma Models with Activating Mutations in FGFR2," AACR 101st Annual Meeting Poster (Apr. 17-21, 2010).
Tolcher et al., "Preliminary Results of a Phase 1 Study of FP-1039 (FGFR1:Fc), A Novel Antagonist of Multiple Fibroblast Growth Factor (FGF) Ligands, in Patients With Advanced Malignancies," 2009 AACR-EORTC-NCI Molecular Targets and Cancer Therapeutics Conference Poster (Nov. 15-18, 2009).
Tolcher et al., "Preliminary Results of a Dose Escalation Study of the Fibroblast Growth Factor (FGF) "trap" FP-1039 (FGFR1:Fc) in Patients With Advanced Malignancies," 22nd EORTC-NCI-AACR Symposium on Molecular Targets and Cancer Therapeutics Poster (Nov. 16-19, 2010).
Tolcher et al., "Preliminary results of a dose escalation study of the Fibroblast Growth Factor (FGF) "trap" FP-1039 (FGFR1:Fc) in patients with advanced malignancies," European Journal of Cancer, Supplement, 8(7): 121, Abstract No. 381 (Nov. 18, 2010).
PCT International Search Report and Written Opinion of the International Searching Authority mailed Jan. 31, 2012, in International Application No. PCT/US2011/060661.
Long et al. "Abstract #2789: Antitumor efficacy of FP-1039, a soluble FGF receptor 1:Fc conjugate, as a single agent or in combination with anticancer drugs," Proceedings of the American Association for Cancer Research, Apr. 18-22, 2009 Denver, CO.
Long et al. "Preclinical antitumor efficacy of FP-1039, a soluble FGF receptor 1:Fc conjugate, as a single agent or in combination with anticancer drugs," Proceedings of the American association for Cancer Research, Apr. 17-22, 2009 Denver, CO.
Rang et al, "Cancer chemotherapy," *Rand and Dale's Pharmacology*, Churchill Linvingston Elsevier, 2008, pp. 718-735.
Zheng et al. "Enhanced efficacy in anti-tumour activity by combined therapy of recombinant FGFR-1 related angiogenesis and low-dose cytotoxic agent," European Journal of Cancer, vol. 43, No. 14, Sep. 14, 2007, pp. 2134-2139.
PCT International Search Report and Written Opinion of the International Searching Authority mailed Apr. 12, 2012, in International Application No. PCT/US2011/060666.
U.S. Appl. No. 13/675,255, filed Nov. 13, 2012, Harding et al.
Andre et al., "Molecular Characterization of Breast Cancer with High-Resolution Oligonucleotide Comparative Genomic Hybridization Array," *Clin Cancer Res*, 2009, 15(2): 441-451.
Bansal et al., "The Molecular Biology of Endometrial Cancers and the Implications for Pathogenesis, Classification, and Targeted Therapies," *Cancer Control*, 2009, 16(1): 8-13.
Bass et al., "SOX2 is an Amplified Lineage Survival Oncogene in Lung and Esophageal Squamous Cell Carcinomas," *Nat. Genet.*, 2009, 41(11): 1238-1242, including supplemental information (15 pages) (corresponds to author manuscript, 16 pages).
Beroukhim et al., "The landscape of somatic copy-number alteration across human cancers," *Nature*, 2010, 463: 899-905.

Bjornsson et al., Pharmacokinetics of Heparin. II. Studies of Time Dependence in Rats, *The Journal of Pharmacology and Experimental Therapeutics*, 1979, 210(2): 243-246.
Byron et al., "Inhibition of Activated Fibroblast Growth Factor Receptor 2 in Endometrial Cancer Cells Induces Cell Death Despite PTEN Abrogation," *Cancer Res*, 2008, 68(17):6902-6907.
Byron and Pollock, "FGFR2 as a molecular target in endometrial cancer," *Future Oncol*, 2009, 5(1):27-32.
Byron et al., "FGFR2 mutations are rare across histologic subtypes of ovarian cancer," *Gynecologic Oncology*, 2010, 117(1): 125-129.
Choo et al., "SPdb—a Signal Peptide Database," *BMC Bioinformatics*, vol. 6, No. 249, Oct. 2005, pp. 1-8.
Courjal et al., "Comparative Genomic Hybridization Analysis of Breast Tumors with Predetermined Profiles of DNA Amplification," *Cancer Res*. 1997, 57(19): 4368-77.
Cuny et al., "Relating genotype and phenotype in breast cancer: an analysis of the prognostic significance of amplification at eight different genes or loci and of *p53* mutations," *Cancer Res*. 2000; 60: 1077-83.
Dutt et al., "Drug-sensitive *FGFR2* mutations in endometrial carcinoma," *PNAS*, 2008, 105(25): 8713-8717.
Dutt et al., "Inhibitor-Sensitive *FGFR1* Amplification in Human Non-Small Cell Lung Cancer," 2011, *PLoS ONE*, 6(6): e20351, 10 pages.
Elbauomy Elsheikh et al., "*FGFR1* amplification in breast carcinomas: a chromogenic in situ hybridisation analysis," *Breast Cancer Research*, 2007, 9:R23, 12 pages.
Gatius et al., "*FGFR2* alterations in endometrial carcinoma," *Modern Pathology*, 2011, 24: 1500-1510.
Gelsi-Boyer et al., "Comprehensive Profiling of 8p11-12 Amplification in Breast Cancer," *Mol Cancer Res*, 2005;3(12): 655-667.
Genbank Accession No. X76885, 1994, 2 pages.
Genbank Accession No. Q90330, Nov. 1, 1996, 6 pages.
Ibrahimi et al., "Structural basis for fibroblast growth factor receptor 2 activation in Apert syndrome," *PNAS*, 2001, 98(13): 7182-7187.
Ibrahimi et al., "Biochemical analysis of pathogenic ligand-dependent FGFR2 mutations suggests distinct pathophysiological mechanisms for craniofacial and limb abnormalities," *Human Molecular Genetics*, 2004, 13(19): 2313-2324.
Ibrahimi et al., "Proline to arginine mutations in FGF receptors 1 and 3 result in Pfeiffer and Muenke craniosynostosis syndromes through enhancement of FGF binding affinity," *Hum. Mol. Genet.*, 13: 69-78 (2004).
Ibrahimi et al., "Analysis of Mutations in Fibroblast Growth Factor (FGF) and a Pathogenic Mutation in FGF Receptor (FGFR) Provides Direct Evidence for the Symmetric Two-End Model for FGFR Dimerization," *Mol. Cell. Biol.*, 25(2): 671-684 (2005).
Katoh, "Cancer genomics and genetics of FGFR2 (Review)," International Journal of *Oncology*, 2008, 33:233-237.
Katoh, "FGFR2 Abnormalities Underlie a Spectrum of Bone, Skin, and Cancer Pathologies," *Journal of Investigative Dermatology*, 2009, 129:1861-1867.
Keer et al., "Abstract #TPS260: Enrolling a Rare Patient Population: Establishing Proof of Concept for FP-1039, an FGF "Trap," in Endometrial Cancer Patients with the S252W FGFR2 Mutation," American Society of Clinical Oncology 2010 Annual Meeting Poster (Jun. 4-8, 2010).
Lazar et al., "Transforming Growth Factor α: Mutation of Aspartic Acid 47 and Leucine 48 Results Different Biological Activities," *Mol Cell Biol*, 1988, 8(3):1247-1252.
Lee et al., "Molecular profiles of EGFR, K-ras, c-met, and FGFR in pulmonary pleomorphic carcinoma, a rare lung malignancy," *J. Cancer Res. Clin. Oncol.*, 2011, 9: 1203-1211.
Liu et al, "Utilization of Unlabeled Probes for the Detection of Fibroblast Growth Factor Receptor 2 Exons 7 and 12 Mutations in Endometrial Carcinoma," *Appl Immunohistochem Mol Morphol*, 2011, 19(4):341-346.
Loo et al., "Production and characterization of the extracellular domain of recombinant human fibroblast growth factor receptor 4," *Intl. J. Biochem. Cell Biol.*, 32: 489-497 (2000).
Marics et al., "FGFR4 signaling is a necessary step in limb muscle differentiation," *Development*, 2002, 129:4559-4569.

(56) References Cited

OTHER PUBLICATIONS

Marshall et al., "Fibroblast Growth Factor Receptors Are Components of Autocrine Signaling Networks in Head and Neck Squamous Cell Carcinoma Cells," Clin Cancer Res. , 2011, 17(15): 5016-5025 (corresponds to author manuscript, 19 pages).
Meijer et al., "Fibroblast Growth Factor Receptor 4 Predicts Failure on Tamoxifen Therapy in Patients with Recurrent Breast Cancer," Endocrine-Related Cancer, vol. 15, 2008, pp. 101-111.
Moloney et al., "Exclusive paternal origin of new mutations in Apert syndrome," Nature Genetics, 1996, 13:48-53.
Pellegrini et al., "Crystal structure of fibroblast growth factor receptor ectodomain bound to ligand and heparin," Nature, 407: 1029-1034 (2000).
Pollock et al., "Frequent activating FGFR2 mutations in endometrial carcinomas parallel germline mutations associated with craniosynostosis and skeletal dysplasia syndromes," Oncogene, 2007, 26:7158-7162.
Reis-Filho et al., "FGFR1 Emerges as a Potential Therapeutic Target for Lobular Breast Carcinomas," Clin. Cancer Res., 12(22): 6652-6662 (2006).
Robertson et al., "Activating mutations in the extracellular domain of the fibroblast growth factor receptor 2 function by disruption of the disulfide bond in the third immunoglobulin-like domain," Proc. Natl. Acad. Sci., USA, 95: 4567-4572 (1998).
Sahadevan et al., "Selective Over-expression of Fibroblast Growth Factor Receptors I and 4 in Clinical Prostate Cancer," Journal of Pathology, vol. 213, Jul. 2007, pp. 82-90.
Sanchez-Heras et al., "The fibroblast growth factor receptor acid box is essential for interactions with N-cadherin and all of the major isoforms of neural cell adhesion molecules," J Biol Chem, 2006, 281(46):35208-16.
Schlessinger et al., "Crystal Structure of the Ternary FGF-FGFR-Heparin Complex Reveals a Dual Role for Heparin in FGFR Binding and Dimerization," Molecular Cell, 6: 743-750 (2000).
Stauber et al., "Structural interaction of fibroblast growth factor receptor with its ligands," Proc. Natl. Acad. Sci., USA, 97(1): 49-54 (2000).
Sugiura et al., "Co-expression of aFGF and FGFR-1 is predictive of a poor prognosis in patients with esophageal squamous cell carcinoma," Oncology Reports, 2007, 17: 557-564.
Turner et al., "FGFR1 Amplification Drives Endocrine Therapy Resistance and is a Therapeutic Target in Breast Cancer," Cancer Research, 2010, 70(5): 2085-2094.
Turner et al., "A Therapeutic Target for Smoking-Associated Lung Cancer," Science Trans. Med., 2(62): 62ps56 (2010), 4 pages.
Voortman et al., "Array comparative genomic hybridization-based characterization of genetic alterations in pulmonary neuroendocrine tumors," PNAS, 107(29): 13040-13045 (2010).
Wang et al., "Alternately Spliced $NH_2$-terminal Immunoglobulin-like Loop I in the Ectodomain of the Fibroblast Growth Factor (FGF) Receptor 1 Lowers Affinity for both Heparin and FGF-1," J. Biol. Chem, 270(17): 10231-10235 (1995).
Weiss et al., "Frequent and Focal FGFR1 Amplification Associates with Therapeutically Tractable FGFR1 Dependency in Squamous Cell Lung Cancer," Science Trans. Med., 2010, 2(62): 62ra93, 8 pages.
Wells, "Additivity of Mutational Effects in Proteins," Biochemistry, 1990, 29(37):8509-8517.
Yu et al., "Loss of fibroblast growth factor receptor 2 ligand-binding specificity in Apert syndrome," PNAS, 2000, 97(26):14536-14541.
Zhang et al., "Receptor Specificity of the Fibroblast Growth Factor Family: The Complete Mammalian FGF Family," The Journal of Biological Chemistry, vol. 281, No. 23, Jun. 9, 2006, pp. 15694-15700 (corresponds to author manuscript, 15 pages).
Zhang et al., "FP-1039 (FGFR1:Fc), A Soluble FGFR1 Receptor Antagonist, Inhibits Tumor Growth and Angiogenesis," AACR-NCI-EORTC International Conference Molecular Targets and Cancer Therapeutics Discovery, Biology and Clinical Applications Poster (Oct. 22-26, 2007).
Office Action mailed Sep. 11, 2012, in U.S. Appl. No. 13/296,161.
Restriction Requirement mailed Oct. 11, 2012, in U.S. Appl. No. 13/438,638.
Response to Restriction Requirement and Interview Summary filed Nov. 8, 2012, in U.S. Appl. No. 13/438,638.
Office Action mailed Dec. 5, 2012, in U.S. Appl. No. 13/438,638.
Response to Office Action filed Dec. 6, 2012, in U.S. Appl. No. 13/296,161.
Notice of Allowance and Fee(s) Due mailed Dec. 27, 2012, in U.S. Appl. No. 13/296,161.
Restriction Requirement mailed Nov. 5, 2012, in U.S. Appl. No. 13/509,068.
Amendment and Response to Species Election Requirement filed Dec. 21, 2012, in U.S. Appl. No. 13/509,068.
Harding et al., "Preclinical efficacy of fibroblast growth factor ligand trap HGS1036 in lung carcinoma models with genomic amplification of FGFR1" Poster from AACR Annual Meeting, Mar. 31-Apr. 4, 2012, 1 page.
Harding et al., "Blockade of Nonhormonal Fibroblast Growth Factors by FP-1039 Inhibits Growth of Multiple Types of Cancer," Sci Transl Med, 5: 1-9 (2013).
Harding et al., "Supplementary Materials for Blockade of Nonhormonal Fibroblast Growth Factors by FP-1039 Inhibits Growth of Multiple Types of Cancer," Sci Transl Med, vol. 5, 28 pages (2013).
Jang et al., "FGFR1 is amplified during the progression of in situ to invasive breast carcinoma," Breast Cancer Research, 14(R115): 1-12 plus Table S1 (1 page) (2012).
Knights et al., "De-regulated FGF receptors as therapeutic targets in cancer," Pharmacology & Therapeutics, 125(1):105-117 (2010).
Tacer et al., "Research Resource: Comprehensive Expression Atlas of the Fibroblast Growth Factor System in Adult Mouse," Mol Endocrinol, 24(10): 2050-2064, including supplementary information, 23 pages total (2010).
Zytovision GmbH, Catalogue 2011, $1^{st}$ Edition, 84 pages.
PCT International Search Report and Written Opinion of the International Searching Authority mailed Apr. 1, 2013, for International Application No. PCT/US2012/064772 (16 pages).
Adam et al., "Toward optimized front-line therapeutic strategies in patients with metastatic colorectal cancer—an expert review from the International Congress on Anti-cancer Treatment (ICACT) 2009," Annals of Oncology, 21: 1579-1584 (2010).
Fuchs et al., "Cytologic Evidence That Taxol, an Antineoplastic Agent from Taxus brevifolia, Acts as a Mitotic Spindle Poison," Cancer Treatment Reports, 62(8): 1219-1222 (1978).
Heidelberger et al., "Fluorinated Pyrimidines, a New Class of Tumour-inhibitory Compounds," Nature, 179(4561): 663-666 (1957).
Johnson et al., "The Vinca Alkaloids: A New Class of Oncolytic Agents," Cancer Res, 23: 1390-1427 (1963).
Longley et al., "5-Fluorouracil: mechanisms of action and clinical strategies," Nature Reviews Cancer 3: 330-338 (2003).
Ma et al., "Combination of antiangiogenesis with chemotherapy for more effective cancer treatment," Mol Cancer Ther, 7: 3670-3684 (2008).
Mayer et al., "Ratiometric dosing of anticancer drug combinations: Controlling drug ratios after systemic administration regulates therapeutic activity in tumor-bearing mice," Mol Cancer Ther, 5(7): 1854-1863 (2006).
McClean et al., "Sequence selectivity, cross-linking efficiency and cytotoxicity of DNA-targeted 4-anilinoquinoline aniline mustards," Anti-Cancer Drug Design, 14: 187-204 (1999).
Reynolds et al., "Evaluating Response to Antineoplastic Drug Combinations in Tissue Culture Models," from Methods in Molecular Medicine, vol. 110: Chemosensitivity: vol. 1: In Vitro Assays, Edited by R.D. Blumenthal, Humana Press Inc., Totowa, NJ, pp. 173-183, 2005.
Rosenberg et al., "Inhibition of Cell Division in Escherichia coli by Electrolysis Products from a Platinum Electrode," Nature, 205(4972): 698-699 (1965).
Rosenberg et al., "The Inhibition of Growth or Cell Division in Escherichia coli by Different Ionic Species of Platinum(IV) Complexes," J Biological Chemistry, 242 (6): 1347-1352 (1967).

(56) References Cited

OTHER PUBLICATIONS

Rosenberg et al., "Platinum compounds: a New Class of Potent Antitumour Agents," Nature, 222: 385-386 (1969).
Seshacharyulu et al., "Targeting the EGFR signaling pathway in cancer therapy," Expert Opin Ther Targets, 16(1): 15-31 (2012).
Taraboletti et al., "Potential Antagonism of Tubulin-Binding Anti-cancer Agents in Combination Therapies," Clin Cancer Res 11(7): 2720-2726 (2005).
Wall et al., "Camptothecin and Taxol: Discovery to Clinic—Thirteenth Bruce F. Cain Memorial Award Lecture," Cancer Res 55: 753-760 (1995).
Yoo et al., "Docetaxel Associated Pathways in Cisplatin Resistant Head and Neck Squamous Cell Carcinoma: A Pilot Study," Laryngoscope, 115: 1938-1946 (2005).
File History for U.S. Appl. No. 13/905,042, filed May 29, 2013.
File History for U.S. Appl. No. 13/913,292, filed Jun. 7, 2013.
File History for U.S. Appl. No. 14/185,086, filed Feb. 20, 2014.
File History for U.S. Appl. No. 14/357,336, filed May 9, 2014.
International Search Report and written Opinion mailed Mar. 8, 2010 for PCT/US2009/052704, filed Aug. 4, 2009, 14 pages.
International Search Report and written Opinion mailed Feb. 4, 2011 for PCT/US2010/056627, 15 pages.
European Search Report, mailed May 2, 2013, in European Patent Application No. 10817774.2, 8 pages.
File History for U.S. Appl. No. 11/791,889, filed May 30, 2007.
File History for U.S. Appl. No. 12/652,720, filed Jan. 5, 2010.
File History for U.S. Appl. No. 13/157,712, filed Jun. 10, 2011.
File History for U.S. Appl. No. 13/227,398, filed Sep. 7, 2011.
File History for U.S. Appl. No. 13/296,161, filed Nov. 14, 2011.
File History for U.S. Appl. No. 13/496,182, filed Mar. 14, 2012.
File History for U.S. Appl. No. 13/438,638, filed Apr. 3, 2012.
File History for U.S. Appl. No. 13/509,068, filed Jun. 13, 2012.
File History for U.S. Appl. No. 13/612,044, filed Sep. 12, 2012.
File History for U.S. Appl. No. 13/675,255, filed Nov. 13, 2012.
File History for U.S. Appl. No. 13/515,429, filed Nov. 21, 2012.

\* cited by examiner

SEQUENCE LISTING

<160> NUMBER OF SEQ ID NOS: 10

<210> SEQ ID NO 1
<211> LENGTH: 374
<212> TYPE: PRT
<213> ORGANISM: Homo sapiens

<400> SEQUENCE: 1

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365
```

```
Ser Pro Leu Tyr Leu Glu
    370

<210> SEQ ID NO 2
<211> LENGTH: 353
<212> TYPE: PRT
<213> ORGANISM: Homo sapiens

<400> SEQUENCE: 2

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro Leu Tyr Leu
            340                 345                 350

Glu
```

```
<210> SEQ ID NO 3
<211> LENGTH: 360
<212> TYPE: PRT
<213> ORGANISM: Homo sapiens

<400> SEQUENCE: 3

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu
        355                 360

<210> SEQ ID NO 4
```

```
<211> LENGTH: 339
<212> TYPE: PRT
<213> ORGANISM: Homo sapiens

<400> SEQUENCE: 4

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu

<210> SEQ ID NO 5
<211> LENGTH: 592
<212> TYPE: PRT
<213> ORGANISM: Homo sapiens

<400> SEQUENCE: 5
```

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                      70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Ser Glu Glu Lys Glu Thr Asp Asn Thr
130                     135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
        210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
        290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Pro Lys Ser Ser Asp Lys Thr
            355                 360                 365

His Thr Cys Pro Pro Cys Pro Ala Pro Glu Leu Leu Gly Gly Pro Ser
        370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
```

```
            420              425               430
Lys Thr Lys Pro Arg Glu Glu Gln Tyr Asn Ser Thr Tyr Arg Val Val
        435                 440              445

Ser Val Leu Thr Val Leu His Gln Asp Trp Leu Asn Gly Lys Glu Tyr
        450                 455              460

Lys Cys Lys Val Ser Asn Lys Ala Leu Pro Ala Pro Ile Glu Lys Thr
465             470              475              480

Ile Ser Lys Ala Lys Gly Gln Pro Arg Glu Pro Gln Val Tyr Thr Leu
            485              490              495

Pro Pro Ser Arg Asp Glu Leu Thr Lys Asn Gln Val Ser Leu Thr Cys
            500              505              510

Leu Val Lys Gly Phe Tyr Pro Ser Asp Ile Ala Val Glu Trp Glu Ser
        515                 520              525

Asn Gly Gln Pro Glu Asn Asn Tyr Lys Thr Thr Pro Pro Val Leu Asp
        530                 535              540

Ser Asp Gly Ser Phe Phe Leu Tyr Ser Lys Leu Thr Val Asp Lys Ser
545             550              555              560

Arg Trp Gln Gln Gly Asn Val Phe Ser Cys Ser Val Met His Glu Ala
            565              570              575

Leu His Asn His Tyr Thr Gln Lys Ser Leu Ser Leu Ser Pro Gly Lys
            580              585              590

<210> SEQ ID NO 6
<211> LENGTH: 571
<212> TYPE: PRT
<213> ORGANISM: Homo sapiens

<400> SEQUENCE: 6

Arg Pro Ser Pro Thr Leu Pro Glu Gln Ala Gln Pro Trp Gly Ala Pro
1               5                10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65              70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
            165                 170                 175

Asp His Arg Ile Gly Gly Tyr Lys Val Arg Tyr Ala Thr Trp Ser Ile
        180                 185                 190

Ile Met Asp Ser Val Val Pro Ser Asp Lys Gly Asn Tyr Thr Cys Ile
    195                 200                 205
```

Val Glu Asn Glu Tyr Gly Ser Ile Asn His Thr Tyr Gln Leu Asp Val
210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
                260                 265                 270

Asn Gly Ser Lys Ile Gly Pro Asp Asn Leu Pro Tyr Val Gln Ile Leu
            275                 280                 285

Lys Thr Ala Gly Val Asn Thr Thr Asp Lys Glu Met Glu Val Leu His
290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Pro Lys Ser Ser Asp Lys Thr His Thr Cys Pro Pro
                340                 345                 350

Cys Pro Ala Pro Glu Leu Leu Gly Gly Pro Ser Val Phe Leu Phe Pro
355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
    435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 7
<211> LENGTH: 21
<212> TYPE: PRT
<213> ORGANISM: Homo sapiens

<400> SEQUENCE: 7

Met Trp Ser Trp Lys Cys Leu Leu Phe Trp Ala Val Leu Val Thr Ala
1               5                   10                  15

Thr Leu Cys Thr Ala
            20

<210> SEQ ID NO 8
<211> LENGTH: 232
<212> TYPE: PRT
<213> ORGANISM: Homo sapiens

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 9
<211> LENGTH: 228
<212> TYPE: PRT
<213> ORGANISM: Homo sapiens

<400> SEQUENCE: 9

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

```
Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 10
<211> LENGTH: 229
<212> TYPE: PRT
<213> ORGANISM: Homo sapiens

<400> SEQUENCE: 10

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

-continued

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

FGFR1 EXTRACELLULAR DOMAIN COMBINATION THERAPIES FOR LUNG CANCER

RELATED APPLICATIONS

This application is a non-provisional application filed under 37 CFR 1.53(b)(1), claiming priority under 35 USC 119 (e) to provisional application No. 61/421,462 filed Dec. 9, 2010, the content of which is incorporated herein by reference.

BACKGROUND AND SUMMARY OF THE INVENTION

Soluble forms of Fibroblast Growth Factor Receptor 1 (FGFR1) have been shown to inhibit tumor cell growth in vitro and in vivo. See, e.g., U.S. Pat. No. 7,678,890. Combining an anti-cancer therapeutic molecule, such as a soluble form of FGFR1, with another anti-cancer therapeutic molecule, can result in antagonistic, additive, or synergistic effects on the efficacy of each of the anti-cancer therapeutics.

The inventors have discovered that administration of an FGFR1 ECD and docetaxel in a mouse xenograft model of non-small cell lung cancer shows synergistic anti-tumor activity of the therapeutic agents. In addition, the inventors have discovered that administration of an FGFR1 ECD and at least one additional therapeutic molecule selected from paclitaxel, vincristine, carboplatin, cisplatin, oxaliplatin, doxorubicin, 5-fluorouracil (5-FU), leucovorin, pemetrexed, and bevacizumab, has at least additive activity relative to each molecule administered alone in certain mouse xenograft models.

In some embodiments, methods of treating cancer comprising administering to a subject a fibroblast growth factor receptor 1 (FGFR1) extracellular domain (ECD) and at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a vascular endothelial growth factor (VEGF) antagonist, a VEGF trap, an anti-VEGF antibody, and bevacizumab are provided. In some embodiments, the at least one additional therapeutic agent is docetaxel. In some embodiments, the at least one additional therapeutic agent is pemetrexed. In some embodiments, the at least one additional therapeutic agent is cisplatin. In some embodiments, the at least one additional therapeutic agent is paclitaxel. In some embodiments, the at least one additional therapeutic agent is 5-FU. In some embodiments, the at least one additional therapeutic agent is topotecan. In some embodiments, the at least one additional therapeutic agent is viscristine. In some embodiments, the at least one additional therapeutic agents is a VEGF antagonist, such as an anti-VEGF antibody or a VEGF trap. In some embodiments, the at least one additional therapeutic agent is bevacizumab. In some embodiments, the at least one additional therapeutic agent is sorafenib. In some embodiments, the FGFR1 ECD comprises a sequence selected from SEQ ID NOs: 1 to 4.

In some embodiments, methods of treating cancer comprising administering to a subject a fibroblast growth factor receptor 1 (FGFR1) extracellular domain (ECD) fusion molecule and at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a vascular epithelial growth factor (VEGF) antagonist, a VEGF trap, an anti-VEGF antibody, and bevacizumab are provided, wherein the FGFR1 ECD fusion molecule comprises an FGFR1 ECD and a fusion partner. In some embodiments, the at least one additional therapeutic agent is docetaxel. In some embodiments, the at least one additional therapeutic agent is pemetrexed. In some embodiments, the at least one additional therapeutic agent is cisplatin. In some embodiments, the at least one additional therapeutic agent is paclitaxel. In some embodiments, the at least one additional therapeutic agent is 5-FU. In some embodiments, the at least one additional therapeutic agent is viscristine. In some embodiments, the at least one additional therapeutic agent is topotecan. In some embodiments, the at least one additional therapeutic agent is a VEGF antagonist, such as an anti-VEGF antibody or a VEGF trap. In some embodiments, the at least one additional therapeutic agent is bevacizumab. In some embodiments, the at least one additional therapeutic agent is sorafenib.

In some embodiments, methods of treating cancer comprising administering to a subject an FGFR1 ECD or FGFR1 ECD fusion molecule and at least two additional therapeutic agents selected from docetaxel, paclitaxel, vincristine, carboplatin, cisplatin, oxaliplatin, doxorubicin, 5-fluorouracil (5-FU), leucovorin, pemetrexed, etoposide, sorafenib, etoposide, topotecan, a vascular epithelial growth factor (VEGF) antagonist, a VEGF trap, an anti-VEGF antibody, and bevacizumab are provided, wherein the FGFR1 ECD fusion molecule comprises an FGFR1 ECD and a fusion partner. In some embodiments, at least one of the two additional therapeutic agents is paclitaxel. In some embodiments, at least one of the two additional therapeutic agents is cisplatin. In some embodiments, at least one of the two additional therapeutic agents is carboplatin. In some embodiments, at least one of the two additional therapeutic agents is oxaliplatin. In some embodiments, at least one of the two additional therapeutic agents is 5-FU. In some embodiments, at least one of the two additional therapeutic agents is doxorubicin. In some embodiments, at least one of the two additional therapeutic agents is etoposide. In some embodiments, at least one of the two additional therapeutic agents is topotecan. In some embodiments, at least one of the two additional therapeutic agents is a VEGF antagonist, such as an anti-VEGF antibody or a VEGF trap. In some embodiments, at least one of the two additional therapeutic agents is bevacizumab. In some embodiments, the two additional therapeutic agents are paclitaxel and carboplatin. In some embodiments, the two additional therapeutic agents are doxorubicin and paclitaxel. In some embodiments, the two additional therapeutic agents are cisplatin and etoposide. In some embodiments, the two additional therapeutic agents are oxaliplatin and 5-FU. In some embodiments, the two additional therapeutic agents are 5-FU and leucovorin. In some embodiments, the two additional therapeutic agents are 5-FU and bevacizumab. In some embodiments, the two additional therapeutic agents are paclitaxel and bevacizumab. In some embodiments, the two additional therapeutic agents are cisplatin and etoposide.

In some embodiments, methods of treating cancer comprising administering to a subject an FGFR1 ECD or FGFR1 ECD fusion molecule and at least three additional therapeutic agents selected from docetaxel, paclitaxel, vincristine, carboplatin, cisplatin, oxaliplatin, doxorubicin, 5-fluorouracil (5-FU), leucovorin, pemetrexed, etoposide, sorafenib, a VEGF antagonist, an anti-VEGF antibody, a VEGF trap, and bevacizumab are provided, wherein the FGFR1 ECD fusion molecule comprises an FGFR1 ECD and a fusion partner. In some embodiments, at least one of the three additional therapeutic agents is oxaliplatin. In some embodiments, at least one of the three additional therapeutic agents is 5-FU. In some embodiments, at least one of the three additional therapeutic agents is leucovorin. In some embodiments, at least one of the three additional therapeutic agents is carboplatin. In some embodiments, at least one of the three additional therapeutic agents is paclitaxel. In some embodiments, at least one of the three additional therapeutic agents is bevacizumab. In some embodiments, the three additional therapeutic agents are oxaliplatin, 5-FU and leucovorin. In some embodiments, the three additional therapeutic agents are bevacizumab, 5-FU and leucovorin. In some embodiments, at least two of the three additional therapeutic agents are cisplatin and etoposide.

The invention also relates, in some embodiments, to a combination of an FGFR1 ECD or FGFR1 ECD fusion molecule and at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a vascular endothelial growth factor (VEGF) antagonist, a VEGF trap, an anti-VEGF antibody, and bevacizumab, for treatment of cancer. The invention further relates, in some embodiments to a combination of an FGFR1 ECD or FGFR1 ECD fusion molecule and at least two additional therapeutic agents selected from docetaxel, paclitaxel, vincristine, carboplatin, cisplatin, oxaliplatin, doxorubicin, 5-fluorouracil (5-FU), leucovorin, pemetrexed, etoposide, sorafenib, etoposide, topotecan, a vascular epithelial growth factor (VEGF) antagonist, a VEGF trap, an anti-VEGF antibody, and bevacizumab, for treatment of cancer. The invention also relates, in some embodiments, to a combination of an FGFR1 ECD or FGFR1 ECD fusion molecule and at least three additional therapeutic agents selected from docetaxel, paclitaxel, vincristine, carboplatin, cisplatin, oxaliplatin, doxorubicin, 5-fluorouracil (5-FU), leucovorin, pemetrexed, etoposide, sorafenib, a VEGF antagonist, an anti-VEGF antibody, a VEGF trap, and bevacizumab, for treatment of cancer.

In some embodiments, the FGFR1 ECD and/or FGFR1 ECD fusion molecule is packaged separately from the at least one, at least two, or at least three additional therapeutic agents. In some embodiments, the FGFR1 ECD and/or FGFR1 ECD fusion molecule is not mixed with the at least one, at least two, or at least three additional therapeutic agents prior to administration.

In some embodiments, a method of treating cancer comprising administering to a subject an FGFR1-ECD.339-Fc and docetaxel is provided, wherein the FGFR1-ECD.339-Fc comprises the amino acid sequence of SEQ ID NO: 6. In some embodiments, a method of treating cancer comprising administering to a subject an FGFR1-ECD.339-Fc and docetaxel is provided, wherein the FGFR1-ECD.339-Fc consists of the amino acid sequence of SEQ ID NO: 6.

In some embodiments, an FGFR1 ECD or FGFR1 ECD fusion molecule is glycosylated and/or sialylated. In some embodiments, an FGFR1 ECD or the polypeptide portion of the FGFR1 ECD fusion molecule is expressed in Chinese hamster ovary (CHO) cells. In some embodiments, an FGFR1 ECD comprises an amino acid sequence selected from SEQ ID NO: 1 and SEQ ID NO: 3.

In some embodiments, at least one dose of an FGFR1 ECD and/or an FGFR1 ECD fusion molecule and at least one dose of at least one additional therapeutic agent are administered concurrently. In some embodiments, at least one dose of an FGFR1 ECD and/or an FGFR1 ECD fusion molecule and at least one dose of at least one additional therapeutic agent are administered at the same time.

In some embodiments, the FGFR1 ECD comprises an amino acid sequence selected from SEQ ID NOs: 1 to 4. In some embodiments, at least one fusion partner is selected from an Fc, albumin, and polyethylene glycol. In some embodiments, at least one fusion partner is an Fc. In some embodiments, the Fc comprises an amino acid sequence selected from SEQ ID NOs: 8 to 10. In some embodiments, the FGFR1 ECD fusion molecule comprises a sequence selected from SEQ ID NO: 5 and SEQ ID NO: 6. In some embodiments, the at least one fusion partner is an Fc and polyethylene glycol. In some embodiments, the at least one fusion partners is polyethylene glycol. In some embodiments, the fusion molecule comprises a linker between the FGFR1 ECD and one or more fusion partners. In some embodiments, the FGFR1 ECD comprises a signal peptide. In some embodiments, the signal peptide comprises the amino acid sequence of SEQ ID NO: 7.

In some embodiments, the FGFR1 ECD fusion molecule is an amount in the range of about 0.5 mg/kg body weight to about 20 mg/kg body weight, such as an amount in the range of about 8 to about 16 mg/kg body weight. In some embodiments, the therapeutically effective amount of the FGFR1 ECD fusion molecule is a dose of about 8 mg/kg body weight, while in some embodiments, the therapeutically effective amount of the FGFR1 ECD fusion molecule is a dose of about 16 mg/kg body weight (or at about 10 mg/kg body weight or about 20 mg/kg body weight, respectively, when calculated using an extinction coefficient of 1.11 mL/mg*cm). In some embodiments, the therapeutically effective amount of FGFR1 ECD fusion molecule is a dose of about 20 mg/kg body weight. In some embodiments, dosages may be administered twice a week, weekly, every other week, at a frequency between weekly and every other week, every three weeks, every four weeks, or every month.

The invention also relates, in some embodiments, to a dosage pack. In some embodiments, a dosage pack comprising at least one component selected from: (i) a fibroblast growth factor receptor 1 (FGFR1) extracellular domain (ECD), (ii) a fibroblast growth factor receptor 1 (FGFR1) extracellular domain (ECD) fusion molecule, and (iii) at least one additional therapeutic agent selected from docetaxel, paclitaxel, vincristine, carboplatin, cisplatin, oxaliplatin, doxorubicin, 5-fluorouracil (5-FU), leucovorin, pemetrexed, etoposide, topotecan, a VEGF antagonist, an anti-VEGF antibody, a VEGF trap, bevacizumab, and sorafenib; and instructions for administering an FGFR1 ECD or FGFR1 ECD fusion molecule and the at least one additional therapeutic to a patient is provided. In some embodiments, the instructions included with the dosage pack comprise instructions for administering a therapeutically effective amount of FGFR1 ECD fusion molecule. In some embodiments, the therapeutically effective amount of the FGFR1 ECD fusion molecule is an amount in the range of about 0.5 mg/kg body weight to about 20 mg/kg body weight, such as an amount in the range of about 8 to about 16 mg/kg body weight. In some embodiments, the therapeutically effective amount of the FGFR1 ECD fusion molecule is a dose of about 8 mg/kg body weight. In some embodiments, the therapeutically effective amount of the FGFR1 ECD fusion molecule is a dose of about 16 mg/kg body weight. In some embodiments, the therapeutically effective amount of FGFR1 ECD fusion molecule is a dose of about 20 mg/kg body weight. In some embodiments, dosages may be administered twice a week, weekly, every other week, at a frequency between weekly and every other week, every three weeks, every four weeks, or every month.

In some embodiments, the dosage pack comprises an FGFR1 ECD and does not comprise the at least one additional therapeutic agent, e.g., docetaxel, paclitaxel, vincristine, carboplatin, cisplatin, oxaliplatin, doxorubicin, 5-fluorouracil (5-FU), leucovorin, pemetrexed, etoposide, topotecan, VEGF antagonist, anti-VEGF antibody, VEGF trap, bevacizumab, or sorafenib. In some embodiments, the dosage pack comprises an FGFR1 ECD fusion molecule and does not comprise the at least one additional therapeutic agent, e.g., docetaxel, paclitaxel, vincristine, carboplatin, cisplatin, oxaliplatin, doxorubicin, 5-fluorouracil (5-FU), leucovorin, pemetrexed, etoposide, topotecan, VEGF antagonist, anti-VEGF antibody, VEGF trap, bevacizumab, or sorafenib. In some embodiments, the dosage pack comprises at least one additional therapeutic agent, but does not comprise an FGFR1 ECD or an FGFR1 ECD fusion molecule. In some embodiments, the dosage pack comprises: (i) an FGFR1 ECD or an FGFR1 ECD fusion molecule, and (ii) at least one additional therapeutic agent. In some embodiments, the at least one additional therapeutic agent is docetaxel, paclitaxel, vincristine, carboplatin, cisplatin, oxaliplatin, doxorubicin, 5-fluorouracil (5-FU), leucovorin, pemetrexed, etoposide, topotecan, a VEGF antagonist, an anti-VEGF antibody, a VEGF trap, bevacizumab, or sorafenib. In some embodiments, the at least one additional therapeutic agent is docetaxel. In some embodiments, the at least one additional therapeutic agent is pemetrexed. In some embodiments, the at least one additional therapeutic agent is cisplatin. In some embodiments, the at least one additional therapeutic agent is paclitaxel. In some embodiments, the at least one additional therapeutic agent is 5-FU. In some embodiments, the at least one additional therapeutic agent is viscristine. In some embodiments, the at least one additional therapeutic agent is bevacizumab. In some embodiments, the at least one additional therapeutic agent is sorafenib. In some embodiments, the dosage pack comprises at least two additional therapeutic agents, but does not comprise an FGFR1 ECD or an FGFR1 ECD fusion molecule. In some embodiments, the at least two additional therapeutic agents are chosen from docetaxel, paclitaxel, vincristine, carboplatin, cisplatin, oxaliplatin, doxorubicin, 5-fluorouracil (5-FU), leucovorin, pemetrexed, etoposide, topotecan, a VEGF antagonist, an anti-VEGF antibody, a VEGF trap, bevacizumab, and sorafenib.

In some embodiments described above, the FGFR1 ECD or the FGFR1 ECD portion of the FGFR1 ECD fusion molecule comprises a sequence selected from SEQ ID NOs: 1 to 4. In some embodiments, at least one fusion partner is selected from an Fc, albumin, and polyethylene glycol. In some embodiments, at least one fusion partner is an Fc. In some embodiments, the Fc comprises an amino acid sequence selected from SEQ ID NOs: 8 to 10. In some embodiments, the FGFR1 ECD fusion molecule comprises a sequence selected from SEQ ID NO: 5 and SEQ ID NO: 6. In some embodiments, the FGFR1 ECD fusion molecule consists of a sequence selected from SEQ ID NO: 5 and SEQ ID NO: 6. In some embodiments, the at least one fusion partner is an Fc and polyethylene glycol. In some embodiments, the at least one fusion partners is polyethylene glycol.

In certain embodiments, the cancer is prostate cancer, breast cancer, colorectal cancer, lung cancer, endometrial cancer, head and neck cancer, laryngeal cancer, liver cancer, renal cancer glioblastoma or pancreatic cancer. In certain embodiments, the cancer is lung cancer. In certain embodiments, the cancer is renal cancer. In certain embodiments, the cancer is colon cancer. In certain embodiments, the cancer is breast cancer. In certain embodiments, the cancer is endometrial cancer. In certain embodiments, the cancer is prostate cancer.

Any embodiment described herein or any combination of additional therapeutic agents thereof applies to any and all methods of the invention described herein.

DETAILED DESCRIPTION

Figure 1:
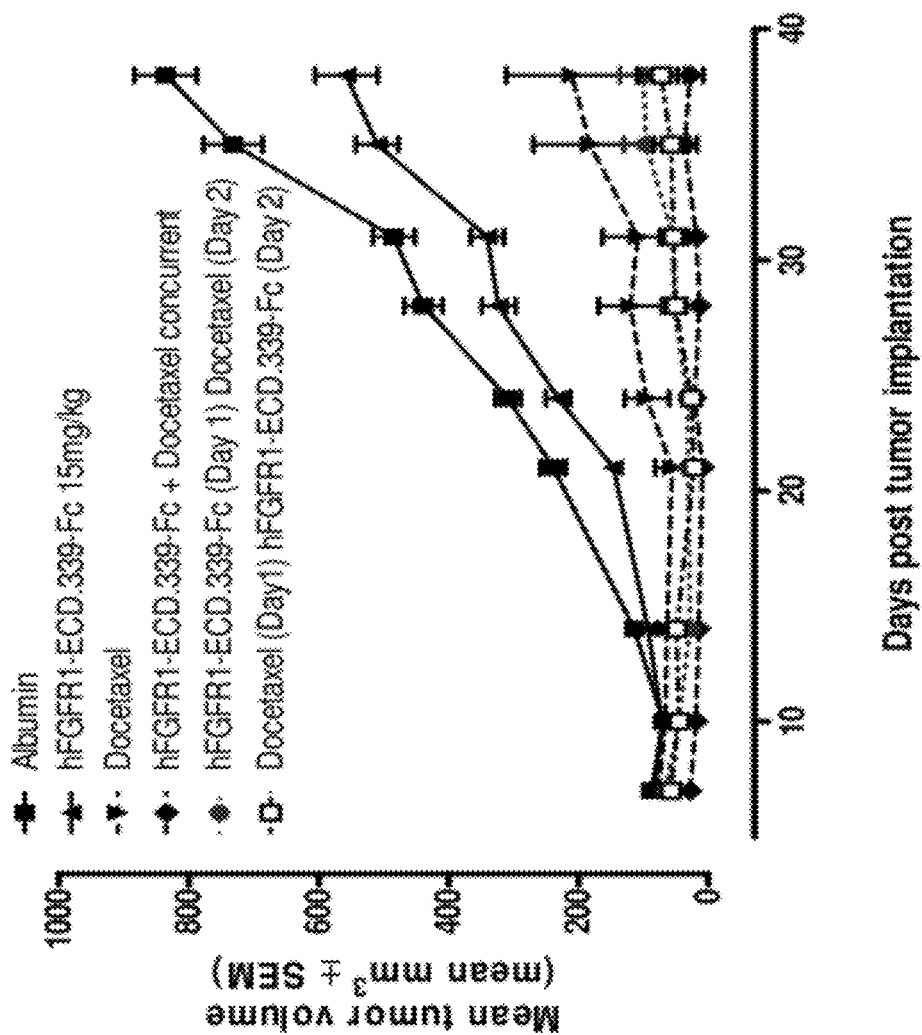
FIG. 1 shows the mean tumor volume in mice administered FGFR1-ECD.339-Fc alone, docetaxel alone, FGFR1-ECD.339-Fc and docetaxel sequentially, and FGFR1-ECD.339-Fc and docetaxel concurrently, as described in Example 1.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As used herein, all numbers are approximate, and may be varied to account for measurement error and the rounding of significant digits. The use of "about" before certain measured quantities includes variations due to sample impurities, measurement error, human error, and statistical variation, as well as the rounding of significant digits.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification. When a polypeptide "consists of" a particular amino acid sequence, it may still contain post-translational modifications, such as glycosylation and sialylation.

The term "FGFR1 extracellular domain" ("FGFR1 ECD") includes full-length FGFR1 ECDs, FGFR1 ECD fragments, and FGFR1 ECD variants. As used herein, the term "FGFR1 ECD" refers to an FGFR1 polypeptide that lacks the intracellular and transmembrane domains, with or without a signal peptide. In some embodiment, the FGFR1 ECD is a human full-length FGFR1 ECD having an amino acid sequence selected from SEQ ID NOs: 1 and 2. The term "full-length FGFR1 ECD", as used herein, refers to an FGFR1 ECD that extends to the last amino acid of the extracellular domain, and may or may not include an N-terminal signal peptide. As defined herein, the last amino acid of the full-length FGFR1 ECD is at position 353. Thus, a human full-length FGFR1 ECD may consist of the amino acid sequence corresponding to SEQ ID NO.: 2 (mature form) or to SEQ ID NO.: 1 (with the signal peptide). As used herein, the term "FGFR1 ECD fragment" refers to an FGFR1 ECD having one or more residues deleted from the N and/or C terminus of the full-length ECD and that retains the ability to bind to FGF-2. The FGFR1 ECD fragment may or may not include an N-terminal signal peptide. In some embodiments, the FGFR1 ECD fragment is a human FGFR1 ECD fragment having an amino acid sequence corresponding to SEQ ID NO.: 4 (mature form) or to SEQ ID NO.: 3 (with the signal peptide).

As used herein, the term "FGFR1 ECD variants" refers to FGFR1 ECDs that contain amino acid additions, deletions, and substitutions and that remain capable of binding to FGF-2. Such variants may be at least 90%, 92%, 95%, 97%, 98%, or 99% identical to the parent FGFR1 ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences. In some embodiments, an FGFR1 ECD variant is at least 95% identical to the sequence of SEQ ID NO: 4.

A polypeptide having an amino acid sequence at least, for example, 95% identical to a reference amino acid sequence of an FGFR1 ECD polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence.

These alterations of the reference sequence may occur at the N- or C-terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As used herein, the terms "hFGFR1-ECD.353" and "hFGFR1.353" may be used interchangeably to refer to the full-length human FGFR1 ECD corresponding to SEQ ID NO: 1 (with signal peptide) or to SEQ ID NO: 2 (without signal peptide; mature form).

As used herein, the terms "hFGFR1-ECD.339" and "hFGFR1.339" may be used interchangeably to refer to the human FGFR1 ECD corresponding to SEQ ID NO: 3 (with signal peptide) or to SEQ ID NO: 4 (without signal peptide; mature form).

Additional hFGFR1 ECDs are described, for example, in U.S. Pat. No. 7,678,890, which is incorporated by reference herein in its entirety for any purpose.

The term "FGFR1 ECD fusion molecule" refers to a molecule comprising an FGFR1 ECD, and one or more "fusion partners." In some embodiments, the FGFR1 ECD and the fusion partner are covalently linked ("fused"). If the fusion partner is also a polypeptide ("the fusion partner polypeptide"), the FGFR1 ECD and the fusion partner polypeptide may be part of a continuous amino acid sequence, and the fusion partner polypeptide may be linked to either the N terminus or the C terminus of the FGFR1 ECD. In such cases, the FGFR1 ECD and the fusion partner polypeptide may be translated as a single polypeptide from a coding sequence that encodes both the FGFR1 ECD and the fusion partner polypeptide (the "FGFR1 ECD fusion protein"). In some embodiments, the FGFR1 ECD and the fusion partner are covalently linked through other means, such as, for example, a chemical linkage other than a peptide bond. Many known methods of covalently linking polypeptides to other molecules (for example, fusion partners) may be used. In other embodiments, the FGFR1 ECD and the fusion partner may be fused through a "linker," which is comprised of at least one amino acid or chemical moiety.

In some embodiments, the FGFR1 ECD polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of some exemplary Fc domains are shown in SEQ ID NOs: 8 to 10. In some embodiments, an FGFR1 ECD fused to an Fc is referred to as an "hFGFR1 ECD-Fc." In some embodiments, the Fc domain is selected from an IgG1 Fc, an IgG2 Fc, an IgG3 Fc, and an IgG4 Fc.

As used herein, the terms "hFGFR1-ECD.339-Fc" and "hFGFR1.339-Fc" may be used interchangeably to refer to an amino acid sequence selected from SEQ ID NO: 6 (without signal peptide, mature form) and SEQ ID NO: 5 (with signal peptide). Nonlimiting exemplary cancers that may be treated with hFGFR1-ECD.339-Fc include, but are not limited to, non-small cell lung cancer, colon cancer, breast cancer, gastric cancer, head and neck cancer, prostate cancer, endometrial cancer, sarcoma, small cell lung cancer, ovarian cancer, Kaposi's sarcoma, Hodgkin's disease, leukemia, non-Hodgkin's lymphoma, neuroblastoma (brain cancer), rhabdomyosarcoma, Wilms' tumor, acute lymphoblastic leukemia, acute lymphoblastic leukemia, bladder cancer, testicular cancer, lymphomas, germ cell tumors, cancers of the colon and rectum, gastrointestinal cancers, thyroid cancer, multiple myeloma, pancreatic cancer, mesothelioma, malignant pleural mesothelioma, hematological/lymphatic cancers, malignant peritoneal mesothelioma, esophageal cancer, renal cell carcinoma, glioblastoma multiforme, and liver cancer.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides include, but are not limited to, FGFR1 signal peptides, such as, for example, the amino acid sequence of SEQ ID NO: 7. Exemplary signal peptides also include signal peptides from heterologous proteins. A "signal sequence" refers to a polynucleotide sequence that encodes a signal peptide. In some embodiments, an FGFR1 ECD lacks a signal peptide. In some embodiments, an FGFR1 ECD includes at least one signal peptide, which may be a native FGFR1 signal peptide or a heterologous signal peptide.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Exemplary mammalian cells include, but are not limited to, 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "anti-neoplastic composition" refers to a composition useful in treating cancer comprising at least one active therapeutic agent, e.g., an "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-VEGF antibodies (e.g., bevacizumab, AVASTIN®), anti-HER-2 antibodies (e.g., trastuzumab, HERCEPTIN®), anti-CD20 antibodies (e.g., rituximab, RITUXAN®), an epidermal growth factor receptor (EGFR) antagonist (e.g., a tyrosine kinase inhibitor), HER1/EGFR inhibitors (e.g., erlotinib (TARCEVA®), platelet derived growth factor inhibitors (e.g., GLEEVEC® (Imatinib Mesylate)), COX-2 inhibitors (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), pemetrexed (ALIMTA®); tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; amino]evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib, NEXAVAR®; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestins such as megestrol acetate and medroxyprogesterone acetate, estrogens such as diethylstilbestrol and premarin, and androgens/retinoids such as fluoxymesterone, all transretinoic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

An "angiogenic factor or agent" refers to a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family (VEGF-B, VEGF-C and VEGF-D), PlGF, PDGF family, fibroblast growth factor family (FGFs), TIE ligands (Angiopoietins), ephrins, delta-like ligand 4 (DLL4), del-1, fibroblast growth factors: acidic (aFGF) and basic (bFGF), follistatin, granulocyte colony-stimulating factor (G-CSF), hepatocyte growth factor (HGF)/scatter factor (SF), interleukin-8 (IL-8), leptin, midkine,neuropilins, placental growth factor, platelet-derived endothelial cell growth factor (PD-ECGF), platelet-derived growth factor, especially PDGF-BB or PDGFR-beta, pleiotrophin (PTN), progranulin, proliferin, transforming growth factor-alpha (TGF-alpha), transforming growth factor-beta (TGF-beta), tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., fusion proteins that binds to VEGF-A such as ZALTRAP™ (Aflibercept), antibodies to VEGF-A such as AVASTIN® (bevacizumab) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogenic agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12):1359-1364; Tonini et al. (2003) *Oncogene* 22:6549-6556 (e.g., Table 2 listing known anti-angiogenic factors); and, Sato (2003) *Int. J. Clin. dOncol.* 8:200-206 (e.g., Table 1 listing anti-angiogenic agents used in clinical trials).

"Docetaxel" refers to 1,7β,10β-trihydroxy-9-oxo-5β,20-epoxytax-11-ene-2α,4,13α-triyl 4-acetate 2-benzoate 13-{(2R,3S)-3-[tert-butoxycarbonyl)amino]-2-hydroxy-3-phenylpropanoate}, which, in some embodiments, may be sold under the brand name Taxotere®. In some embodiments, docetaxel is effective for treating at least one cancer selected from breast cancer and non small-cell lung cancer. Nonlimiting exemplary cancers that may be treated with docetaxel include breast cancer, colorectal cancer, lung cancer, ovarian cancer, prostate cancer, liver cancer, renal cancer, gastric cancer, head and neck cancers, and melanoma.

"Paclitaxel" refers to (2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate, which, in some embodiments, may be sold under the brand name TAXOL®. Nonlimiting exemplary cancers that may be treated with paclitaxel include breast cancer, lung cancer, and Kaposi's sarcoma.

"Carboplatin" refers to cis-diammine(cyclobutane-1,1-dicarboxylate-O,O')platinum(II), which, in some embodiments, may be sold under the brand name Paraplatin®. Nonlimiting exemplary cancers that may be treated with paclitaxel include, ovarian cancer, non-small cell lung cancer, testicular cancer, stomach cancer, and bladder cancer.

"Oxaliplatin" refers to [(1R,2R)-cyclohexane-1,2-diamine](ethanedioato-O,O')platinum(II), which, in some embodiments, may be sold under the brand name Eloxatin®. Nonlimiting exemplary cancers that may be treated with oxaliplatin include colorectal cancer, gastric cancer, and ovarian cancer.

"Cisplatin" refers to (SP-4-2)-diamminedichloridoplatinum. Nonlimiting exemplary cancers that may be treated with cisplatin include sarcomas, small cell lung cancer, ovarian cancer, bladder cancer, testicular cancer, lymphomas, and germ cell tumors.

"Vincristine" refers to methyl (1R,9R,10S,11R,12R,19R)-11-(acetyloxy)-12-ethyl-4-[(13S,15S,17S)-17-ethyl-17-hydroxy-13-(methoxycarbonyl)-1,11-diazatetracyclo [13.3.1.0$^{4,12}$.0$^{5,10}$]nonadeca-4(12),5,7,9-tetraen-13-yl]-8-formyl-10-hydroxy-5-methoxy-8,16-diazapentacyclo [10.6.1.0$^{1,9}$.0$^{2,7}$.0$^{16,19}$]nonadeca-2,4,6,13-tetraene-10-carboxylate, which, in some embodiments, may be sold under the brand name Vincasar®. Nonlimiting exemplary cancers that may be treated with vincristine include Hodgkin's disease, leukemia, non-Hodgkin's lymphoma, neuroblastoma, rhabdomyosarcoma, acute lymphoblastic leukemia, and Wilms' tumor.

"Pemetrexed" refers to (S)-2-[4-[2-(4-amino-2-oxo-3,5,7-triazabicyclo[4.3.0]nona-3,8,10-trien-9-yl)ethyl]benzoyl] aminopentanedioic acid, which, in some embodiments, may be sold under the brand name Alimta®. Nonlimiting exemplary cancers that may be treated with pemetrexed include non small cell lung cancer, mesothelioma, and esophageal cancer.

"Doxorubicin" refers to (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, which, in some embodiments, may be sold under the brand name Adriamycin®. Nonlimiting exemplary cancers that may be treated with doxorubicin include bladder cancer, breast cancer, lung cancer, ovarian cancer, stomach cancer, thyroid cancer, soft tissue sarcoma, multiple myeloma, Hodgkin's disease, leukemia, non-Hodgkin's lymphoma, neuroblastoma, sarcoma, and Wilms' tumor.

"5-FU" and "5-fluorouracil" refer to 5-fluoro-1H-pyrimidine-2,4-dione, which, in some embodiments, may be sold under the brand name Adrucil®. Nonlimiting exemplary cancers that may be treated with 5-FU include colorectal cancer, pancreatic cancer, breast cancer, esophageal cancer, gastric cancer, head and neck cancer, hepatoma, and ovarian cancer.

"Leucovorin" is also known as folinic acid, and refers to (S)-2-[4-[(2-amino-5-formyl-4-oxo-5,6,7,8-tetrahydro-1H-pteridin-6-yl)methylamino]benzoyl]aminopentanedioic acid. In some embodiments, leucovorin is administered with 5-fluorouracil.

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) Science 246:1306, and Houck et al. (1991) Mol. Endocrin, 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)," "VEGF-A$_{109}$" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies, VEGF receptor antagonists such as small molecule inhibitors of the VEGFR tyrosine kinases, and immunoadhesins that binds to VEGF such as VEGF trap (e.g., aflibercept). The term "VEGF antagonist," as used herein, specifically includes molecules, including antibodies, antibody fragments, other binding polypeptides, peptides, and non-peptide small molecules, that bind to VEGF and are capable of neutralizing, blocking, inhibiting, abrogating, reducing or interfering with VEGF activities. Thus, the term "VEGF activities" specifically includes VEGF mediated biological activities of VEGF.

The term "VEGF trap" as used herein means a protein, such as a fusion molecule, that binds to VEGF and is capable of neutralizing, blocking, inhibiting, abrogating, reducing or interfering with VEGF activities. An example of a VEGF trap is aflibercept.

The term "anti-VEGF antibody" or "an antibody that binds to VEGF" refers to an antibody that is capable of binding to VEGF with sufficient affinity and specificity that the antibody is useful as a diagnostic and/or therapeutic agent in targeting VEGF. Anti-VEGF antibodies suppress the growth of a variety of human tumor cell lines in nude mice (Kim et al., Nature 362:841-844 (1993); Warren et al., J. Clin. Invest. 95:1789-1797 (1995); Borgström et al., Cancer Res. 56:4032-4039 (1996); Melnyk et al., Cancer Res. 56:921-924 (1996)) and also inhibit intraocular angiogenesis in models of ischemic retinal disorders. Adamis et al., Arch. Ophthalmol. 114:66-71 (1996). For example, the anti-VEGF antibody can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al., Journal of Immunological Methods 288:149-164 (2004); and WO2005012359. The antibody selected will normally have a sufficiently strong binding affinity for VEGF. For example, the antibody may bind hVEGF with a $K_d$ value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. The antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B, VEGF-C, VEGF-D or VEGF-E, nor other growth factors such as PlGF, PDGF or bFGF.

In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody (see Presta et al. (1997) *Cancer Res.* 57:4593-4599), including but not limited to the antibody known as "bevacizumab" also known as "rhuMAb VEGF" or "AVASTIN®." AVASTIN® is presently commercially available. Nonlimiting exemplary cancers that may be treated with bevacizumab include non-small cell lung cancer, colorectal cancer, breast cancer, renal cancer, ovarian cancer, glioblastoma multiforme, pediatric osteosarcoma, gastric cancer and pancreatic cancer. Bevacizumab comprises mutated human $IgG_1$ framework regions and antigen-binding complementarity-determining regions from the murine antibody A.4.6.1 that blocks binding of human VEGF to its receptors. Bevacizumab and other humanized anti-VEGF antibodies are further described in U.S. Pat. Nos. 6,884,879, and 7,169,901. Additional anti-VEGF antibodies are described in PCT Application Publication Nos. WO2005/012359 and WO2009/073160; U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004).

The terms "subject" and "patient" are used interchangeably herein to refer to a mammal. In some embodiments, the subject or patient is a human. In other embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

"Treatment," as used herein, includes any administration or application of a therapeutic for condition in a mammal, including a human, and includes inhibiting the condition or progression of the condition, inhibiting or slowing the condition or its progression, arresting its development, partially or fully relieving the condition, or curing the condition, for example, by causing regression, or restoring or repairing a lost, missing, or defective function; or stimulating an inefficient process. In some embodiments, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "effective amount" or "therapeutically effective amount" of a molecule or a combination of molecules means an amount that is sufficient to treat a condition and/or to inhibit growth of tumor cells in at least a subset of subjects when given alone or in combination with other treatments. In certain embodiments, a therapeutically effective amount refers to an amount effective, at dosages and for periods of time necessary, to achieve the desired therapeutic or prophylactic result. A therapeutically effective amount of FGFR1 fusion protein of the invention may vary according to factors such as the disease state, age, sex, and weight of the individual, and the ability of FGFR1 fusion protein to elicit a desired response in the individual. A therapeutically effective amount is also one in which any toxic or detrimental effects of the FGFR1 fusion proteins are outweighed by the therapeutically beneficial effects. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth; allow for treatment of the tumor, and/or relieve to some extent one or more of the symptoms associated with the disorder. To the extent the drug may prevent growth and/or kill existing cancer cells, it may be cytostatic and/or cytotoxic.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "inhibition" or "inhibit" refer to a decrease or cessation of any phenotypic characteristic or to the decrease or cessation in the incidence, degree, or likelihood of that characteristic. Nonlimiting exemplary inhibition includes inhibition of tumor growth.

Herein, "concurrent" dosing refers to the administration of two therapeutic molecules within an eight hour time period. In some embodiments, two therapeutic molecules are administered at the same time. Two therapeutic molecules are considered to be administered at the same time (i.e. simultaneously) if at least a portion of a dose of each therapeutic molecule is administered within 1 hour. Two therapeutic molecules are administered concurrently if at least one dose is administered concurrently, even if one or more other doses are not administered concurrently. In some embodiments, concurrent administration includes a dosing regimen when the administration of one or more therapeutic molecule(s) continues after discontinuing the administration of one or more other therapeutic molecules(s).

Administration "in combination with" one or more further therapeutic agents includes concurrent (including simultaneous) and consecutive (i.e., sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Therapeutic Compositions and Methods

Methods of Treating Cancer Using FGFR1 ECDs and/or FGFR1 ECD Fusion Molecules in Combination with Other Therapeutic Agents The invention features the combination of a fibroblast growth factor receptor 1 (FGFR1) extracellular domain (ECD) or FGFR1 ECD fusion molecule with one or more additional anti-cancer therapies and the use of such combinations in cancer treatment. Examples of the additional anti-cancer therapies include, without limitation, surgery, radiation therapy (radiotherapy), biotherapy, immunotherapy, and chemotherapy or a combination of these therapies. In addition, cytotoxic agents, anti-angiogenic and anti-proliferative agents can be used in combination with the FGFR1 ECD or FGFR1 ECD fusion molecule. In certain aspects of any of the methods and uses, the invention provides treating cancer, by administering therapeutically effective amounts of an FGFR1 ECD and/or FGFR1 ECD fusion molecule and one or more chemotherapeutic agents to a subject diagnosed with or suffering from a previously untreated cancer. A variety of chemotherapeutic agents may be used in the combined treatment methods and uses of the invention. An exemplary and non-limiting list of chemotherapeutic agents contemplated is provided herein under "Definitions" and in the "Summary of the Invention." In another aspect, the invention provides treating cancer, by administering therapeutically effective amounts of an FGFR1 ECD and/or FGFR1 ECD fusion molecule and one or more anti-angiogenic agent(s) to a subject diagnosed with a previously untreated cancer. In another aspect, the invention provides treating cancer, by administering therapeutically effective amounts of an FGFR1 ECD and/or FGFR1 ECD fusion molecule and one or more VEGF antagonists to a subject diagnosed with a previously untreated cancer. In yet another aspect, the invention provides treating cancer, by administering therapeutically effective amounts of an FGFR1 ECD and/or FGFR1 ECD fusion molecule and one or more VEGF antagonists in combination with one or more chemotherapeutic agents to a subject diagnosed with a previously untreated cancer. In some embodiments, the one or more VEGF antagonists are anti-VEGF antibodies and/or VEGF traps.

In one example, methods of treating cancer comprising administering to a subject an FGFR1 ECD and/or FGFR1 ECD fusion molecule in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a VEGF antagonist, an anti-VEGF antibody, a VEGF trap, and bevacizumab are provided. In some embodiments, methods of treating cancer comprising administering to a subject an FGFR1 ECD and/or FGFR1 ECD fusion molecule and docetaxel are provided. In some embodiments, methods of treating cancer comprising administering to a subject an FGFR1 ECD and/or FGFR1 ECD fusion molecule and pemetrexed are provided. In some embodiments, methods of treating cancer comprising administering to a subject an FGFR1 ECD and/or FGFR1 ECD fusion molecule and paclitaxel are provided. In some embodiments, methods of treating cancer comprising administering to a subject an FGFR1 ECD and/or FGFR1 ECD fusion molecule and cisplatin are provided. In some embodiments, methods of treating cancer comprising administering to a subject an FGFR1 ECD and/or FGFR1 ECD fusion molecule and vincristine are provided. In some embodiments, methods of treating cancer comprising administering to a subject an FGFR1 ECD and/or FGFR1 ECD fusion molecule and 5-FU are provided. In some embodiments, methods of treating cancer comprising administering to a subject an FGFR1 ECD and/or FGFR1 ECD fusion molecule and etoposide are provided. In some embodiments, methods of treating cancer comprising administering to a subject an FGFR1 ECD and/or FGFR1 ECD fusion molecule and topotecan are provided. In some embodiments, methods of treating cancer comprising administering to a subject an FGFR1 ECD and/or FGFR1 ECD fusion molecule and a VEGF antagonist are provided. In some embodiments, methods of treating cancer comprising administering to a subject an FGFR1 ECD and/or FGFR1 ECD fusion molecule and an anti-VEGF antibody are provided. In some embodiments, methods of treating cancer comprising administering to a subject an FGFR1 ECD and/or FGFR1 ECD fusion molecule and a VEGF trap are provided. In some embodiments, methods of treating cancer comprising administering to a subject an FGFR1 ECD and/or FGFR1 ECD fusion molecule and bevacizumab are provided. In some embodiments, at least one dose of the FGFR1 ECD and/or FGFR1 ECD fusion molecule and at least one dose of at least one additional therapeutic agent are administered concurrently. In some embodiments, at least one dose of the FGFR1 ECD and/or FGFR1 ECD fusion molecule and at least one dose of at least one additional therapeutic agent are administered at the same time (i.e., simultaneously). In some embodiments, at least one dose of the FGFR1 ECD and/or FGFR1 ECD fusion molecule and at least one dose of at least two additional therapeutic agents are administered concurrently or simultaneously. In some embodiments, at least one dose of the FGFR1 ECD and/or FGFR1 ECD fusion molecule and at least one dose of at least three additional therapeutic agents are administered concurrently or simultaneously. In another example, methods of treating cancer comprising administering to a subject an FGFR1-ECD.339-Fc in combination with at least one additional therapeutic agent selected from docetaxel, paclitaxel, vincristine, carboplatin, cisplatin, oxaliplatin, doxorubicin, 5-fluorouracil (5-FU), leucovorin, pemetrexed, and etoposide, topotecan, a VEGF antagonist, an anti-VEGF antibody, a VEGF trap, sorafenib, and bevacizumab are provided. In some embodiments, methods of treating cancer comprising administering to a subject an FGFR1-ECD.339-Fc and docetaxel are provided. In some embodiments, at least one dose of an FGFR1-ECD.339-Fc and at least one dose of at least one additional therapeutic agent are administered concurrently. In some embodiments, at least one dose of an FGFR1-ECD.339-Fc and at least one dose of at least one additional therapeutic agent are administered at the same time.

Pharmaceutical compositions comprising FGFR1 ECD and/or FGFR1 ECD fusion molecules (e.g., FGFR1-ECD.339-Fc) are administered in a therapeutically effective amount for the specific indication. The therapeutically effective amount is typically dependent on the weight of the subject being treated, his or her physical or health condition, the extensiveness of the condition to be treated, and/or the age of the subject being treated. In general, an FGFR1 ECD and/or FGFR1 ECD fusion molecule (e.g., FGFR1-ECD.339-Fc) is to be administered in an amount in the range of about 50 µg/kg body weight to about 100 mg/kg body weight per dose.

Optionally, the FGFR1 ECD and/or FGFR1 ECD fusion molecule (e.g., FGFR1-ECD.339-Fc) can be administered in an amount in the range of about 100 µg/kg body weight to about 30 mg/kg body weight per dose. Further optionally, the FGFR1 ECD and/or FGFR1 ECD fusion molecule (e.g., FGFR1-ECD.339-Fc) can be administered in an amount in the range of about 0.5 mg/kg body weight to about 20 mg/kg body weight per dose. In certain embodiments, the FGFR1 ECD and/or FGFR1 ECD fusion molecule (e.g., FGFR1-ECD.339-Fc) is administered at a dose of about 8 mg/kg body weight to about 20 mg/kg body weight. In some embodiments, the FGFR1 ECD and/or FGFR1 ECD fusion molecule (e.g., FGFR1-ECD.339-Fc) is administered at a dose of about 8 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, or about 20 mg/kg body weight. The FGFR1 ECD and/or FGFR1 ECD fusion molecules may also be administered at ranges from one of the above doses to another. In some embodiments, dosages may be administered twice a week, weekly, every other week, at a frequency between weekly and every other week, every three weeks, every four weeks, or every month.

In certain embodiments, dosages of the FGFR1 ECD and/or FGFR1 ECD fusion molecules can be calculated in two ways depending on the extinction coefficient (EC) used. The extinction coefficient differs depending on whether the glycosylation of the protein is taken into account. In one embodiment, the extinction coefficient based on the amino acid composition of FGFR1-ECD.339-Fc, for example, is 1.42 mL/mg*cm. In another embodiment, when the carbohydrate portion as well as the amino acid portion of FGFR1-ECD.339-Fc is accounted for, the extinction coefficient is 1.11 mL/mg*cm. Calculation of the FGFR1-ECD.339-Fc dose using an EC of 1.11 mL/mg*cm increases the calculated dose by 28%, as shown in Table 1. Although the doses calculated using the two extinction coefficients are different, the molar concentrations, or the actual amounts of drug administered, are identical. Unless otherwise noted, the doses disclosed herein are each calculated using the extinction coefficient that does not take account of glycosylation. How these dosages compare to those calculated using the extinction coefficient that takes account of glycosylation for FGFR1-ECD.339-Fc is shown in Table 1. As can be seen from Table 1, a dosage of about 8 mg/kg (e.g., 7.8 and 8.0) using an EC of 1.42 mL/mg*cm herein corresponds to a dosage of about 10 mg/kg (e.g. 10.0 and 10.2) when calculated using an EC of 1.11 mL/mg*cm. A dosage of about 16 mg/kg (e.g. 15.6 and 16.0 mg/kg) using an EC of 1.42 mL/mg*cm herein corresponds to a dosage of about 20 mg/kg (e.g. 20.0 and 20.5) when calculated using an EC of 1.11 mL/mg*cm. As noted in the "Definitions" section above, measured numbers provided herein are approximate and encompass values having additional significant digits that are rounded off. For instance, 8 mg/kg encompasses values with two significant digits such as 7.6, 7.8, 8.0, 8.2, 8.4, and 8.45, each of which round to 8. Likewise, a value such as 16 mg/kg encompasses values with three significant digits that round to 16, such as, for example 15.6 and 16.0.

TABLE 1

Conversion of FGFR1-ECD.339-FC Dose

| Dose[a] EC = 1.42 mL/mg * cm | Dose[a] EC = 1.11 mL/mg * cm |
|---|---|
| 0.5 | 0.6 |
| 0.75 | 1.0 |
| 1.0 | 1.3 |
| 2.0 | 2.6 |
| 3.0 | 3.8 |
| 4.0 | 5.1 |
| 5.0 | 6.4 |
| 6.0 | 7.7 |
| 7.0 | 9.0 |
| 7.8 | 10.0 |
| 8.0 | 10.2 |
| 9.0 | 11.5 |
| 10.0 | 12.8 |
| 11.0 | 14.1 |
| 12.0 | 15.4 |
| 13.0 | 16.6 |
| 14.0 | 17.9 |
| 15.0 | 19.2 |
| 15.6 | 20.0 |
| 16.0 | 20.5 |
| 17.0 | 21.8 |
| 18.0 | 23.0 |
| 19.0 | 24.3 |
| 20.0 | 25.6 |
| 30.0 | 38.4 |

[a]Doses shown in mg/kg.

The pharmaceutical compositions comprising FGFR1 ECDs, FGFR1 ECD fusion molecules, and/or at least one additional therapeutic agent can be administered as needed to subjects. In certain embodiments, an effective dose of a therapeutic molecule is administered to a subject one or more times. In various embodiments, an effective dose of a therapeutic molecule is administered to the subject at least once every two months, at least once a month, at least twice a month, once a week, twice a week, or three times a week. In various embodiments, an effective dose of a therapeutic molecule is administered to the subject for at least a week, at least a month, at least three months, at least six months, or at least a year.

In certain embodiments, the combined administration of an FGFR1 ECDs, FGFR1 ECD fusion molecule and at least one additional therapeutic agent includes concurrent administration, including simultaneous administration, using separate formulations or a single pharmaceutical formulation, as well as consecutive administration in any order. Optionally there is a time period while both (or all) active agents simultaneously exert their biological activities. Therapeutically effective amounts of therapeutic agents administered in combination with the FGFR1 ECD and/or FGFR1 ECD fusion molecule (e.g., FGFR1-ECD.339-Fc) will be at the physician's or veterinarian's discretion. Dosage administration and adjustment is done to achieve maximal management of the conditions to be treated. The dose will additionally depend on such factors as the type of therapeutic agent to be used, the specific patient being treated, the stage of the disease, and the desired aggressiveness of the treatment regime.

In certain embodiments, a patient is treated with a combination of the FGFR1 ECD and/or FGFR1 ECD fusion molecule (e.g., FGFR1-ECD.339-Fc) and a VEGF antagonist. In some embodiments, the VEGF antagonist is a VEGF trap (e.g., aflibercept). In some embodiments, the VEGF antagonist is an anti-VEGF antibody. In some embodiments, the VEGF antibody is bevacizumab. One exemplary dosage of bevacizumab is in the range from about 0.05 mg/kg to about 20 mg/kg. Thus, one or more doses of about 0.5 mg/kg, 2.0 mg/kg, 4.0 mg/kg, 7.5 mg/kg, 10 mg/kg or 15 mg/kg (or any combination thereof) may be administered to the patient. Such doses may be administered intermittently, e.g., every week, every two, or every three weeks.

In some embodiments, the FGFR1 ECD and/or FGFR1 ECD fusion molecule (e.g., FGFR1-ECD.339-Fc) is administered in combination with another therapeutic agent, such as chemotherapeutic agent or anti-angiogenic agent, at the recommended or prescribed dosage and/or frequency of the therapeutic agent.

Routes of Administration and Carriers

In some embodiments, an FGFR1 ECD and/or FGFR1 ECD fusion molecule can be administered intravenously and/or subcutaneously. In some embodiments, an FGFR1 ECD and/or FGFR1 ECD fusion molecule can be administered by another route, such as intra-arterial, parenteral, intranasal, intramuscular, intracardiac, intraventricular, intratracheal, buccal, rectal, intraperitoneal, intradermal, topical, transdermal, or intrathecal, or otherwise by implantation or inhalation. In various embodiments, at least one additional therapeutic agent can be administered in vivo by a variety of routes, including intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. Each of the subject compositions can be formulated alone or in combination into preparations in solid, semi-solid, liquid, or gaseous forms, such as tablets, capsules, powders, granules, ointments, solutions, suppositories, enemas, injections, inhalants, and aerosols.

In various embodiments, compositions comprising an FGFR1 ECD, FGFR1 ECD fusion molecule, and/or at least one additional therapeutic agent are provided in formulation with pharmaceutically acceptable carriers, a wide variety of which are known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof. In some embodiments, a therapeutic agent is formulated as the brand-name drug indicated above in the Definitions section, or a generic equivalent. In some embodiments, docetaxel is formulated as Taxotere® (Sanofi Aventis) or a generic equivalent.

In various embodiments, compositions comprising FGFR1 ECDs, FGFR1 ECD fusion molecules, and/or at least one additional therapeutic agent can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical dosage packs comprising one or more containers, each containing one or more doses of an FGFR1 ECD, an FGFR1 ECD fusion molecule, and/or at least one additional therapeutic agent are also provided. In some embodiments, the dosage packs contain an FGFR1 ECD and/or FGFR1 ECD fusion molecule but do not contain any additional therapeutic agent such as docetaxel, paclitaxel, vincristine, carboplatin, cisplatin, oxaliplatin, doxorubicin, 5-fluorouracil (5-FU), leucovorin, pemetrexed, etoposide, topotecan, sorafenib, a VEGF antagonist, an anti-VEGF antibody, a VEGF trap, or bevacizumab. In other embodiments, the dosage packs contain at least one additional therapeutic agent but do not contain the FGFR1 ECD or FGFR1 ECD fusion molecule. In other embodiments, the dosage packs contain an FGFR1 ECD and/or FGFR1 ECD fusion molecule and at least one additional therapeutic agent, wherein the FGFR1 ECD and/or FGFR1 ECD fusion molecule is in a separate container from the at least one additional therapeutic agent. In other embodiments, the FGFR1 ECD and/or FGFR1 ECD fusion molecule is in the same container as the at least one additional therapeutic agent. In certain embodiments where two or more additional therapeutic agents are supplied, the two or more additional therapeutic agents may be in separate or in the same containers. In certain embodiments, a unit dosage is provided wherein the unit dosage contains a predetermined amount of a composition comprising an FGFR1 ECD, an FGFR1 ECD fusion molecule, and/or at least one additional therapeutic agent with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, a composition comprises one or more substances that inhibit protein aggregation, including, but not limited to, sucrose and arginine. In certain embodiments, a composition of the invention comprises heparin and/or a proteoglycan. In some embodiments, a dosage pack comprises an FGFR1 ECD and/or an FGFR1 ECD fusion molecule and/or at least one additional therapeutic agent selected from docetaxel, paclitaxel, vincristine, carboplatin, cisplatin, oxaliplatin, doxorubicin, 5-fluorouracil (5-FU), leucovorin, pemetrexed, etoposide, topotecan, sorafenib, a VEGF antagonist, an anti-VEGF antibody, a VEGF trap, and bevacizumab.

In some embodiments, a dosage pack further comprises instructions for administering an FGFR1 ECD and/or an FGFR1 ECD fusion molecule with at least one additional therapeutic agent to a patient. In some embodiments, the instructions indicate that at least one dose of the FGFR1 ECD and/or the FGFR1 ECD fusion molecule should be administered concurrently with the at least one additional therapeutic agent. In some embodiments, the instructions indicate that at least one dose of the FGFR1 ECD and/or the FGFR1 ECD fusion molecule should be administered at the same time as the at least one additional therapeutic agent.

The term "instructions," as used herein includes, but is not limited to, labels, package inserts, instructions available in electronic form such as on a computer readable medium (e.g., a diskette, compact disk, or DVD), instructions available remotely such as over the internet, etc. A dosage pack is considered to include the instructions when the dosage pack provides access to the instructions, a link to the instructions (such as a uniform resource locator, or url), or other mechanism for obtaining a copy of the instructions (such as a return reply card, a physical address from which instructions may be requested, an e-mail address from which instructions may be requested, a phone number that may be called to obtain instructions, etc.).

FGFR1 ECDs and FGFR1 ECD Fusion Molecules

Nonlimiting exemplary FGFR1 ECDs include full-length FGFR1 ECDs, FGFR1 ECD fragments, and FGFR1 ECD variants. FGFR1 ECDs may include or lack a signal peptide. Exemplary FGFR1 ECDs include, but are not limited to, FGFR1 ECDs having amino acid sequences selected from SEQ ID NOs.: 1, 2, 3, and 4.

Non-limiting exemplary FGFR1 ECD fragments include human FGFR1 ECD ending at amino acid 339 (counting from the first amino acid of the mature form, without the signal peptide). In some embodiments, an FGFR1 ECD fragment ends at an amino acid between amino acid 339 and amino acid 360 (counting from the first amino acid of the mature form, without the signal peptide). Exemplary FGFR1 ECD fragments include, but are not limited to, FGFR1 ECD fragments having amino acid sequences selected from SEQ ID NOs.: 3 and 4.

In some embodiments, an FGFR1 ECD comprises a sequence selected from SEQ ID NOs: 1 to 4. In some embodiments, an FGFR1 ECD consists of a sequence selected from SEQ ID NOs: 1 to 4. When an FGFR1 ECD "consists of" a sequence selected from SEQ ID NOs: 1 to 4, the FGFR1 ECD may or may not contain various post-translational modifications, such as glycosylation and sialylation. In other words, when an FGFR1 ECD consists of a particular amino acid sequence, it does not contain additional amino acids in the contiguous amino acid sequence, but may contain modifications to amino acid side chains, the N-terminal amino group, and/or the C-terminal carboxy group.

In some embodiments, an FGFR1 ECD fusion molecule comprises a signal peptide. In some embodiments, an FGFR1 ECD fusion molecule lacks a signal peptide. In some embodiments, the FGFR1 ECD portion of an FGFR1 ECD fusion molecule comprises a sequence selected from SEQ ID NOs: 1 to 4. In some embodiments, the FGFR1 ECD portion of an FGFR1 ECD fusion molecule consists of a sequence selected from SEQ ID NOs: 1 to 4. When an FGFR1 ECD portion of an FGFR1 ECD fusion molecule "consists of" a sequence selected from SEQ ID NOs: 1 to 4, the FGFR1 ECD portion of an FGFR1 ECD fusion molecule may or may not contain various post-translational modifications, such as glycosylation and sialylation. In other words, when an FGFR1 ECD portion of an FGFR1 ECD fusion molecule consists of a particular amino acid sequence, it does not contain additional amino acids from FGFR1 in the contiguous amino acid sequence, but may contain modifications to amino acid side chains, the N-terminal amino group, and/or the C-terminal carboxy group. Further, because the FGFR1 ECD is linked to a fusion molecule, there may be additional amino acids at the N- and/or C-terminus of the FGFR1 ECD, but those amino acids are not from the FGFR1 sequence, but may be from, for example, a linker sequence, or a fusion partner sequence.

In some embodiments, the fusion partner portion of an FGFR1 ECD fusion molecule is selected from Fc, albumin, and polyethylene glycol. Nonlimiting exemplary fusion partners are discussed herein.

The inventors have found that administration of an FGFR1 ECD and/or an FGFR1 ECD fusion molecule and at least one additional therapeutic agent selected from docetaxel, paclitaxel, vincristine, carboplatin, cisplatin, oxaliplatin, doxorubicin, 5-fluorouracil (5-FU), leucovorin, pemetrexed, sorafenib, etoposide, topotecan, a vascular epithelial growth factor (VEGF) agonist, a VEGF trap, an anti-VEGF antibody, and bevacizumab is useful for treating cancer. In some embodiments, an FGFR1 ECD and/or an FGFR1 ECD fusion molecule is administered with docetaxel.

Fusion Partners and Conjugates

As discussed herein, an FGFR1 ECD may be combined with at least one fusion partner, resulting in an FGFR1 ECD fusion molecule. These fusion partners may facilitate purification, and the FGFR1 ECD fusion molecules may show an increased half-life in vivo. Suitable fusion partners of an FGFR1 ECD include, for example, polymers, such as water soluble polymers, the constant domain of immunoglobulins; all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179. Nonlimiting exemplary FGFR1 ECD fusion molecules are described, e.g., in U.S. Pat. No. 7,678,890.

An FGFR1 ECD fusion molecule may be prepared by attaching polyaminoacids or branch point amino acids to the FGFR1 ECD. For example, the polyaminoacid may be a carrier protein that serves to increase the circulation half life of the FGFR1 ECD (in addition to the advantages achieved via a fusion molecule). For the therapeutic purpose of the present invention, such polyaminoacids should ideally be those that have or do not create neutralizing antigenic responses, or other adverse responses. Such polyaminoacids may be chosen from serum album (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N terminus or C terminus, or other places in between, and also may be connected by a chemical linker moiety to the selected molecule.

Polymers

Polymers, for example, water soluble polymers, may be useful as fusion partners to reduce precipitation of the FGFR1 ECD fusion molecule in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-($C_1$-$C_{10}$) alkoxy- or aryloxy-polyethylene glycol. Polyethylene glycol propionaldehyde may have advantages in manufacturing due to its stability in water.

Polymers used herein, for example water soluble polymers, may be of any molecular weight and may be branched or unbranched. In some embodiments, the polymers have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on an FGFR1 ECD.

Polymers employed in the present invention are typically attached to an FGFR1 ECD with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha ($\alpha$) or epsilon ($\epsilon$) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to an FGFR1 ECD via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting an FGFR1 ECD with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-, tri-, etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified FGFR1 ECD. One may select a polymer by molecular weight, branching, etc., the proportion of polymers to FGFR1 ECD molecules in the reaction mix, the type of reaction to be performed, and the method of obtaining the selected N-terminal chemically modified FGFR1 ECD. The method of obtaining the N-terminal chemically modified FGFR1 ECD preparation (separating this moiety from other monoderivatized moieties if necessary) may be by purification of the N-terminal chemically modified FGFR1 ECD material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N terminus with a carbonyl group-containing polymer is achieved. For example, one may selectively attach a polymer to the N terminus of the protein by performing the reaction at a pH that allows one to take advantage of the pKa differences between the $\epsilon$-amino group of the lysine residues and that of the $\alpha$-amino group of the N-terminal residue of the protein. By such selective derivatization, attachment of a polymer to a protein is controlled: the conjugation with the polymer takes place predominantly at the N terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized FGFR1 ECD to include mono- or poly-(e.g., 2-4) PEG moieties. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result.

There are a number of PEG attachment methods known in the art. See, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; WO 95/34326; and the other publications cited herein that relate to pegylation.

Pegylation may be carried out, e.g., via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the $\alpha$- or $\epsilon$-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with an FGFR1 ECD. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.,* 5:133-140 (1994). Reaction conditions may be selected from any of those currently known or those subsequently developed, but should avoid conditions such as temperature, solvent, and pH that would inactivate the polypeptide to be modified.

Pegylation by acylation will generally result in a polypegylated protein. The connecting linkage may be an amide. The resulting product may be substantially only (e.g., >95%) mono-, di-, or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography, and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono $C_1$-$C_{10}$ alkoxy or aryloxy derivatives thereof, see for example, U.S. Pat. No. 5,252,714.

Markers

Moreover, FGFR1 ECDs of the present invention may be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., Cell 37:767 (1984)). Any of these above fusions may be engineered using the FGFR1 ECDs described herein.

Oligomerization Domain Fusion Partners

In various embodiments, oligomerization offers some functional advantages to a fusion protein, including, but not limited to, multivalency, increased binding strength, and the combined function of different domains. Accordingly, in some embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Exemplary coiled-coil polypeptide fusion partners include, but are not limited to, the tetranectin coiled-coil domain; the coiled-coil domain of cartilage oligomeric matrix protein; angiopoietin coiled-coil domains; and leucine zipper domains. Exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In some embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Additional exemplary Fc fusion partners include, but are not limited to, human IgA and IgM. In some embodiments, an Fc fusion partner comprises a C237S mutation, for example, in an IgG1 (see, for example, SEQ ID NO: 8). In some embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 8 to 10.

Albumin Fusion Partners and Albumin-binding Molecule Fusion Partners

In some embodiments, a fusion partner is an albumin. Exemplary albumins include, but are not limited to, human serum album (HSA) and fragments of HSA that are capable of increasing the serum half-life or bioavailability of the polypeptide to which they are fused. In some embodiments, a fusion partner is an albumin-binding molecule, such as, for example, a peptide that binds albumin or a molecule that conjugates with a lipid or other molecule that binds albumin. In some embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N terminus or the C terminus of the FGFR1 ECD. The attachment may also occur at a location within the FGFR1 ECD other than the N terminus or the C terminus, for example, through an amino acid side chain (such as, for example, the side chain of cysteine, lysine, serine, or threonine).

In either covalent or non-covalent attachment embodiments, a linker may be included between the fusion partner and the FGFR1 ECD. Such linkers may be comprised of at least one amino acid or chemical moiety. Exemplary methods of covalently attaching a fusion partner to an FGFR1 ECD include, but are not limited to, translation of the fusion partner and the FGFR1 ECD as a single amino acid sequence and chemical attachment of the fusion partner to the FGFR1 ECD. When the fusion partner and an FGFR1 ECD are translated as single amino acid sequence, additional amino acids may be included between the fusion partner and the FGFR1 ECD as a linker. In some embodiments, the linker is selected based on the polynucleotide sequence that encodes it, to facilitate cloning the fusion partner and/or FGFR1 ECD into a single expression construct (for example, a polynucleotide containing a particular restriction site may be placed between the polynucleotide encoding the fusion partner and the polynucleotide encoding the FGFR1 ECD, wherein the polynucleotide containing the restriction site encodes a short amino acid linker sequence). When the fusion partner and the FGFR1 ECD are covalently coupled by chemical means, linkers of various sizes may typically be included during the coupling reaction.

Exemplary methods of non-covalently attaching a fusion partner to an FGFR1 ECD include, but are not limited to, attachment through a binding pair. Exemplary binding pairs include, but are not limited to, biotin and avidin or streptavidin, an antibody and its antigen, etc.

Co-Translational and Post-Translational Modifications

The invention encompasses administration of FGFR1 ECDs and FGFR1 ECD fusion molecules that are differentially modified during or after translation, for example by glycosylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. A nonlimiting discussion of various post-translational modifications of FGFR1 ECDs and FGFR1 ECD fusion molecules can be found, e.g., in U.S. Pat. No. 7,678,890.

FGFR1 ECD and FGFR1 ECD Fusion Molecule Expression and Production Vectors

Vectors comprising polynucleotides that encode FGFR1 ECDs are provided. Vectors comprising polynucleotides that encode FGFR1 ECD fusion molecules are also provided. Such vectors include, but are not limited to, DNA vectors, phage vectors, viral vectors, retroviral vectors, etc.

In some embodiments, a vector is selected that is optimized for expression of polypeptides in CHO or CHO-derived cells. Exemplary such vectors are described, e.g., in Running Deer et al., *Biotechnol. Prog.* 20:880-889 (2004).

In some embodiments, a vector is chosen for in vivo expression of FGFR1 ECDs and/or FGFR1 ECD fusion molecules in animals, including humans. In some such embodiments, expression of the polypeptide is under the control of a promoter that functions in a tissue-specific manner. For example, liver-specific promoters are described, e.g., in PCT Publication No. WO 2006/076288. A nonlimiting discussion of various expression vectors can be found, e.g., in U.S. Pat. No. 7,678,890.

Host Cells

In various embodiments, FGFR1 ECDs or FGFR1 ECD fusion molecules may be expressed in prokaryotic cells, such as bacterial cells; or in eukaryotic cells, such as fungal cells, plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S and DG44 cells; and NSO cells. In some embodiments, a particular eukaryotic host cell is selected based on its ability to make certain desired post-translational modifications to the FGFR1 ECDs or FGFR1 ECD fusion molecules. For example, in some embodiments, CHO cells produce FGFR1 ECDs and/or FGFR1 ECD fusion molecules that have a higher level of sialylation than the same polypeptide produced in 293 cells.

Introduction of a nucleic acid into a desired host cell may be accomplished by any method known in the art, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art. A nonlimiting discussion of host cells and methods of polypeptides in host cells can be found, e.g., in U.S. Pat. No. 7,678,890.

In some embodiments, a polypeptide may be produced in vivo in an animal that has been engineered or transfected with a nucleic acid molecule encoding the polypeptide, according to methods known in the art.

Purification of FGFR1 ECD Polypeptides

FGFR1 ECDs or FGFR1 ECD fusion molecules may be purified by various methods known in the art. Such methods include, but are not limited to, the use of affinity matrices or hydrophobic interaction chromatography. Suitable affinity ligands include any ligands of the FGFR1 ECD or of the fusion partner. Suitable affinity ligands in the case of an antibody that binds FGFR1 include, but are not limited to, FGFR1 itself and fragments thereof. Further, a Protein A, Protein G, Protein A/G, or an antibody affinity column may be used to bind to an Fc fusion partner to purify an FGFR1 ECD fusion molecule. Antibodies to FGFR1 ECD may also be used to purify FGFR1 ECD or FGFR1 ECD fusion molecules. Hydrophobic interactive chromatography, for example, a butyl or phenyl column, may also suitable for purifying some polypeptides. Many methods of purifying polypeptides are known in the art. A nonlimiting discussion of various methods of purifying polypeptides can be found, e.g., in U.S. Pat. No. 7,678,890.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Administration of FGFR1-ECD.339-Fc and Docetaxel in the H1703 Non-Small Cell Lung Cancer (NSCLC) Xenograft Model Six week old female SCID mice were purchased from Charles River Laboratories (Wilmington, Mass.) and were acclimated for 1 week before the start of the study. Human non-small cell lung cancer (NSCLC) cell line H1703 was used as the tumor model and was purchased from ATCC (Manassas, Va.; Cat. No. CRL-5889). The cells were cultured for three passages in RPMI+10% FBS+1% L-glutamine at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at $2.5 \times 10^7$ cells per milliliter. The cells were implanted subcutaneously over the right flank of the mice at $2.5 \times 10^6$ cells/100 µl/mouse. One day after tumor implantation, mice were randomized according to body weight at 10 mice per group.

FGFR1-ECD.339-Fc was formulated in PBS at 3 mg/ml and administered intraperitoneally (i.p.) at 15 mg/kg (300 µg/100 µl/mouse) twice a week for four weeks. Docetaxel was purchased from Toronto Research Chemicals (North York, Ontario, Canada; cat. No. D494420) and formulated in $H_2O$ containing 5% Tween 80 and 5% glucose. Docetaxel was administered i.p. at 25 mg/kg (equivalent to about 75 mg/m$^2$ in a human) once every three weeks for two doses. In combination groups, FGFR1-ECD.339-Fc and docetaxel were either given concurrently or sequentially with FGFR1-ECD.339-Fc given one day before docetaxel or vice versa. Human albumin was purchased from Grifols USA (Los Angeles, Calif.; Cat. No. NDC 61953-0002-1), formulated in PBS at 3 mg/mL and was used as negative control at 300 µg/100 µL/mouse (15 mg/kg). The dosing schedule for each set of mice is shown in Table 2.

TABLE 2

Dosing Schedule

| Group | n | Route | Treatment | Schedule |
|---|---|---|---|---|
| 1 | 10 | i.p. | Albumin | 2x/wk × 6 wks |
| 2 | 10 | i.p. | FGFR1-ECD.339-Fc | 2x/wk × 6 wks |
| 3 | 10 | i.p. | Docetaxel | 1x/3 wk × 2 doses |
| 4 | 10 | i.p. | FGFR1-ECD.339-Fc | 2x/wk × 6 wks |
|   |   | i.p. | Docetaxel | 1x/3 wk × 2 doses |
| 5 | 10 | i.p. | FGFR1-ECD.339-Fc | 2x/wk × 6 wks |
|   |   | i.p. | Docetaxel (1 day after) | 1x/3 wk × 2 doses |
| 6 | 10 | i.p. | FGFR1-ECD.339-Fc | 2x/wk × 6 wks |
|   |   | i.p. | Docetaxel (1 day before) | 1x/3 wk × 2 doses |

The tumor volume and body weight of the mice were monitored twice a week throughout the study. The tumor volume was measured by external caliper to determine the greatest longitudinal diameter (length) and the greatest transverse diameter (width). The tumor volume was then calculated using the following formula:

Tumor volume (mm$^3$)=(length×width$^2$)/2

On day 38, when the average tumor volume in the Albumin group reached 850 mm$^3$, the mice were euthanized by isoflurane inhalation and cervical dislocation.

The mean tumor volume throughout the study for each set of mice is shown in FIG. 1. In that experiment, sequential administration of FGFR1-ECD.339-Fc and docetaxel inhibited tumor growth more than either drug alone. Furthermore, in that experiment, concurrent administration of FGFR1-ECD.339-Fc and docetaxel was more effective than sequential administration at inhibiting tumor growth. No weight loss was observed over the course of the study. (Data not shown.)

The tumor volume of each group of mice on day 38 was analyzed by one-way ANOVA followed by Tukey's test. The results of that analysis are shown in Table 3.

TABLE 3

Tumor volume analysis on day 38

|  | Mean Tumor volume mm$^3$(±SD) | Tumor growth inhibition (%) | p Value compare to control (Tukey's test) |
|---|---|---|---|
| Albumin | 835 (±151) | — | — |
| FGFR1-ECD.339-Fc | 557 (±151) | 33 | <0.01 |
| Docetaxel | 209 (±303) | 74 | <0.001 |
| FGFR1-ECD.339-Fc/Docetaxel concurrent | 27 (±55) | 96 | <0.001 |
| FGFR1-ECD.339-Fc/Docetaxel Sequential | 99 (±117) | 88 | <0.001 |
| Docetaxel/FGFR1-ECD.339-Fc Sequential | 72 (±109) | 91 | <0.001 |

Administration of FGFR1-ECD.339-Fc alone resulted in 33% (p<0.01) tumor growth inhibition, and administration of docetaxel alone resulted in 74% (p<0.001) tumor growth inhibition. Sequential administration with FGFR1-ECD.339-Fc first resulted in 88% (p<0.001) tumor growth inhibition, and sequential administration with docetaxel first resulted in 91% (p<0.001) tumor growth inhibition. Finally, concurrent dosing of FGFR1-ECD.339-Fc and docetaxel resulted in 96% (p<0.001) tumor growth inhibition.

Fractional tumor volume analysis was used to assess the degree of enhanced (additive or synergistic) or decreased (antagonistic) tumor growth inhibition in the sequential and concurrent combinations of FGFR1-ECD.339-Fc and docetaxel. The results of that analysis are shown in Table 4.

TABLE 4

Analysis of fractional tumor volume[a] on day 38

|  | FGFR1-ECD.339-Fc | Docetaxel | Expected[b] | Observed | Expected/Observed[c] |
|---|---|---|---|---|---|
| Concurrent | 0.68 | 0.25 | 0.17 | 0.03 | 5.67 |
| FGFR1-ECD.339-Fc/Docetaxel sequential | 0.68 | 0.25 | 0.17 | 0.11 | 1.55 |
| Docetaxel/FGFR1-ECD.339-Fc sequential | 0.68 | 0.25 | 0.17 | 0.09 | 1.89 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results demonstrate that concurrent administration of FGFR1-ECD.339-Fc and docetaxel results in synergistic inhibition of tumor growth, while sequential administration of FGFR1-ECD.339-Fc and docetaxel results in additive inhibition.

Example 2

Administration of FGFR1-ECD.339-Fc and Pemetrexed in the H520 Non-Small Cell Lung Cancer (NSCLC) Xenograft Model Six to eight week old female SCID mice were purchased from Charles River Laboratories (Wilmington, Mass.) and were acclimated for 1 week before the start of the study. Squamous cell lung cancer cell line NCI-H520 was used as the tumor model and was purchased from ATCC (Manassas, Va.; Cat. No. HTB-182). The cells were cultured for three to four passages in RPMI+10% FBS+1% L-glutamine at 37° C. in a humidified atmosphere with 5% $CO_2$. When the cultured cells reached 85-90% confluence, cells were harvested and resuspended in cold $Ca^{2+}$ and $Mg^{2+}$ free PBS containing 50% Matrigel at $3.5 \times 10^7$ cells/ml. The cells were implanted subcutaneously over the right flank of the mice at $3.5 \times 10^6$ cells/100 µl/mouse. One day after tumor implantation, mice were randomized according to body weight at 10 mice per group. Dosing for all groups began one day post tumor implantation.

FGFR1-ECD.339-Fc was formulated in PBS at 3 mg/ml and administered intraperitoneally (i.p.) at 15 mg/kg (300 µg/100 µl/mouse) twice a week for six weeks. Pemetrexed disodium was purchased from Fisher Scientific (Pittsburgh, Pa.; Cat. No. NC9564691) and formulated in Saline USP at 12.5 mg/mL, 25 mg/mL, and 50 mg/mL. Pemetrexed was administered i.p. at three different dosage levels: 62.6 mg/kg (1.25 mg/100 µl/mouse); 125 mg/kg (2.5 mg/100 µl/mouse); and 250 mg/kg (5 mg/100 µl/mouse) daily for five days in week one, and daily for five days in week 2. In combination groups, FGFR1-ECD.339-Fc and pemetrexed were administered on the same schedule as when given as single agents, and were administered concurrently on days 1, 4, 8, and 11. Human albumin was purchased from Grifols USA (Los Angeles, Calif.; Cat. No. NDC 61953-0002-1), formulated in PBS at 3 mg/mL and was used as negative control at 300 µg/100 µL/mouse (15 mg/kg). The dosing schedule for each group of mice is shown in Table 5.

TABLE 5

Dosing Schedule

| Group | n | Route | Treatment | Dose | Schedule |
|---|---|---|---|---|---|
| 1 | 10 | i.p. | Albumin | 15 mg/kg | 2x/wk × 6 wks |
| 2 | 10 | i.p. | FGFR1-ECD.339-Fc | 15 mg/kg | 2x/wk × 6 wks |
| 3 | 10 | i.p. | Pemetrexed | 62.5 mg/kg | QD × 5 × 2 cycles |
| 4 | 10 | i.p. | Pemetrexed | 125 mg/kg | QD × 5 × 2 cycles |
| 5 | 10 | i.p. | Pemetrexed | 250 mg/kg | QD × 5 × 2 cycles |
| 6 | 10 | i.p. i.p. | FGFR1-ECD.339-Fc Pemetrexed | 15 mg/kg 62.5 mg/kg | 2x/wk × 6 wks QD × 5 × 2 cycles |
| 7 | 10 | i.p. i.p. | FGFR1-ECD.339-Fc Pemetrexed | 15 mg/kg 125 mg/kg | 2x/wk × 6 wks QD × 5 × 2 cycles |
| 8 | 10 | i.p. i.p. | FGFR1-ECD.339-Fc Pemetrexed | 15 mg/kg 250 mg/kg | 2x/wk × 6 wks QD × 5 × 2 cycles |

The tumor volume and body weight of the mice were monitored twice a week throughout study. The tumor volume was measured and calculated using the method and formula described in Example 1.

Animals were euthanized when any of the following signs were observed before the end of the study: body weight loss of ≥15% of initial body weight; tumor ulceration of ≥30% of tumor surface area; mice were moribund; or the individual tumor volume was ≥2000 mm³. The mice were euthanized by isoflurane inhalation and cervical dislocation.

Figure 2A:
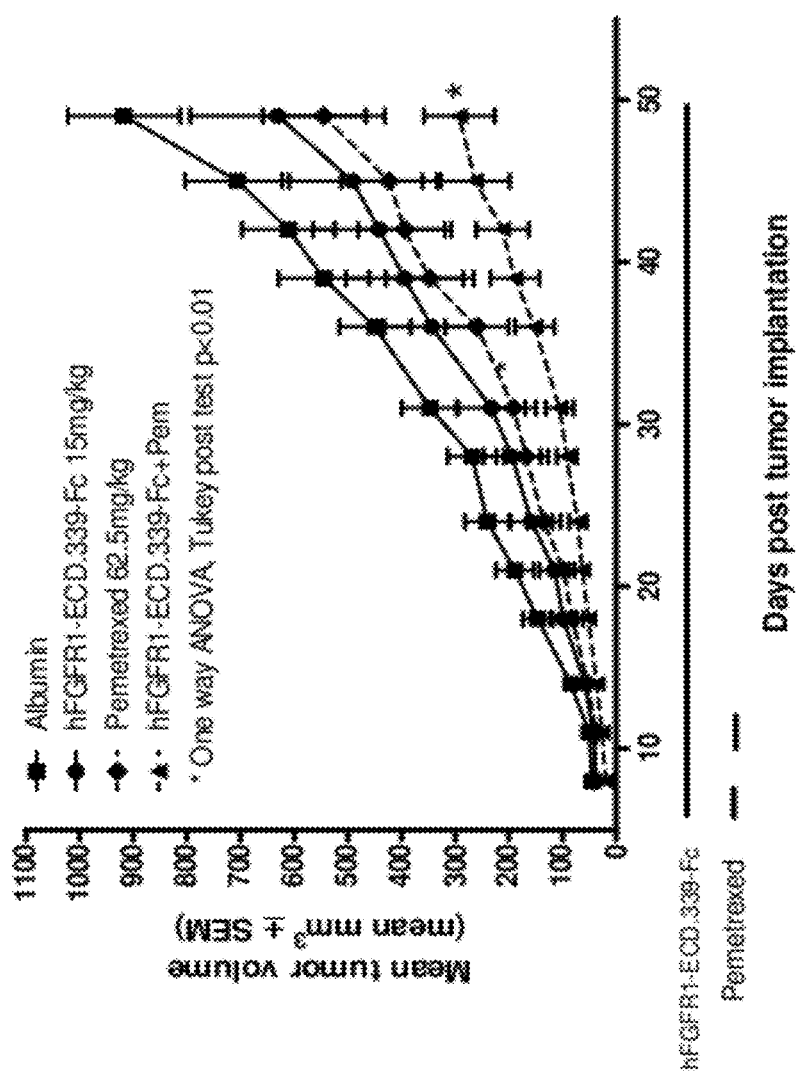
FIG. 2 shows the mean tumor volume (A) and body weight (B) of mice administered FGFR1-ECD.339-Fc alone, pemetrexed alone (62.5 mg/kg dose), or FGFR1-ECD.339-Fc and pemetrexed (62.5 mg/kg dose), as described in Example 2.
Figure 2B:
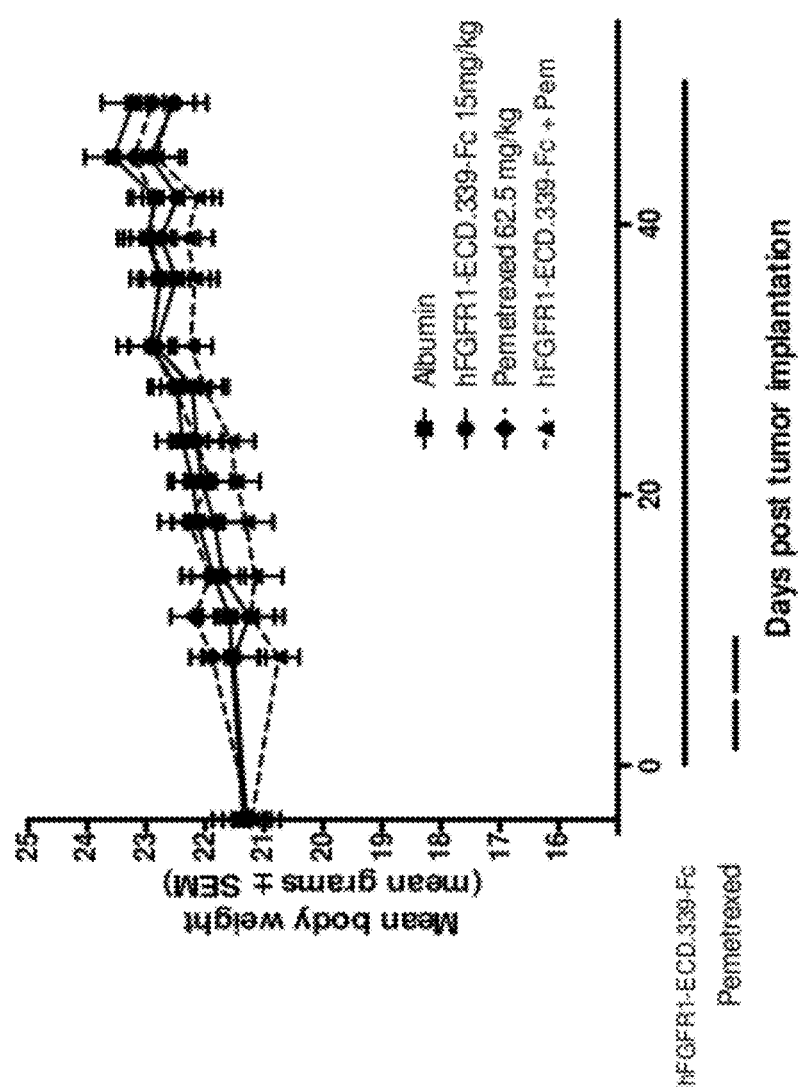
Figure 3A:
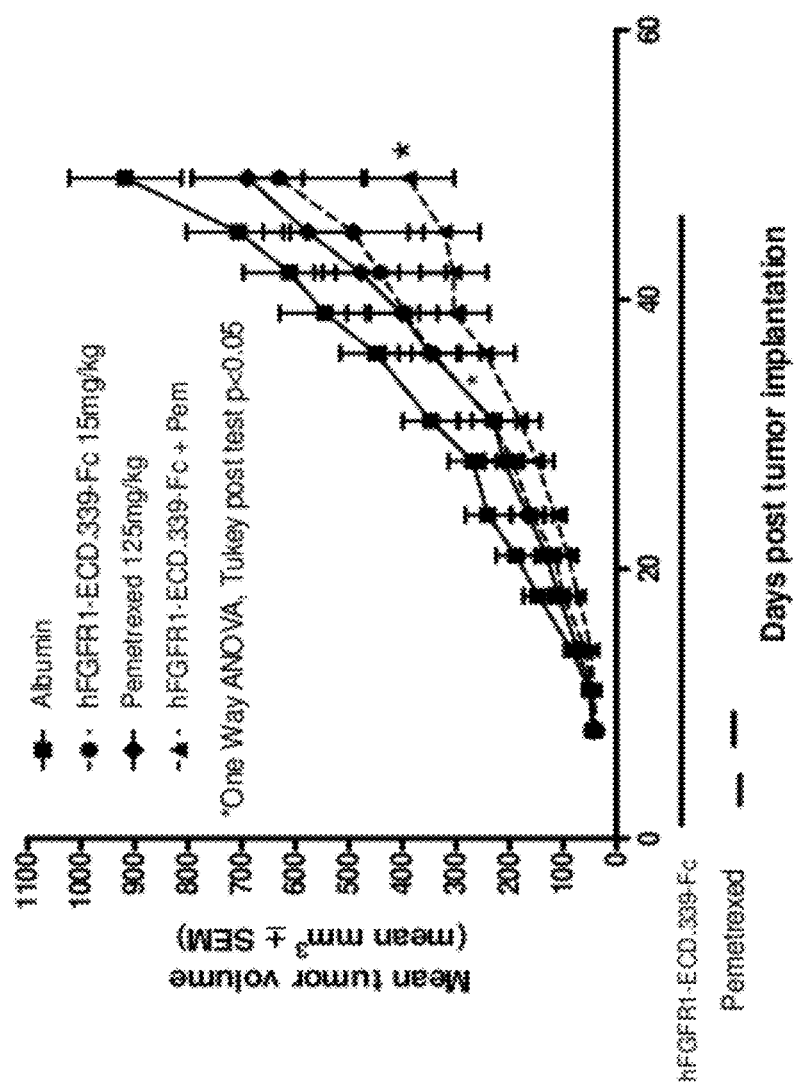
FIG. 3 shows the mean tumor volume (A) and body weight (B) of mice administered FGFR1-ECD.339-Fc alone, pemetrexed alone (125 mg/kg dose), or FGFR1-ECD.339-Fc and pemetrexed (125 mg/kg dose), as described in Example 2.
Figure 3B:
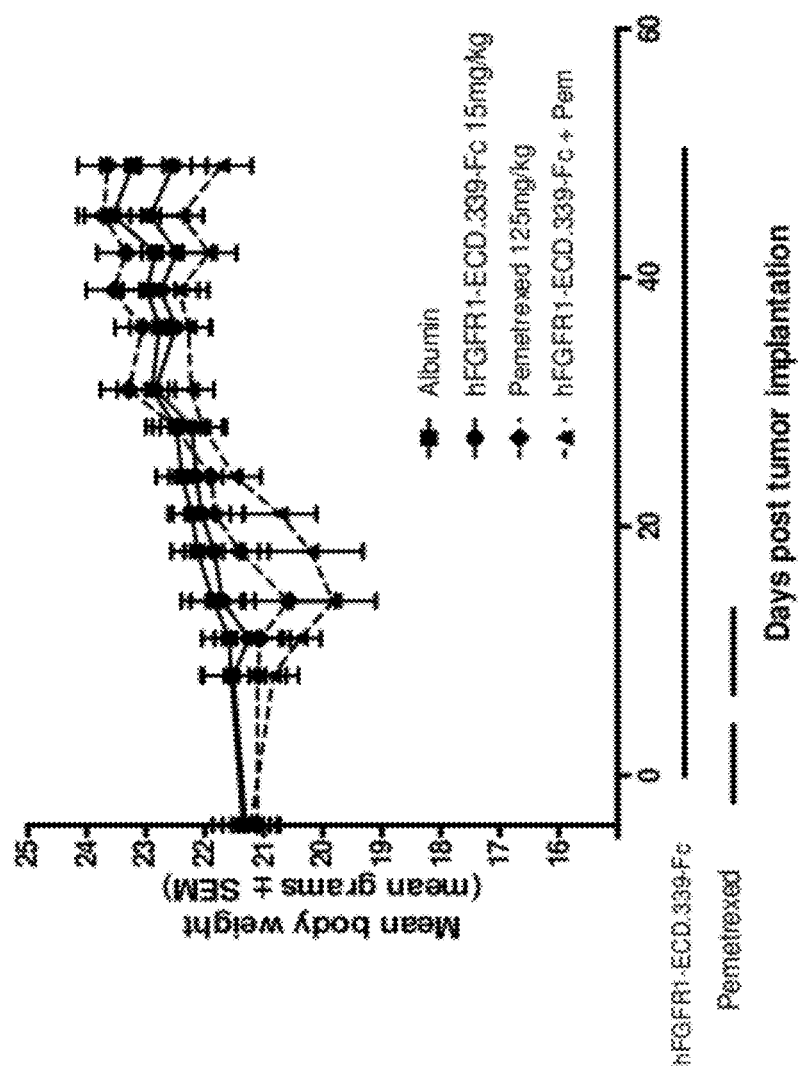
Figure 4A:
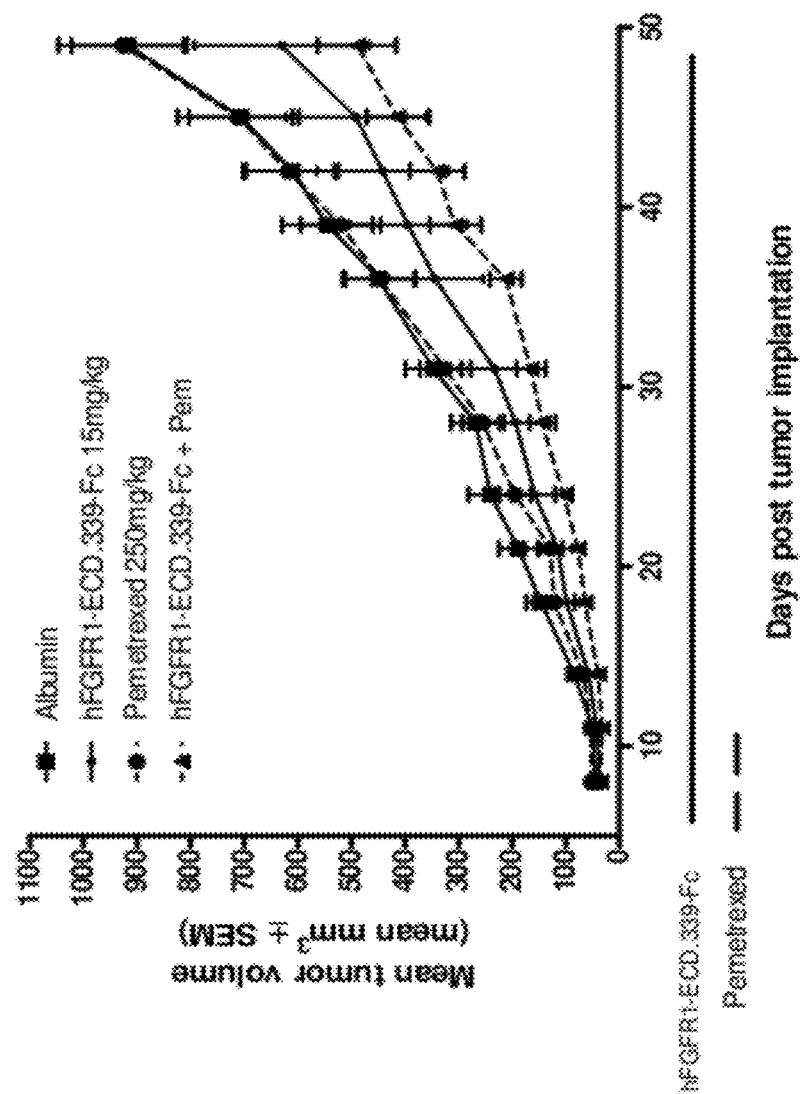
FIG. 4 shows the mean tumor volume (A) and body weight (B) of mice administered FGFR1-ECD.339-Fc alone, pemetrexed alone (250 mg/kg dose), or FGFR1-ECD.339-Fc and pemetrexed (250 mg/kg dose), as described in Example 2.
Figure 4B:
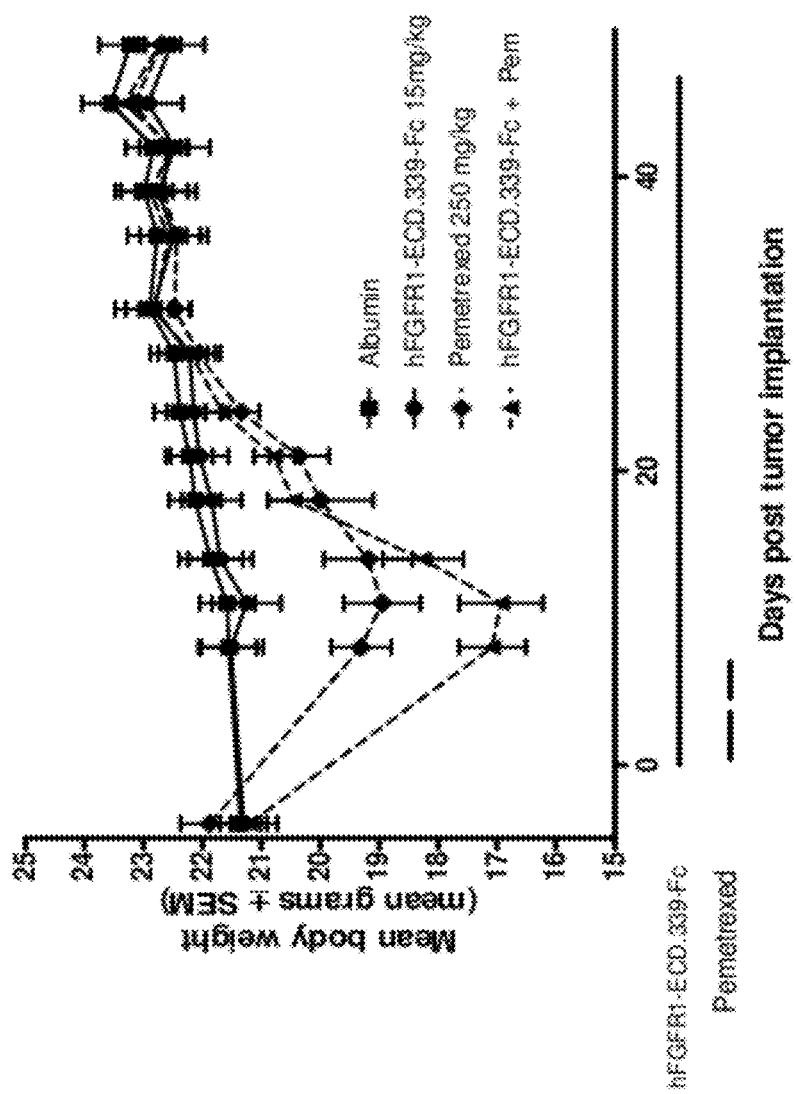

The mean tumor volume throughout the study for low pemetrexed dosage groups, medium pemetrexed dosage groups, and high pemetrexed dosage groups are shown in FIGS. 2A, 3A, and 4A, respectively. FIGS. 2B, 3B, and 4B show the body weight of the mice in each group over the course of the study. It appears that 250 mg/kg pemetrexed is approaching the maximum tolerated dose in the mice, based on the loss of body weight following administration of that dose. See FIG. 4B.

Administration of either FGFR1-ECD.339-Fc or pemetrexed at the low or medium dose alone resulted in tumor inhibition over the course of the study. The highest dose of pemetrexed alone did not appear to inhibit tumor growth. Concurrent dosing of FGFR1-ECD.339-Fc and pemetrexed resulted in greater inhibition of tumor growth, although the tumor inhibition observed with the combination of FGFR1-ECD.339-Fc and the highest dose of pemetrexed was not statistically significant.

The body weight graphs show that the mice tolerated the low and medium doses of pemetrexed well. At the high dose of pemetrexed, the mice initially lost significant body weight. The dosing was therefore stopped after the first 5-day dosing. Thus, in the high dose group, the animals only received the first five doses and missed the second five doses.

The tumor volume of each group of mice on day 49 was analyzed by one-way ANOVA followed by Tukey's test. The results of that analysis are shown in Table 6.

TABLE 6

Tumor volume analysis on day 49

| | Mean Tumor volume mm³(±SD) | Tumor growth inhibition (%) | p Value compare to control (Tukey's test) |
|---|---|---|---|
| Albumin | 917.3 (±313.9) | — | — |
| FGFR1-ECD.339-Fc | 630.4 (±461.5) | 31 | >0.05 |
| Pemetrexed 62.5 mg/kg | 544.7 (±341.5) | 40 | >0.05 |
| FGFR1-ECD.339-Fc/ Pemetrexed 62.5 mg/kg | 292.5 (±198.5) | 68 | <0.01 |
| Pemetrexed 125 mg/kg | 689.5 (±328.7) | 24 | >0.05 |
| FGFR1-ECD.339-Fc/ Pemetrexed 125 mg/kg | 389.2 (±271.3) | 57 | <0.05 |
| Pemetrexed 250 mg/kg | 926.6 (±339.9) | 1 | >0.05 |
| FGFR1-ECD.339-Fc/ Pemetrexed 250 mg/kg | 489.3 (±231.0) | 46 | >0.05 |

Administration of FGFR1-ECD.339-Fc alone resulted in 31% (p>0.05) tumor growth inhibition, and administration of pemetrexed alone at 62.5, 125 or 250 mg/kg resulted in 40, 24 or 1% (p>0.05) tumor growth inhibition respectively. Concurrent dosing of FGFR1-ECD.339-Fc (15 mg/kg) and pemetrexed at 62.5, 125, or 250 mg/kg resulted in 68% (p<0.01), 57% (p<0.05) or 46% (p>0.05) tumor growth inhibition respectively.

Fractional tumor volume analysis was used to assess the degree of enhanced (additive or synergistic) or decreased (antagonistic) tumor growth inhibition following administration of FGFR1-ECD.339-Fc and pemetrexed. The results of that analysis are shown in Table 7.

TABLE 7

Analysis of fractional tumor volume[a] on day 49

| | FGFR1-ECD.339-Fc | Pemetrexed | Expected[b] | Observed | Expected/Observed[c] |
|---|---|---|---|---|---|
| Pemetrexed 62.5 | 0.68 | 0.59 | 0.40 | 0.31 | 1.29 |
| Pemetrexed 125 | 0.68 | 0.75 | 0.51 | 0.42 | 1.21 |
| Pemetrexed 250 | 0.68 | 1.00 | 0.68 | 0.53 | 1.28 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results demonstrate that administration of FGFR1-ECD.339-Fc and pemetrexed results in additive inhibition of tumor growth.

Example 3

Administration of FGFR1-ECD.339-Fc in Combination with Various Chemotherapeutics in the A549 Non-Small Cell Lung Cancer (NSCLC) Xenograft Model Six weeks old female SCID mice were purchased from Charles River Laboratories (Wilmington, Mass.) and were acclimated for 1 week before the start of the study. A549 cells purchased from ATCC (Manassas, Va.; Cat. No. CCL-185) were cultured for three passages in RPMI+10% FBS+1% L-glutamine at 37° C. in a humidified atmosphere with 5% $CO_2$ When the cultured cells reached 85-90% confluence, cells were harvested and resuspended in cold $Ca^{2+}$ and $Mg^{2+}$ free phosphate buffered saline (PBS) containing 50% Matrigel at $5 \times 10^7$ cells per milliliter. The cells were implanted subcutaneously over the right flank of the mice at $5 \times 10^6$ cells/100 μl/mouse. One day after tumor implantation, mice were randomized according to body weight at 10 mice per group.

The tumor volume and body weight of the mice were monitored twice a week throughout each study. The tumor volume was measured and calculated using the method and formula described in Example 1.

The tumor volume of each group of mice at the end of each study was analyzed by one-way ANOVA followed by Tukey's test. Fractional tumor volume analysis was then used to assess the degree of enhanced (additive or synergistic) or decreased (antagonistic) tumor growth inhibition achieved following administration of FGFR1-ECD.339-Fc with one or more additional chemotherapeutic molecules.

Certain study details, and the results for each combination, are discussed below.

A. FGFR1-ECD.339-Fc and Cisplatin

FGFR1-ECD.339-Fc was formulated in 0.9% Sodium Chloride Injection USP (Henry Schein, Inc., Melville, N.Y.; Cat. No. 1533826) at 4 mg/ml and administered intraperitoneally (i.p.) at 20 mg/kg (400 μg/100 μl/mouse) twice per week for six weeks. Cisplatin was purchased from Sigma-Aldrich (St. Louis, Mo.; Cat. No. P4394), formulated in 0.9% saline, and administered i.p. at 3.5 mg/kg (17 μg/100 μl per mouse) once per week for six weeks. Saline was used as negative control and was administered i.p. at 100 μl per mouse twice a week for six weeks.

On day 42, when the average tumor volume in the vehicle group reached 1300 $mm^3$, the mice were euthanized by isoflurane inhalation and cervical dislocation.

Figure 5:
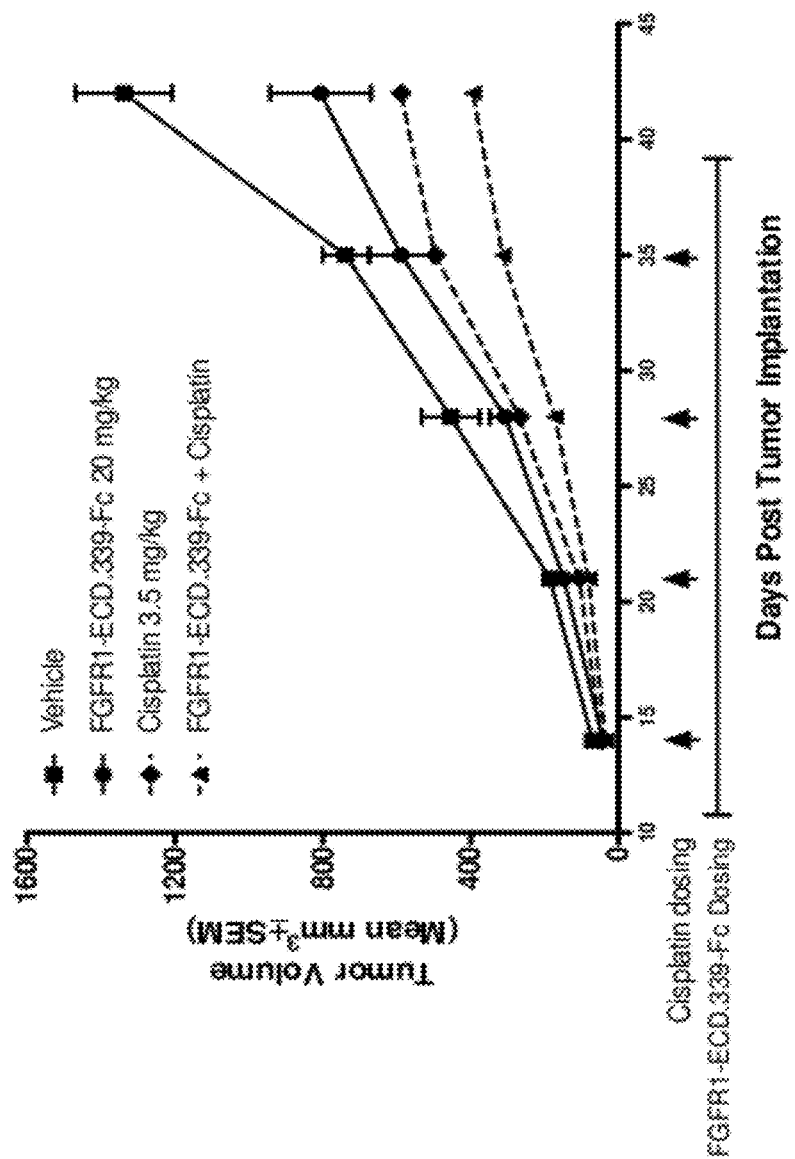
FIG. 5 shows the mean tumor volume in mice administered FGFR1-ECD.339-Fc alone, cisplatin alone, or the combination of FGFR1-ECD.339-Fc and cisplatin, as described in Example 3A.

The mean tumor volume throughout the study for each set of mice is shown in FIG. 5. In that experiment, administration of FGFR1-ECD.339-Fc and cisplatin inhibited tumor growth more than either drug alone. Further, the mice did not lose weight over the course of that study. (Data not shown.)

The tumor volume of each group of mice on day 42 was analyzed by one-way ANOVA followed by Tukey's test. The results of that analysis are shown in Table 8.

TABLE 8

| Tumor volume analysis on day 42 | | | |
|---|---|---|---|
| | Mean Tumor volume $mm^3$ (±SD) | Tumor growth inhibition (%) | p Value compare to control (Tukey's test) |
| Saline vehicle | 1339 (±411) | — | — |
| FGFR1-ECD.339-Fc | 807 (±431) | 39 | <0.01 |
| Cisplatin | 682 (±195) | 49 | <0.001 |
| FGFR1-ECD.339-Fc + Cisplatin | 382 (±210) | 71 | <0.001 |

In order to determine whether combination of FGFR1-ECD.339-Fc and cisplatin resulted in enhanced (additive or synergistic) or decreased (antagonistic) antitumor activity, fractional tumor volume was analyzed as described in Example 1. The results of that analysis are shown in Table 9.

TABLE 9

Analysis of fractional tumor volume[a] on day 42 relative to control

| | FGFR1-ECD.339-Fc | Cisplatin | Expected[b] | Observed | Expected/Observed[c] |
|---|---|---|---|---|---|
| FGFR1-ECD.339-Fc + cisplatin | 0.60 | 0.5 | 0.30 | 0.28 | 1.07 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results show that the combination of FGFR1-ECD.339-Fc and cisplatin resulted in additive inhibition of tumor growth in that experiment.

B. FGFR1-ECD.339-Fc and Paclitaxel

The combination of FGFR1-ECD.339-Fc and paclitaxel was tested in the A549 human non-small cell lung cancer xenograft model, described above. FGFR1-ECD.339-Fc was formulated in 0.9% Saline for Injection USP at 3 mg/ml. Paclitaxel was purchased from Bedford Laboratories (Bedford, Ohio; Cat. No. 1075029) and was formulated in 0.9% saline for injection containing 5% dextrose at 3.6 mg/ml for a dose of 18 mg/kg. FGFR1-ECD.339-Fc was administered intraperitoneally (i.p.) at 15 mg/kg twice per week for 5 weeks. Paclitaxel was administered i.p. at 18 mg/kg on days 8, 12, and 15.

When the average tumor volume in vehicle control group reached ~500 $mm^3$, the mice were euthanized by isoflurane inhalation and cervical dislocation.

Figure 6:
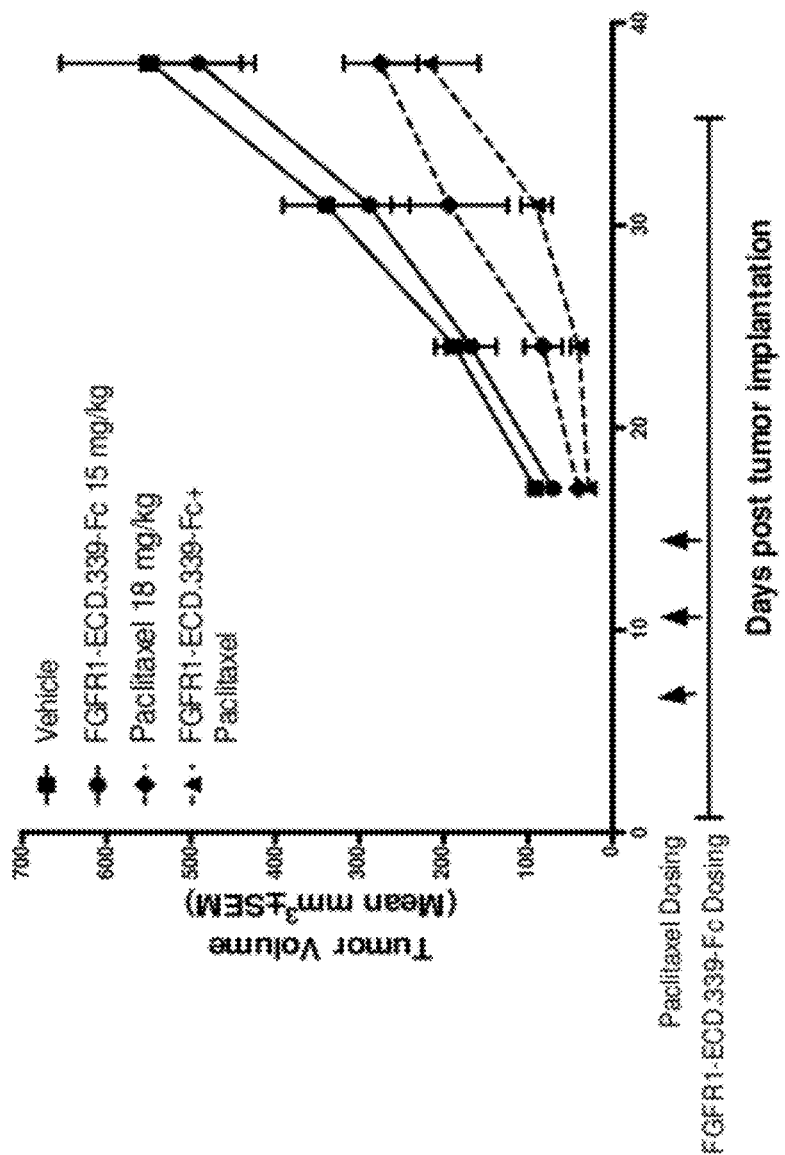
FIG. 6 shows the mean tumor volume in mice administered FGFR1-ECD.339-Fc alone, paclitaxel alone, or the combination of FGFR1-ECD.339-Fc and paclitaxel, as described in Example 3B.

The mean tumor volume throughout the study for each set of mice is shown in FIG. 6. In that experiment, the combination of FGFR1-ECD.339-Fc and paclitaxel inhibited tumor growth more than either drug alone. Further, the mice did not lose weight over the course of that study. (Data not shown.)

In order to determine whether the combination of FGFR1-ECD.339-Fc and paclitaxel resulted in additive, synergistic, or antagonistic activity, fractional tumor volume on day 31 and day 38 was analyzed as described in Example 1. The results of that analysis are shown in Table 10.

TABLE 10

Analysis of fractional tumor volume[a] on day 31 and day 38

| Day | FGFR1-ECD.339-Fc | Paclitaxel | Expected[b] | Observed | Expected/Observed[c] |
|---|---|---|---|---|---|
| 31 | 0.84 | 0.57 | 0.48 | 0.26 | 1.81 |
| 38 | 0.89 | 0.50 | 0.45 | 0.39 | 1.13 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results show that administration of FGFR1-ECD.339-Fc and paclitaxel resulted in additive inhibition of tumor growth.

C. FGFR1-ECD.339-Fc and 5-FU

The combination of FGFR1-ECD.339-Fc and 5-fluorouracil (5-FU) was tested in the A549 human non-small cell lung cancer xenograft model, described above. FGFR1-ECD.339-Fc was formulated in 0.9% Saline for Injection USP at 3 mg/ml. 5-FU was purchased from Sigma-Aldrich (St. Louis, Mo.; Cat. No. F6627) and was initially dissolved in dimethyl sulfoxide (DMSO, Sigma-Aldrich, St. Louis, Mo.; Cat. No. D8418-50) at the concentration of 50 mg/ml as a stock solution. The stock solution was further diluted in 0.9% Sodium Chloride Injection USP to 6.6 mg/ml (for 33 mg/kg dosing). FGFR1-ECD.339-Fc was administered intraperitoneally (i.p.) at 15 mg/kg twice per week for four weeks. 5-FU was administered i.p. at 33 mg/kg twice a week for three weeks.

Mice were euthanized on day 31 by isoflurane inhalation and cervical dislocation.

Figure 7:
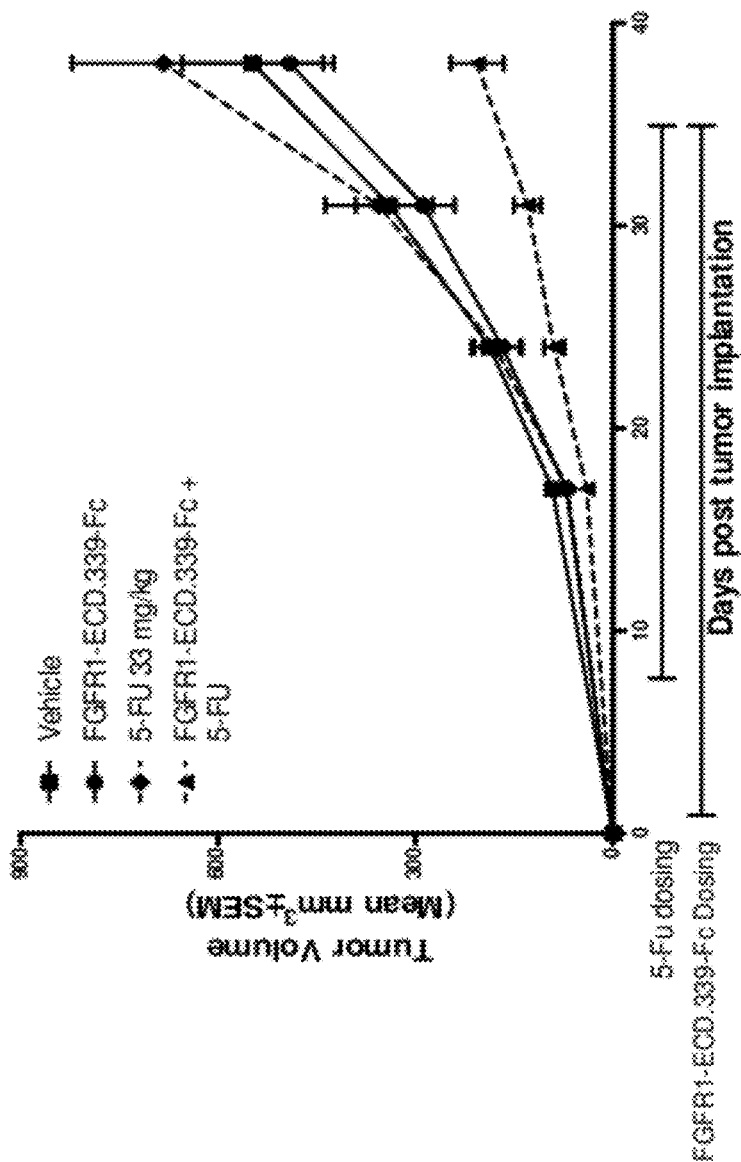
FIG. 7 shows the mean tumor volume in mice administered FGFR1-ECD.339-Fc alone, 5-FU alone, or the combination of FGFR1-ECD.339-Fc and 5-FU, as described in Example 3C.

The mean tumor volume throughout the study for each set of mice is shown in FIG. 7. In that experiment, the combination of FGFR1-ECD.339-Fc and 5-FU inhibited tumor growth more than either drug alone. Further, the mice did not lose weight over the course of that study. (Data not shown.)

In order to determine whether the combination of FGFR1-ECD.339-Fc and 5-FU resulted in additive, synergistic, or antagonistic activity, fractional tumor volume on day 31 was analyzed as described in Example 1. The results of that analysis are shown in Table 11.

TABLE 11

Analysis of fractional tumor volume[a] on day 31

| Day | FGFR1-ECD.339-Fc | 5-FU | Expected[b] | Observed | Expected/Observed[c] |
|---|---|---|---|---|---|
| 31 | 0.84 | 1.04 | 0.89 | 0.38 | 2.33 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results show that administration of FGFR1-ECD.339-Fc and 5-FU resulted in synergistic inhibition of tumor growth in that experiment. The inventors note that similar experiments using 20 mg/kg or 50 mg/kg 5-FU did not result in synergy. (Data not shown.)

D. FGFR1-ECD.339-Fc and Docetaxel

The combination of FGFR1-ECD.339-Fc and docetaxel was tested in the A549 human non-small cell lung cancer xenograft model, described above. FGFR1-ECD.339-Fc was formulated in PBS at 3 mg/ml and administered intraperitoneally (i.p.) at 15 mg/kg (300 µg/100 µl/mouse) twice a week for four weeks. Docetaxel was administered i.p. at 3 mg/kg or 10 mg/kg twice per week for four weeks.

Mice in the albumin control group were euthanized on day 32 by isoflurane inhalation and cervical dislocation when the average tumor volume in the group reached 1000 mm³.

Figure 8A:
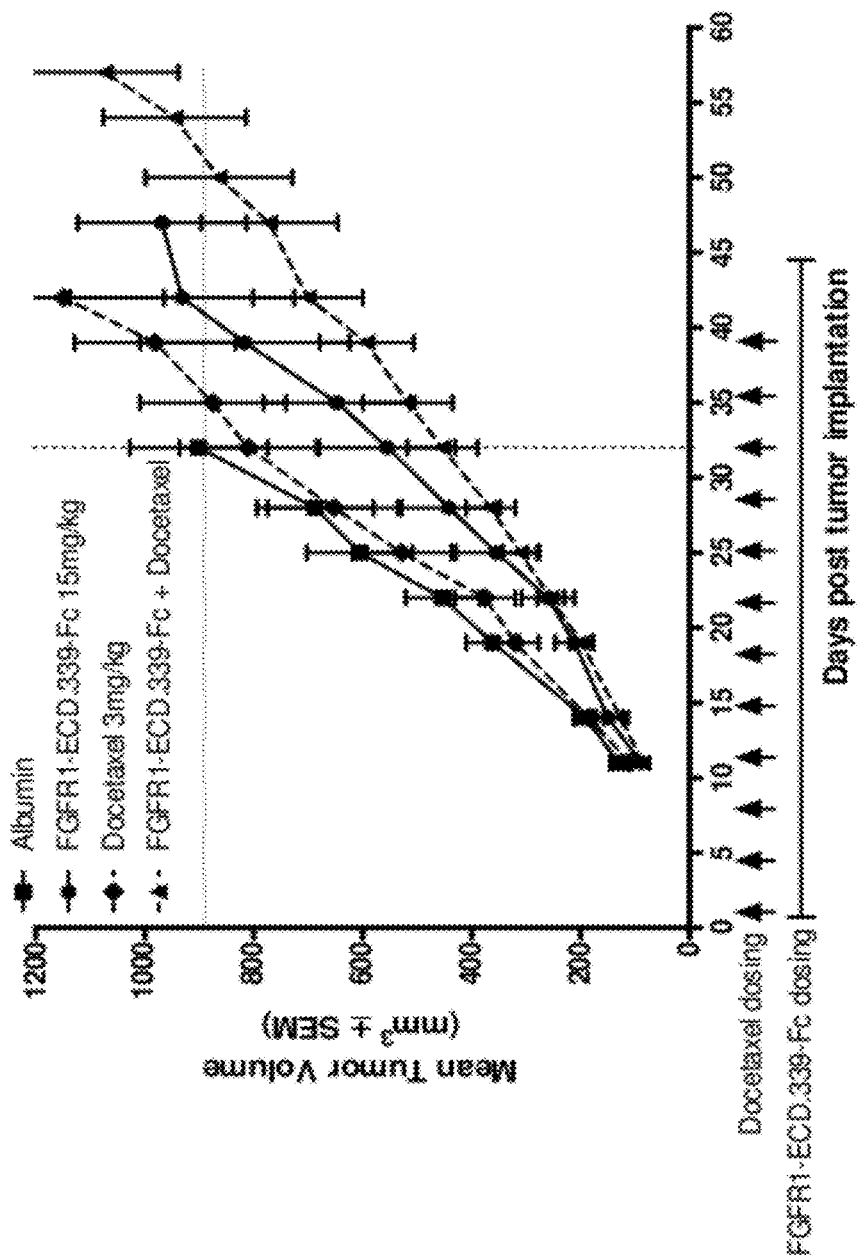
FIG. 8 shows the mean tumor volume in mice administered FGFR1-ECD.339-Fc alone, docetaxel alone, or the combination of FGFR1-ECD.339-Fc and docetaxel, at two different dosages of docetaxel, 3 mg/kg (A) and 10 mg/kg (B), as described in Example 3D.
Figure 8B:
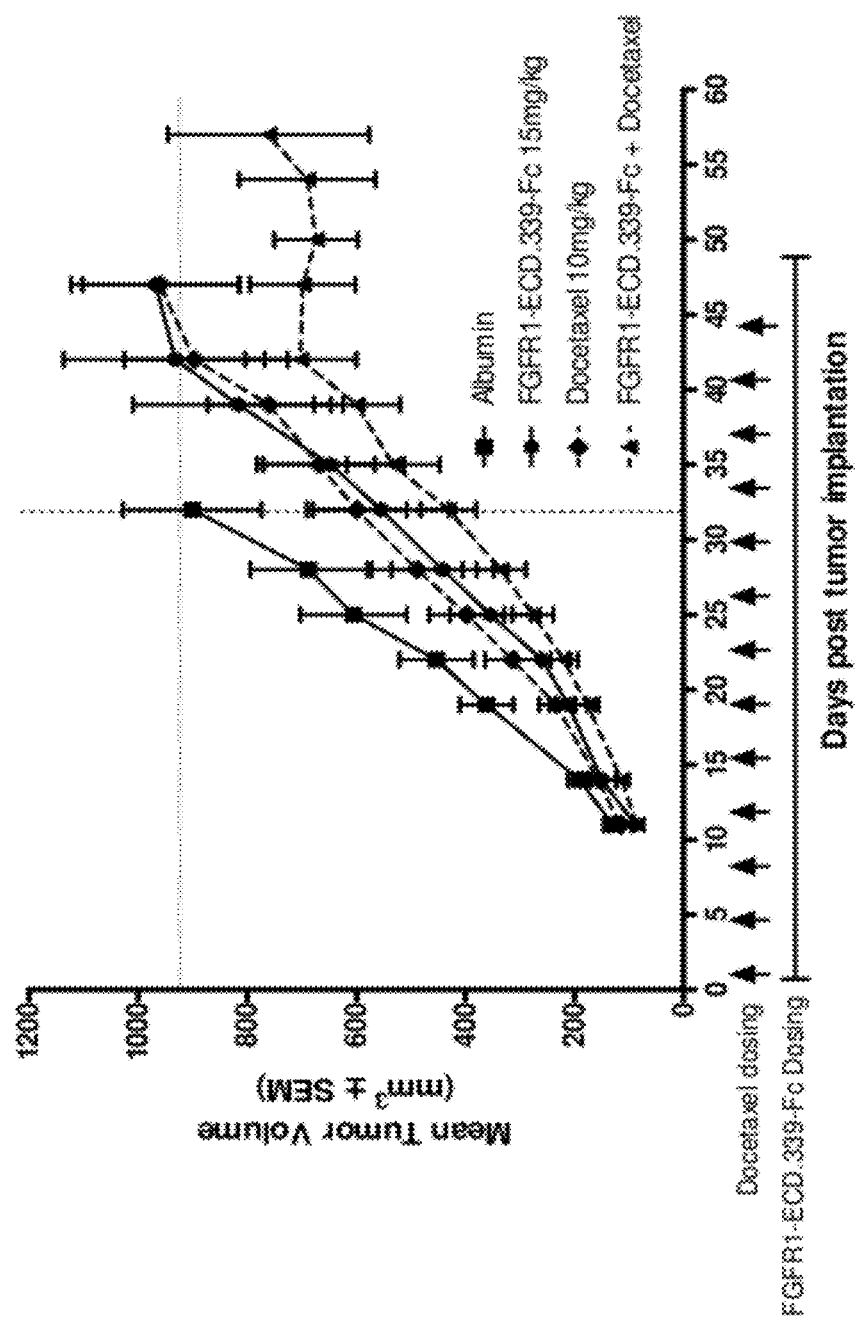

The mean tumor volume throughout the study for each set of mice is shown in FIGS. 8A (3 mg/kg docetaxel) and 8B (10 mg/kg docetaxel). In that experiment, the combination of FGFR1-ECD.339-Fc and docetaxel inhibited tumor growth more than either drug alone, at either dosage of docetaxel. Further, the mice did not lose weight over the course of that study, at either dosage of docetaxel. (Data not shown.)

In order to determine whether the combination of FGFR1-ECD.339-Fc and docetaxel resulted in additive, synergistic, or antagonistic activity, fractional tumor volume on day 32 was analyzed as described in Example 1. The results of that analysis are shown in Table 12.

TABLE 12

Analysis of fractional tumor volume[a] on day 32

| Day | FGFR1-ECD.339-Fc | Docetaxel | Expected[b] | Observed | Expected/Observed[c] |
|---|---|---|---|---|---|
| 32 (3 mg/kg docetaxel) | 0.54 | 0.79 | 0.43 | 0.44 | 0.95 |
| 32 (10 mg/kg docetaxel) | 0.54 | 0.58 | 0.31 | 0.42 | 0.73 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results show that administration of FGFR1-ECD.339-Fc and docetaxel resulted in additive inhibition of tumor growth in that experiment.

E. FGFR1-ECD.339-Fc and Vincristine

The combination of FGFR1-ECD.339-Fc and vincristine was tested in the A549 human non-small cell lung cancer xenograft model, described above. FGFR1-ECD.339-Fc was formulated in 0.9% Saline for Injection USP at 1.5 mg/ml for administration at 15 mg/kg (300 µg/200 µl per mouse), or 2 mg/ml for administration at 20 mg/kg (400 µg/200 µl per mouse). Vincristine was obtained from Fluka-Sigma (St. Louis, Mo. 63103, Catalog #V8879) and was formulated in 0.9% Saline for Injection USP at 0.1 mg/ml or 0.15 mg/mL for administration at 1 mg/kg (0.02 µg/100 µl per mouse) or 1.5 mg/kg (0.03 µg/200 µl per mouse), respectively.

In the first experiment, FGFR1-ECD.339-Fc was administered intraperitoneally (i.p.) at 15 mg/kg twice per week starting on day 1 for six weeks, and vincristine was administered i.p. at 1 mg/kg on days 8, 15, and 22. In the second experiment, FGFR1-ECD.339-Fc was administered intraperitoneally (i.p.) at 20 mg/kg twice per week starting on day 19 for seven weeks, and vincristine was administered i.p. at 1.5 mg/kg on days 27, 34, and 41.

Mice from the first experiment were euthanized 46 days post tumor implantation. In the second study, mice in the albumin control group and mice in the FGFR1-ECD.339-Fc group were euthanized 70 days post tumor implantation, while mice in the vincristine-treated groups were euthanized 77 days post tumor implantation. All of the mice were euthanized by isoflurane inhalation and cervical dislocation.

Figure 9A:
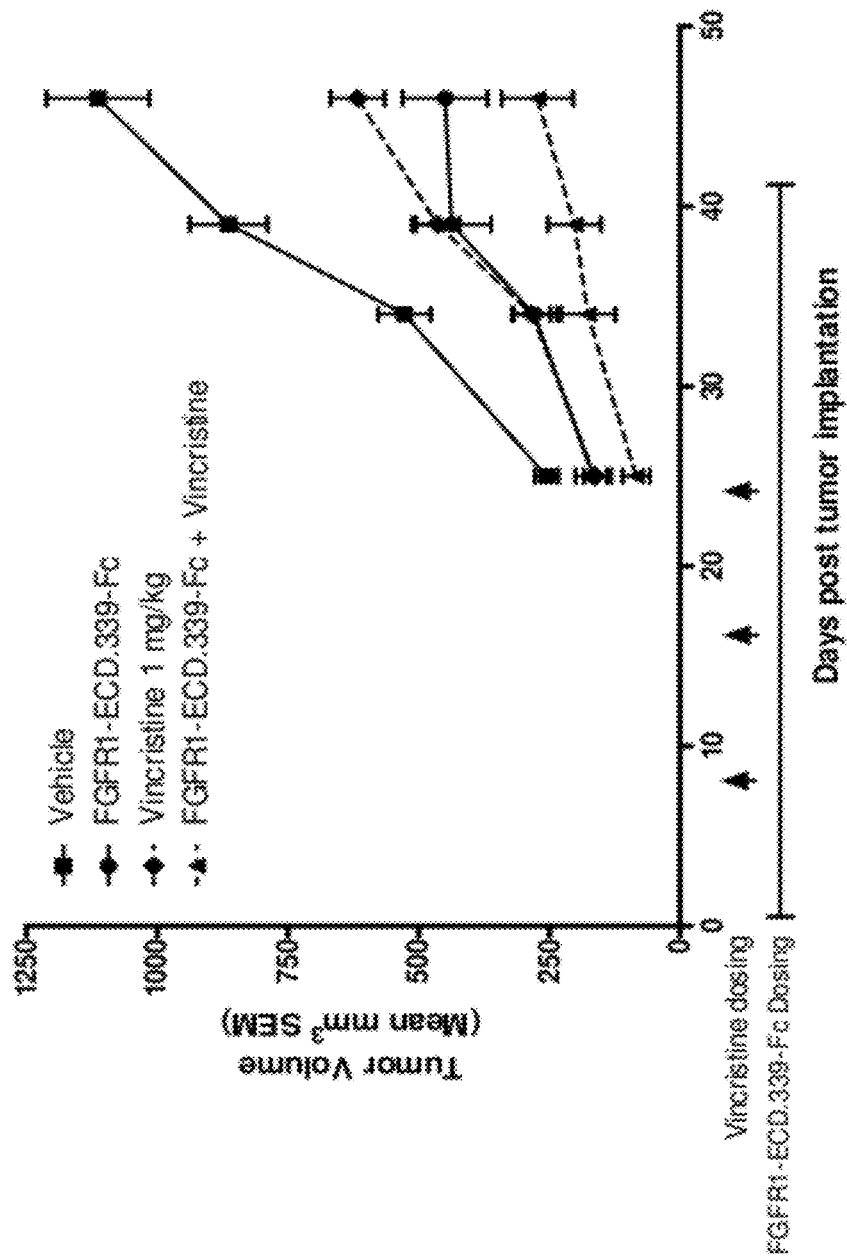
FIG. 9 shows the mean tumor volume in mice administered FGFR1-ECD.339-Fc alone, vincristine alone, or the combination of FGFR1-ECD.339-Fc and vincristine, at two different dosages of vincristine, 1 mg/kg beginning on day 1 (A) and 1.5 mg/kg beginning on day 19 (B), as described in Example 3E. The mean body weight of mice administered 1.5 mg/kg beginning on day 19 is also shown (C).
Figure 9B:
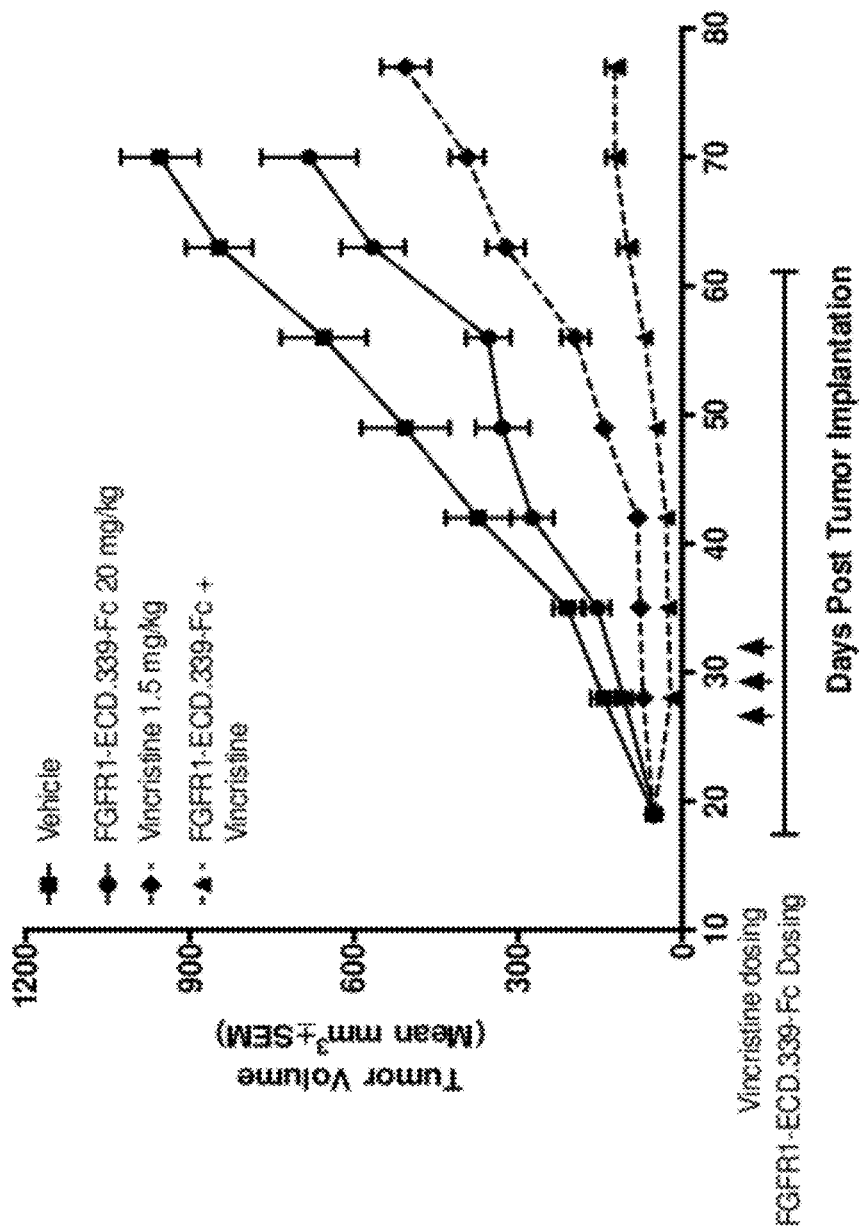
Figure 9C:
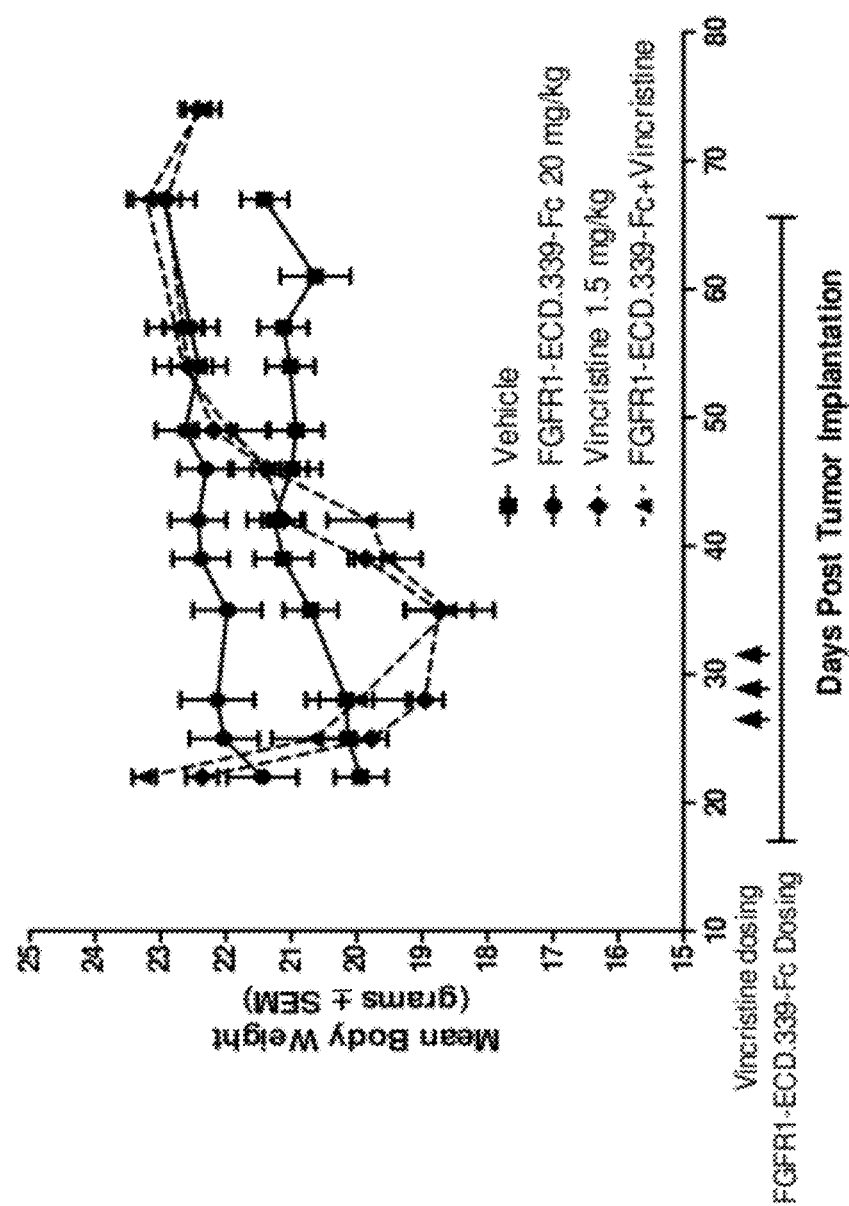

The mean tumor volume throughout the study for each set of mice is shown in FIGS. 9A (1 mg/kg vincristine; dosing begun at day 1) and 9B (1.5 mg/kg vincristine; dosing begun at day 19). In that experiment, the combination of FGFR1-ECD.339-Fc and vincristine inhibited tumor growth more than either drug alone, at either dosage of vincristine, and at either dosing schedule. Further, at the lower dose of vincristine, the mice did not lose weight. (Data not shown.) At the higher dose of vincristine, the mice lost weight, indicating that the higher dose is closer to the maximum tolerated dose. See FIG. 9C.

In order to determine whether the combination of FGFR1-ECD.339-Fc and vincristine resulted in additive, synergistic, or antagonistic activity, fractional tumor volume on days 39 and 46 for the first experiment, and on days 70 for the second experiment, was analyzed as described in Example 1. The results of that analysis are shown in Table 13.

TABLE 13

Analysis of fractional tumor volume[a]

| Dose of FGFR1-ECD.339-Fc | Dose of Vincristine | Day | FGFR1-ECD.339-Fc | Vincristine | Exp.[b] | Obs. | Expected/Observed[c] |
|---|---|---|---|---|---|---|---|
| 15 mg/kg (start day 1) | 1 mg/kg | 39 | 0.50 | 0.53 | 0.27 | 0.23 | 1.16 |
| 15 mg/kg (start day 1) | 1 mg/kg | 46 | 0.40 | 0.55 | 0.22 | 0.24 | 0.91 |
| 20 mg/kg (start day 19) | 1.5 mg/kg | 70 | 0.71 | 0.41 | 0.29 | 0.14 | 2.07 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results show that administration of FGFR1-ECD.339-Fc and vincristine resulted in additive inhibition of tumor growth at the lower dose of vincristine, and synergistic inhibition of tumor growth at the higher dose of vincristine.

F. FGFR1-ECD.339-Fc, Carboplatin, and Paclitaxel

The combination of FGFR1-ECD.339-Fc, carboplatin, and paclitaxel was tested in the A549 human non-small cell lung cancer xenograft model, described above. FGFR1-ECD.339-Fc was formulated in 0.9% Saline for Injection USP at 3 mg/ml (for administration at 15 mg/kg). Carboplatin was obtained from Sigma-Aldrich (St. Luis, Mo. 63103, Catalog #C2538) and was formulated in 0.9% Saline for Injection USP at 2.5 mg/mL for administration at 25 mg/kg (500 µg/200 µL per mouse). Paclitaxel was obtained from LC Laboratories (Woburn, Mass. 01801; Catalog #P-9600) and was formulated in a solution of 50.3% Cremophor® and 49.7% dehydrated alcohol at 20 mg/mL as stock solution. The stock solution was further diluted in 5% dextrose in 0.9% Saline for Injection USP at 3 mg/mL for administration at 30 mg/kg (600 µg/200 µL per mouse).

FGFR1-ECD.339-Fc was administered intraperitoneally (i.p.) at 15 mg/kg twice per week starting on day 7 for three weeks. Carboplatin was administered i.p. at 25 mg/kg twice per week starting on day 7 for three weeks. Paclitaxel was administered i.p. at 30 mg/kg twice per week starting on day 8 for three weeks.

Mice were euthanized on day 34 in single agent groups and on day 41 in combination groups. Mice were euthanized by isoflurane inhalation and cervical dislocation.

Figure 10:
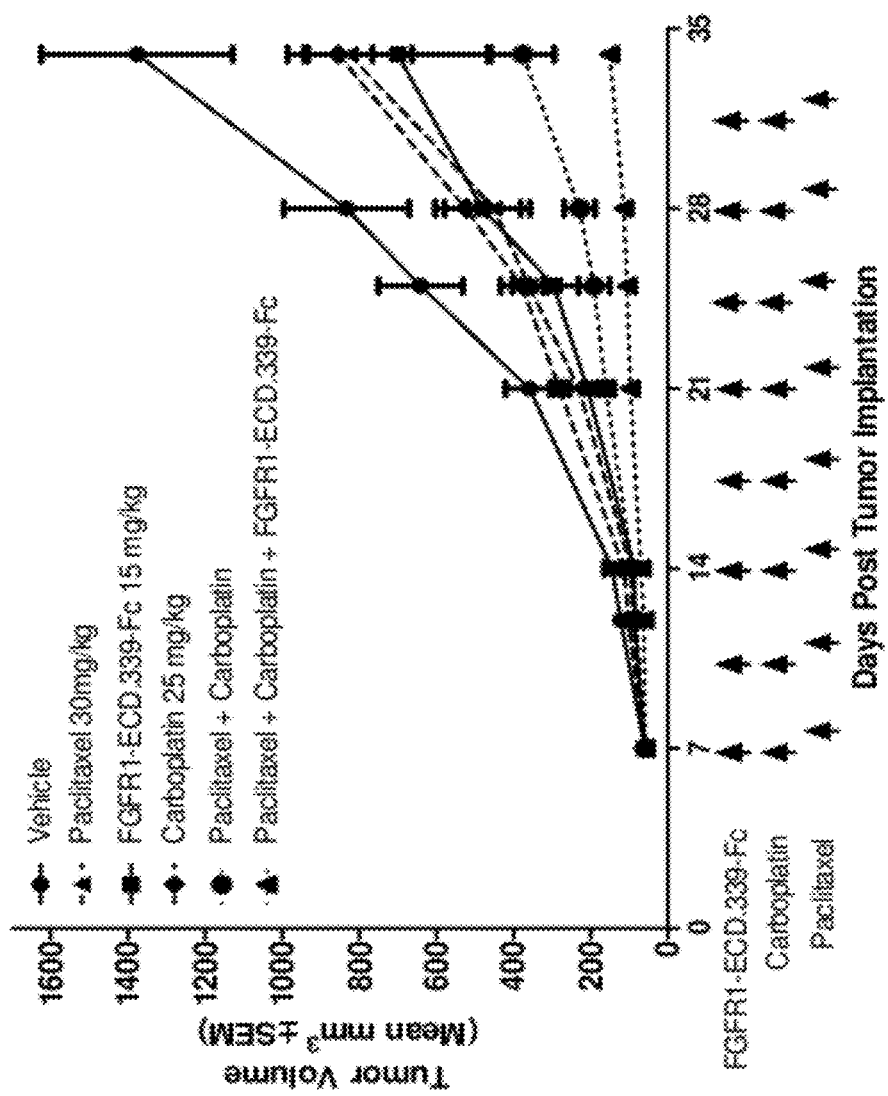
FIG. 10 shows the mean tumor volume in mice administered FGFR1-ECD.339-Fc alone, carboplatin alone, paclitaxel alone, the combination of carboplatin and paclitaxel, and the combination of FGFR1-ECD.339-Fc, carboplatin, and paclitaxel, as described in Example 3F.

The mean tumor volume throughout the study for each set of mice is shown in FIG. 10. In that experiment, the combination of FGFR1-ECD.339-Fc, carboplatin, and paclitaxel inhibited tumor growth more than any of the drugs alone, and also more than the combination of carboplatin and paclitaxel. No weight loss was observed during the course of that study. (Data not shown.)

In order to determine whether the combination of FGFR1-ECD.339-Fc, carboplatin, and paclitaxel resulted in additive, synergistic, or antagonistic activity, fractional tumor volume on day 28 was analyzed as described in Example 1. The results of that analysis are shown in Table 14.

TABLE 14

Analysis of fractional tumor volume[a]

| Day | FGFR1-ECD.339-Fc | Paclitaxel + carboplatin | Expected[b] | Observed | Expected/Observed[c] |
|---|---|---|---|---|---|
| 28 | 0.58 | 0.27 | 0.16 | 0.14 | 1.15 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results show that administration of FGFR1-ECD.339-Fc, carboplatin, and paclitaxel resulted in additive inhibition of tumor growth in that experiment.

Example 4

Administration of FGFR1-ECD.339-Fc in Combination with Various Chemotherapeutics in the Colo205 Colon Cancer Xenograft Model Colo205 cells were purchased from ATCC (Manassas, Va.; Cat. No. CCL-222) and were cultured for 3 passages in RPMI1640 media, 10% FBS, and 1% L-Glutamine at 37° C. in a humidified atmosphere with 5% $CO_2$. Cells were resuspended in a solution of 50%/v PBS and 50%/v Matrigel at a concentration of 25 million cells/ml. Resuspended cells were kept on ice until implantation. Six weeks old female SCID mice were purchased from Charles River Laboratories (Wilmington, Mass.) and were acclimated for 1 week before the start of the study. On day 0, 2.5 million cells/100 µl were implanted over the right flank of the each mouse using a 27G1/2 needle. One day after tumor implantation, the mice were randomized according to the body weight.

The tumor volume and body weight of the mice were monitored twice a week throughout each study. The tumor volume was measured and calculated using the method and formula described in Example 1.

The tumor volume of each group of mice at the end of each study was analyzed by one-way ANOVA followed by Tukey's test. Fractional tumor volume analysis was then used to assess the degree of enhanced (additive or synergistic) or decreased (antagonistic) tumor growth inhibition achieved following administration of FGFR1-ECD.339-Fc with one or more additional chemotherapeutic molecules.

Certain study details, and the results for each combination, are discussed below.

A. FGFR1-ECD.339-Fc, 5-FU, Leucovorin, and Bevacizumab

FGFR1-ECD.339-Fc was formulated in 0.9% Sodium Chloride Injection USP (Henry Schein, Inc, Melville, N.Y.; Cat. No. 1533826) at 2 mg/ml and stored in screw cap microcentrifuge tubes at −80° C. The negative control reagent, human albumin, was purchased from Grifols USA (Los Angeles, Calif.; Cat. No. NDC 61953-0002-1) and was formulated in PBS at 3 mg/ml. 5-FU was purchased from Sigma-Aldrich (St. Louis, Mo.; Cat. No. F6627) and was initially dissolved in dimethyl sulfoxide (DMSO, Sigma-Aldrich, St. Louis, Mo.; Cat. No. D8418-50) at the concentration of 50 mg/ml as a stock solution. The stock solution was further diluted in 0.9% Sodium Chloride Injection USP to 2 mg/ml (for 10 mg/kg dosing), to 4 mg/ml (for 20 mg/kg dosing), and to 6 mg/ml (for 30 mg/kg dosing). Leucovorin (LV) was also purchased from Sigma-Aldrich (Cat. No. F8259) and was formulated in 0.9% Sodium Chloride Injection USP at 2 mg/ml (for 10 mg/kg dosing), to 4 mg/ml (for 20 mg/kg dosing), and to 6 mg/ml (for 30 mg/kg dosing). Bevacizumab was purchased from Genentech, Inc (South San Francisco, Calif.; Cat. No. 15734) and was diluted in 0.9% Sodium Chloride Injection USP to 0.2 mg/ml (for 1 mg/kg dosing).

In the first experiment, FGFR1-ECD.339-Fc was combined with three different concentrations of 5-FU/leucovorin. In the second experiment, FGFR1-ECD.339-Fc was combined with either bevacizumab or 5-FU/leucovorin, or both. The grouping and dosing schedule for the experiments are shown in Table 15. The double line separates the groups from the two experiments.

The results of that experiment according to both methods showed that the antitumor effect of various treatment groups was in the following order: FGFR1-ECD.339-Fc, bevacizumab, and 5-Fu/leucovorin>FGFR1-ECD.339-Fc and bevacizumab>bevacizumab and 5-Fu/leucovorin=bevacizumab>FGFR1-ECD.339-Fc>vehicle.

The average tumor volume of each group of mice in the second experiment on day 24 was analyzed by one-way ANOVA followed by Tukey's test. The results of that analysis are shown in Table 16.

TABLE 15

Dosing Schedule (Dosing started one day post tumor implantation)

| N | Treatment | Drug 1 (Dose, route, Schedule) | Drug 2 (Dose, route, Schedule) | Drug 3 (Dose, route, Schedule) |
|---|---|---|---|---|
| 10 | Albumin + Vehicle | Albumin (10 mg/kg, i.p., 3x/wk × 4 wks) | Saline (100 μl, q.d. × 5 days) | — |
| 10 | FGFR1-ECD.339-Fc | FGFR1-ECD.339-Fc (15 mg/kg, i.p., 3x/wk × 4 wks) | | |
| 10 | 5-Fu/LV | 5-FU (10 mg/kg, i.p., q.d. × 5 days) | LV (10 mg/kg, i.p., q.d. × 5 days) | |
| | FGFR1-ECD.339-Fc + 5-Fu/LV (10 mg/kg) | FGFR1-ECD.339-Fc (15 mg/kg, i.p., 3x/wk × 4 wks) | 5-FU (10 mg/kg, i.p., q.d. × 5 days) | LV (10 mg/kg, i.p., q.d. × 5 days) |
| 10 | 5-Fu/LV | 5-FU (20 mg/kg, i.p., q.d. × 5 days) | LV (20 mg/kg, i.p., q.d. × 5 days) | |
| | FGFR1-ECD.339-Fc + 5-Fu/LV (20 mg/kg) | FGFR1-ECD.339-Fc (15 mg/kg, i.p., 3x/wk × 4 wks) | 5-FU (20 mg/kg, i.p., q.d. × 5 days) | LV (20 mg/kg, i.p., q.d. × 5 days) |
| 10 | 5-Fu/LV | 5-FU (30 mg/kg, i.p., q.d. × 5 days) | LV (30 mg/kg, i.p., q.d. × 5 days) | |
| | FGFR1-ECD.339-Fc + 5-Fu/LV (30 mg/kg) | FGFR1-ECD.339-Fc (15 mg/kg, i.p., 3x/wk × 4 wks) | 5-FU (30 mg/kg, i.p., q.d. × 5 days) | LV (30 mg/kg, i.p., q.d. × 5 days) |
| 10 | Bevacizumab | Bev (1 mg/kg, i.p., 2x/wk × 4 wks) | — | |
| 10 | Bevacizumab + 5-Fu/LV | Bev (1 mg/kg, i.p., 2x/wk × 4 wks) | 5-Fu/LV (10 mg/kg each, i.p., q.d. × 5 days) | — |
| 10 | FGFR1-ECD.339-Fc | FGFR1-ECD.339-Fc (15 mg/kg, i.p., 3x/wk × 4 wks) | | |
| 10 | FGFR1-ECD.339-Fc + Bevacizumab | FGFR1-ECD.339-Fc (15 mg/kg, i.p., 3x/wk × 4 wks) | Bev (1 mg/kg, i.p., 2x/wk × 4 wks) | — |
| 10 | FGFR1-ECD.339-Fc + Bevacizumab + 5-Fu/LV | FGFR1-ECD.339-Fc (15 mg/kg, i.p., 3x/wk × 4 wks) | Bev (1 mg/kg, i.p., 2x/wk × 4 wks) | 5-Fu/LV (10 mg/kg each, i.p., q.d. × 5 days) |

When the average tumor volume in a group was near 600 mm$^3$, the mice in that group were euthanized by isoflurane inhalation and cervical dislocation. The mean tumor volume throughout the study for each set of mice is shown in FIG. 11. At 20 mg/kg 5-FU/leucovorin and 30 mg/kg 5-FU/leucovorin, the mice lost about 3 grams and about 4 grams of body weight, respectively (about 14% and 19%, respectively). (Data not shown.) No weight loss in the mice was observed in any of the remaining groups. (Data not shown.)

Figure 11A:
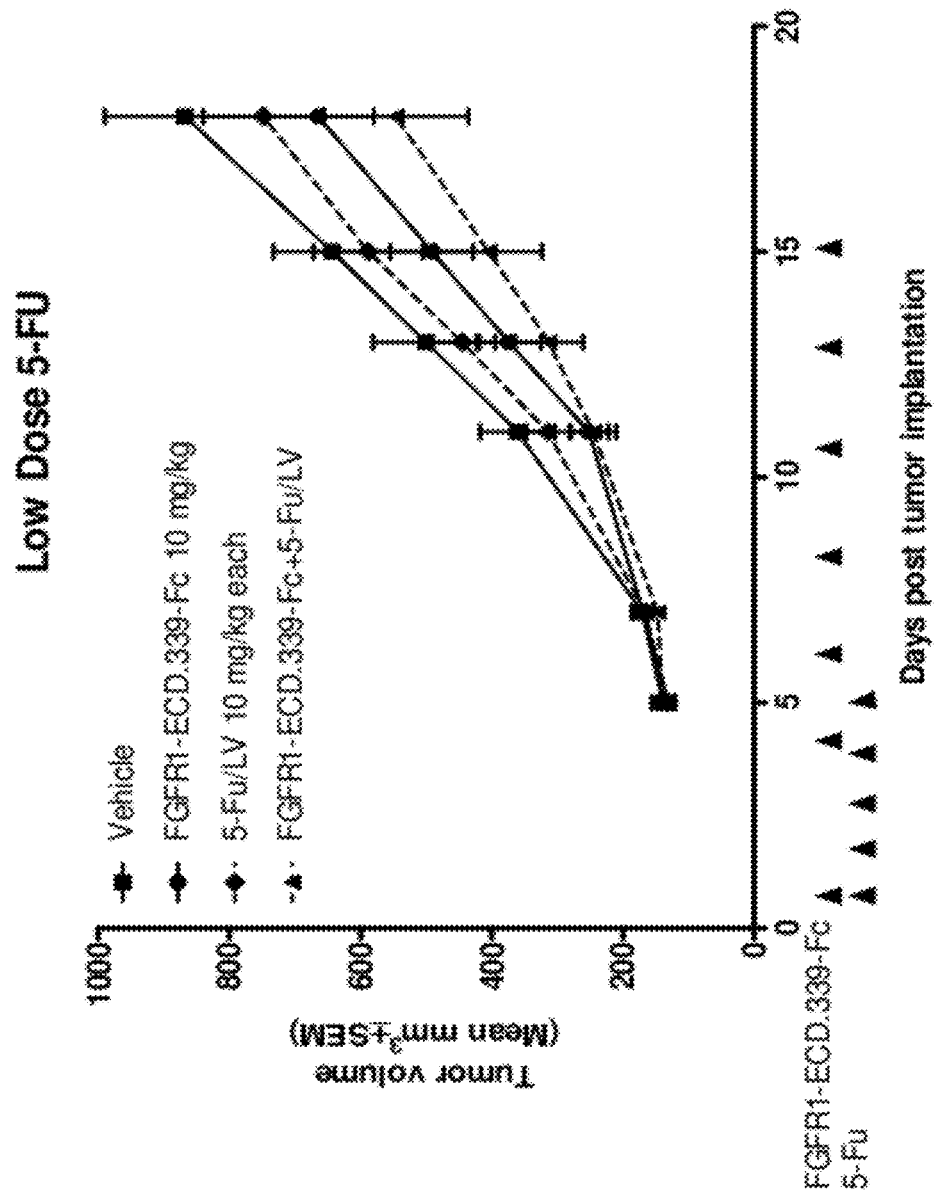
FIG. 11 shows the mean tumor volume in mice administered FGFR1-ECD.339-Fc alone, the combination of 5-FU (10 mg/kg) and leucovorin (10 mg/kg), and the combination of FGFR1-ECD.339-Fc, 5-FU (10 mg/kg), and leucovorin (10 mg/kg) (A); FGFR1-ECD.339-Fc alone, the combination of 5-FU (20 mg/kg) and leucovorin (20 mg/kg), and the combination of FGFR1-ECD.339-Fc, 5-FU (20 mg/kg), and leucovorin (20 mg/kg) (B); FGFR1-ECD.339-Fc alone, the combination of 5-FU (30 mg/kg) and leucovorin (30 mg/kg), and the combination of FGFR1-ECD.339-Fc, 5-FU (30 mg/kg), and leucovorin (30 mg/kg) (C); FGFR1-ECD.339-Fc alone, bevacizumab alone, and the combination of FGFR1-ECD.339-Fc and bevacizumab (D); and FGFR1-ECD.339-Fc alone, the combination of bevacizumab, 5-FU, and leucovorin, and the combination of FGFR1-ECD.339-Fc, bevacizumab, 5-FU, and leucovorin (E), as described in Example 4A.
Figure 11B:
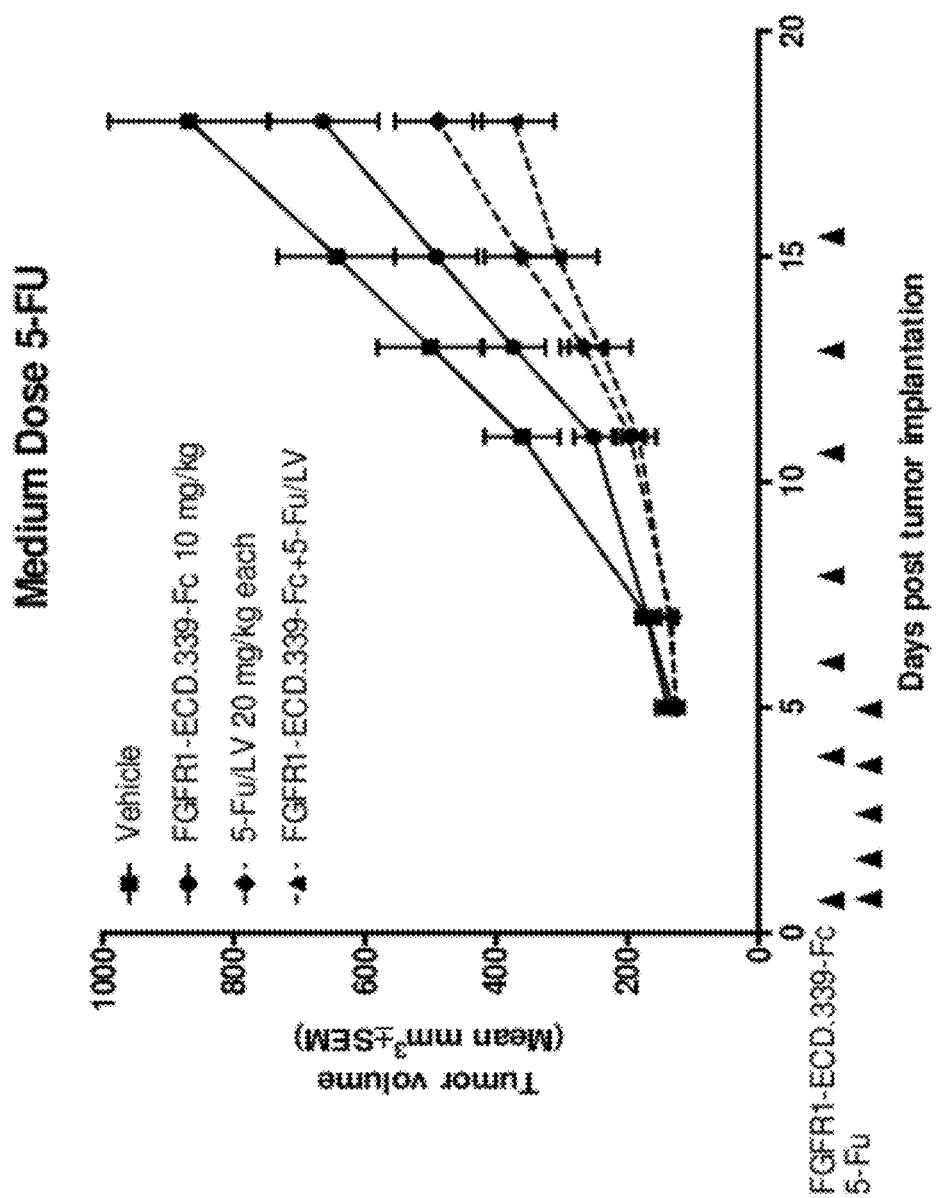
Figure 11C:
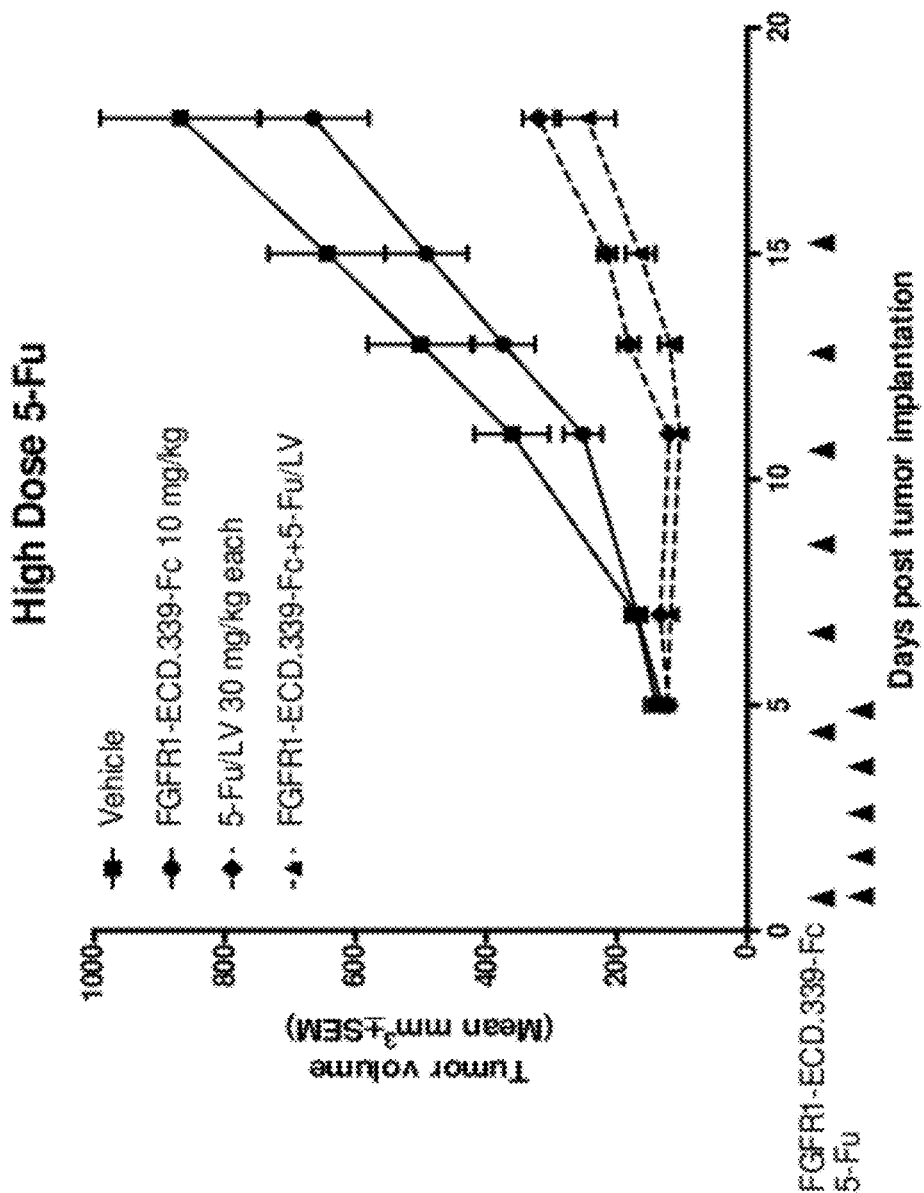
Figure 11D:
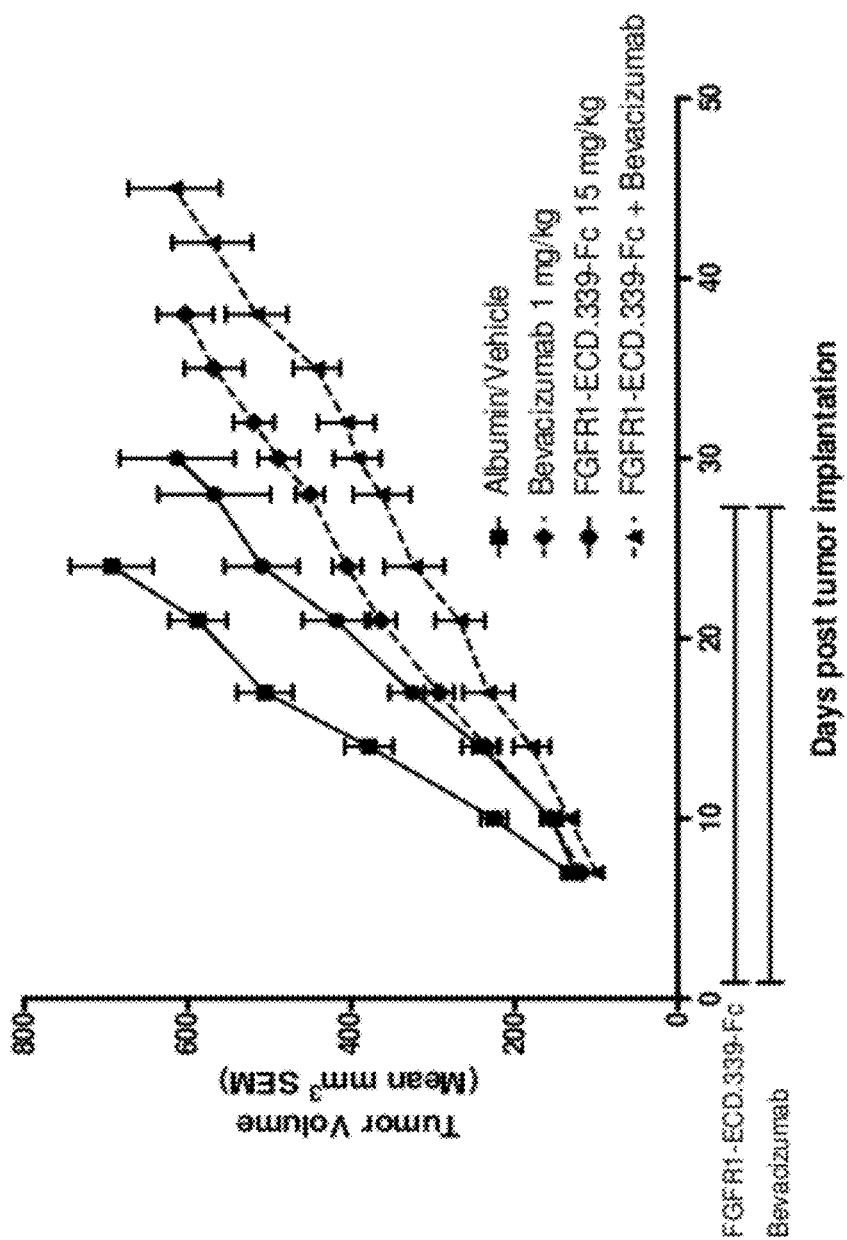
Figure 11E:
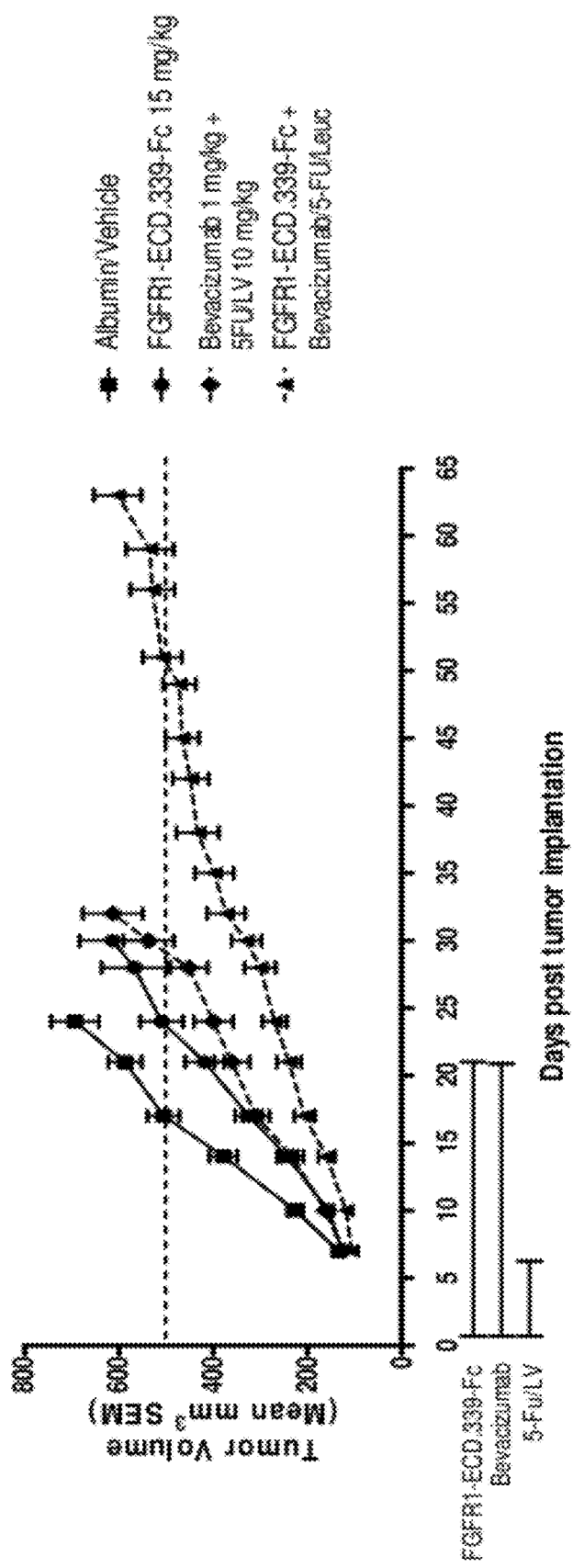

The order of effectiveness of the various treatments was evaluated two ways: 1) the average tumor volume in each group on a single time point (day); and 2) time for the average tumor volume in each group to reach 500 mm$^3$ (see the dotted line in FIG. 11E).

TABLE 16

Tumor volume analysis on day 24

| | Mean Tumor volume mm$^3$(±SD) | Tumor growth inhibition (%) | p Value compare to control (Tukey's test) |
|---|---|---|---|
| Albumin + vehicle | 693 (±159) | — | — |
| FGFR1-ECD.339-Fc | 509 (±144) | 26 | <0.05 |
| 5-FU/LV | 511 (±196) | 26 | >0.05 |
| Bevacizumab | 405 (±56) | 41 | <0.001 |

TABLE 16-continued

Tumor volume analysis on day 24

| | Mean Tumor volume mm$^3$(±SD) | Tumor growth inhibition (%) | p Value compare to control (Tukey's test) |
|---|---|---|---|
| Bevacizumab + 5-Fu/LV | 399 (±131) | 42 | <0.001 |
| FGFR1-ECD.339-Fc + Bevacizumab | 322 (±116) | 53 | <0.001 |
| FGFR1-ECD.339-Fc + Bevacizumab + 5-Fu/LV | 269 (±83) | 61 | <0.001 |

In order to determine whether administration of FGFR1-ECD.339-Fc and 5-FU/leucovorin at various concentrations; FGFR1-ECD.339-Fc and bevacizumab; or FGFR1-ECD.339-Fc, bevacizumab, and 5-Fu/leucovorin resulted in additive, synergistic, or antagonistic activity, fractional tumor volume was analyzed as described in Example 1. The results of that analysis are shown in Table 17.

TABLE 17

Analysis of fractional tumor volume$^a$

| | FGFR1-ECD.339-Fc | | Expected$^b$ | Observed | Expected/Observed$^c$ |
|---|---|---|---|---|---|
| | | 5-FU/LV (10 mg/kg) | | | |
| Day 16 | 0.76 | 0.86 | 0.67 | 0.62 | 1.08 |
| | | 5-FU/LV (20 mg/kg) | | | |
| Day 16 | 0.76 | 0.56 | 0.42 | 0.42 | 1.00 |
| | | 5-FU/LV (30 mg/kg) | | | |
| Day 16 | 0.76 | 0.36 | 0.27 | 0.28 | 0.96 |
| | | Bevacizumab | | | |
| Day 24 | 0.73 | 0.58 | 0.42 | 0.46 | 0.91 |
| | | Bevacizumab/ 5-Fu/LV | | | |
| Day 24 | 0.73 | 0.57 | 0.42 | 0.38 | 1.10 |

$^a$Fractional tumor volume (FTV) = (Mean tumor volume (TV) treated)/(Mean TV control)
$^b$Expected = (FTV drug 1) × (FTV drug 2)
$^c$Ratio of expected over observed, >2 = synergistic; ~1 = additive; <0.5 = antagonistic.

Those results show that administration of FGFR1-ECD.339-Fc and 5-FU/leucovorin at various concentrations; FGFR1-ECD.339-Fc and bevacizumab; or FGFR1-ECD.339-Fc, bevacizumab, and 5-Fu/leucovorin, resulted in additive inhibition of tumor growth.

B. FGFR1-ECD.339-Fc, 5-FU, Leucovorin, and Oxaliplatin

The combination of FGFR1-ECD.339-Fc, 5-FU, leucovorin, and oxaliplatin was tested in the Colo205 human colon cancer xenograft model, described above. FGFR1-ECD.339-Fc was formulated in PBS at 3 mg/ml (for administration at 15 mg/kg). 5-FU was purchased from Sigma-Aldrich (St. Louis, Mo.; Cat. No. F6627) and was initially dissolved in dimethyl sulfoxide (DMSO, Sigma-Aldrich, St. Louis, Mo.; Cat. No. D8418-50) at the concentration of 50 mg/ml as a stock solution. The stock solution was further diluted in 0.9% Sodium Chloride Injection USP to 2 mg/ml (for 10 mg/kg dosing). Leucovorin was also purchased from Sigma-Aldrich (Cat. No. F8259) and was formulated in 0.9% Sodium Chloride Injection USP at 2 mg/ml (for 10 mg/kg dosing). Oxaliplatin was obtained from LC laboratories (Woburn, Mass. 01801; Catalog #0-7111) and was formulated in 5% Dextrose Injection (Baxter, Deerfield, Ill. 60015; Catalog #2B0082) at 1 mg/mL, 2 mg/mL, and 3 mg/ml for administration at 5 mg/kg (100 µg/100 µL per mouse), 10 mg/kg (200 µg/100 µL per mouse), and 15 mg/kg (300 µg/100 µl per mouse).

FGFR1-ECD.339-Fc was administered intraperitoneally (i.p.) at 15 mg/kg twice per week starting on day 1 for four weeks. 5-FU and leucovorin were each administered i.p. at 10 mg/kg daily for five days. Oxaliplatin was administered i.p. at 5 mg/kg, 10 mg/kg, or 15 mg/kg in one dose on day 1.

Mice were euthanized on day 28 by isoflurane inhalation and cervical dislocation.

Figure 12A:
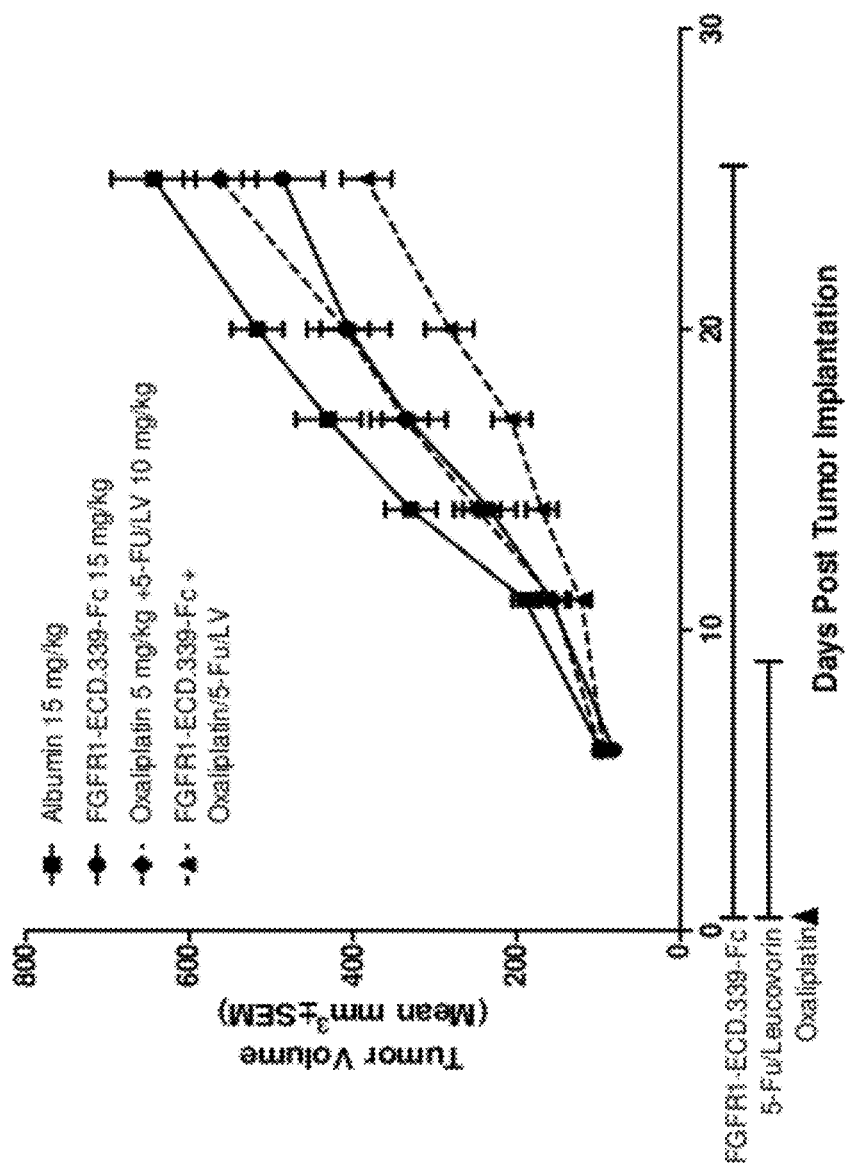
FIG. 12 shows the mean tumor volume in mice administered FGFR1-ECD.339-Fc alone, oxaliplatin plus 5-FU and leucovorin (LV) alone, and the combination of FGFR1-ECD.339-Fc and oxaliplatin plus 5-FU/LV, at different dosages of oxaliplatin, 5 mg/kg (A), 10 mg/kg (B), and 15 mg/kg (C), as described in Example 4B.
Figure 12B:
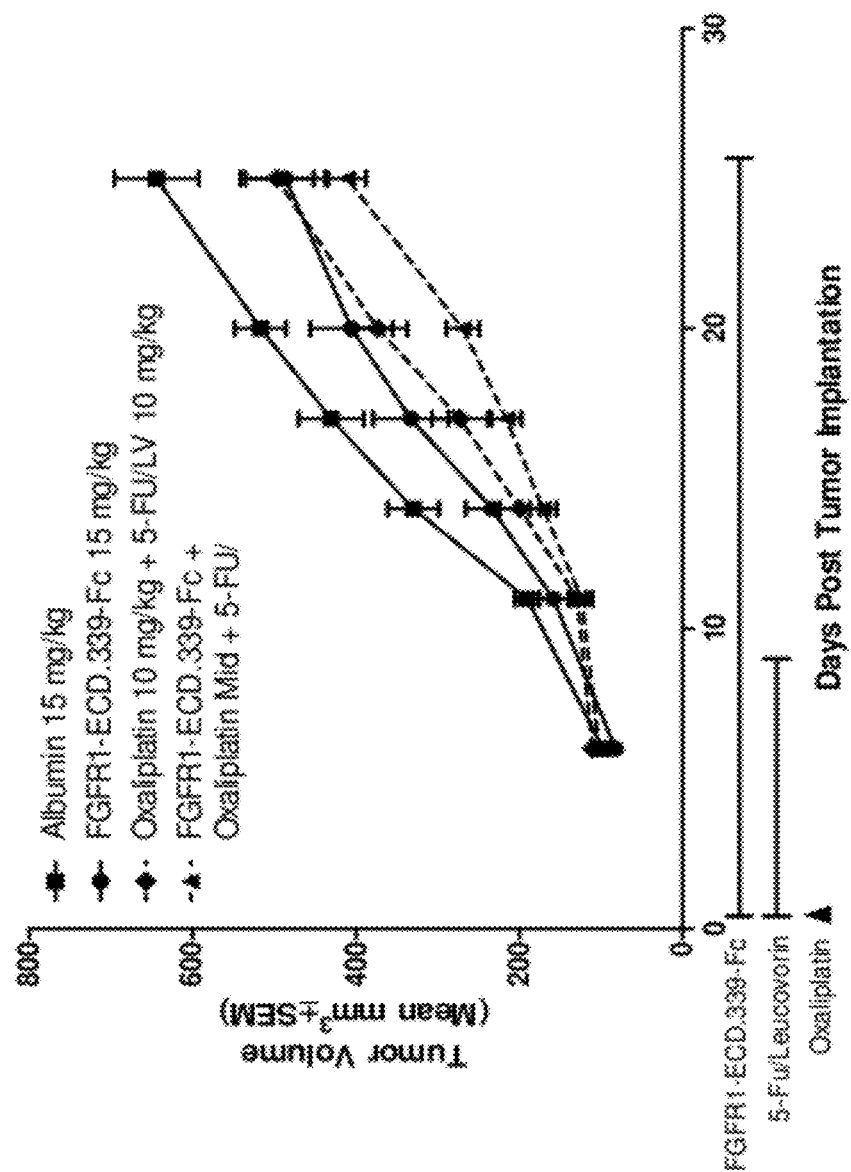
Figure 12C:
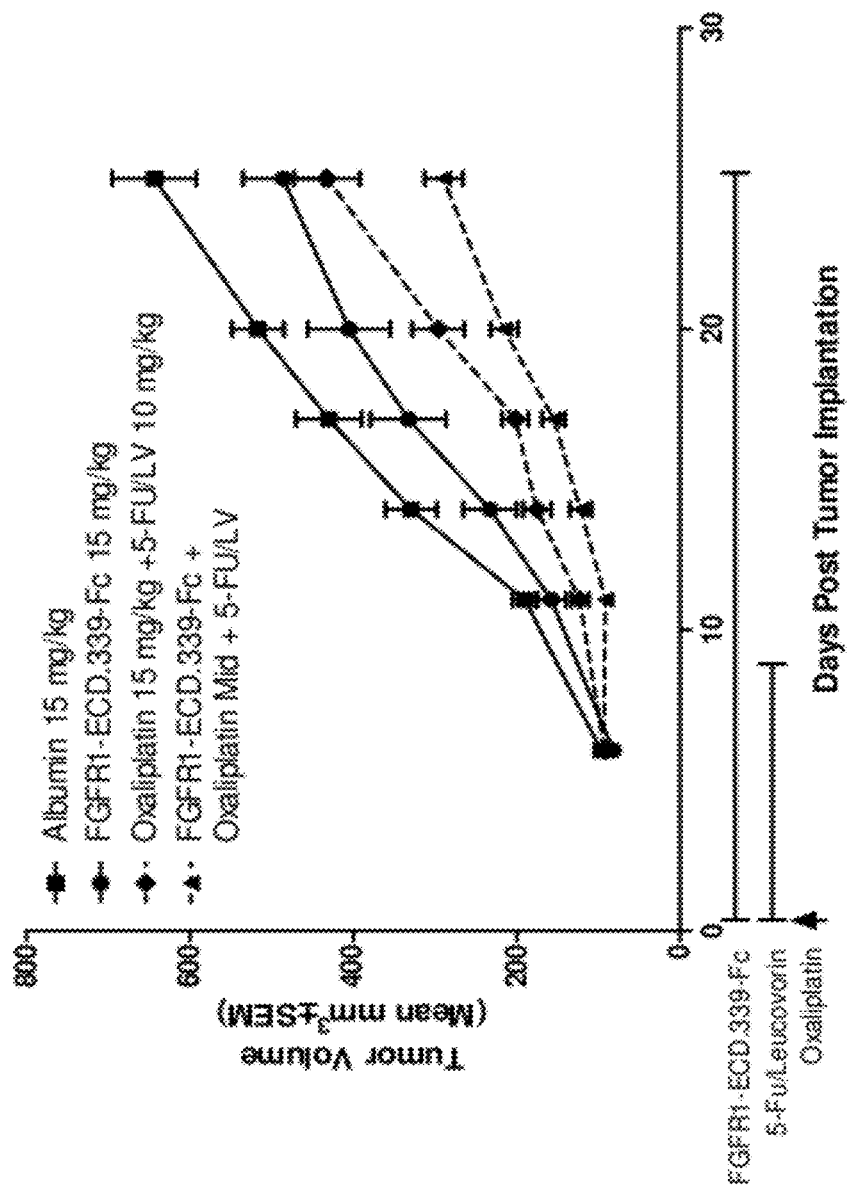

The mean tumor volume throughout the study for each set of mice is shown in FIG. 12. In that experiment, the combination of FGFR1-ECD.339-Fc, 5-FU, leucovorin, and oxaliplatin inhibited tumor growth more than FGFR1-ECD.339-Fc alone or the combination 5-FU, leucovorin, and oxaliplatin. Minimal weight loss in the mice was observed at 5 mg/kg oxaliplatin (0.78 grams, or 4% body weight); moderate weight loss was observed at 10 mg/kg (2.6 grams, or 13% body weight); and more severe weight loss was observed at 15 mg/kg oxaliplatin twice per week (3.7 grams, or 19% body weight). (Data not shown.)

In order to determine whether the combination of FGFR1-ECD.339-Fc, 5-FU, leucovorin, and oxaliplatin resulted in additive, synergistic, or antagonistic activity, fractional tumor volume on day 17 was analyzed as described in Example 1. The results of that analysis are shown in Table 18.

TABLE 18

Analysis of fractional tumor volume$^a$ on day 17

| Oxaliplatin dose | FGFR1-ECD.339-Fc | Oxaliplatin/ 5-FU/LV | Expected$^b$ | Observed | Expected/Observed$^c$ |
|---|---|---|---|---|---|
| 5 mg/kg | 0.77 | 0.78 | 0.60 | 0.47 | 1.27 |
| 10 mg/kg | 0.77 | 0.63 | 0.48 | 0.5 | 0.96 |
| 15 mg/kg twice per week | 0.77 | 0.46 | 0.35 | 0.36 | 0.97 |

$^a$Fractional tumor volume (FTV) = (Mean tumor volume (TV) treated)/(Mean TV control)
$^b$Expected = (FTV drug 1) × (FTV drug 2)
$^c$Ratio of expected over observed, >2 = synergistic; ~1 = additive; <0.5 = antagonistic.

Those results show that administration of FGFR1-ECD.339-Fc, 5-FU, leucovorin, and oxaliplatin resulted in additive inhibition of tumor growth at each dosage of oxaliplatin tested in that experiment.

Example 5

Administration of FGFR1-ECD.339-Fc, Doxorubicin, and Paclitaxel in the JIMT-1 Breast Cancer Xenograft Model Six week old female SCID mice were purchased from Charles River Laboratories (Wilmington, Mass.) and were acclimated for 1 week before the start of the study. Human breast cancer cell line JIMT-1 was used as the tumor model and was purchased from Deutsche Sammlung von Mikroorganismen and Zellkulturen GmbH (DMSZ, Braunschweig, Germany; Cat. No. ACC 589). The cells were cultured for ten passages in DMEM+10% FBS, 1% L-glutamine, and 1% penicillin/streptomycin at 37° C. in a humidified atmosphere with 5% CO$_2$. When the cultured cells reached 85-90% confluence, cells were harvested and resuspended in cold Ca$^{2+}$ and Mg$^{2+}$ free phosphate buffered saline (PBS) containing 50% Matrigel at 5×10$^7$ cells per milliliter. The cells were implanted subcutaneously over the right flank of the mice at 5×10$^6$ cells/100 µl/mouse. One day after tumor implantation, mice were randomized according to body weight at 10 mice per group.

FGFR1-ECD.339-Fc was formulated in 0.9% Saline for Injection USP at 3 mg/ml and administered intraperitoneally (i.p.) at 15 mg/kg (300 µg/100 µl/mouse) twice per week for five weeks beginning on day 7. Doxorubicin was obtained from Sigma-Aldrich (St. Luis, Mo.; Catalog #44583) and was formulated in 0.9% Saline for Injection USP at 0.05 mg/mL for administration at 0.5 mg/kg (10 µg/200 µL per mouse) once per week for five weeks, beginning on day 7. Paclitaxel was obtained from Bedford Laboratories (Bedford, Ohio; Cat. No. 1075029) and was formulated in a solution of 50.3% Cremophor® and 49.7% dehydrated alcohol. The stock solution was diluted in 5% dextrose/0.9% Saline for Injection USP to a final concentration of 3 mg/mL paclitaxel in 16.8% Cremophor®, 16.6% dehydrated alcohol, 3.3% dextrose, 0.6% Saline for Injection USP. Paclitaxel was administered at 30 mg/kg (60 µg/200 µL per mouse) twice per week for five weeks beginning on day 7.

The tumor volume and body weight of the mice were monitored twice a week throughout the study. The tumor volume was measured and calculated using the method and formula described in Example 1.

Mice were euthanized on day 42 by isoflurane inhalation and cervical dislocation.

Figure 13:
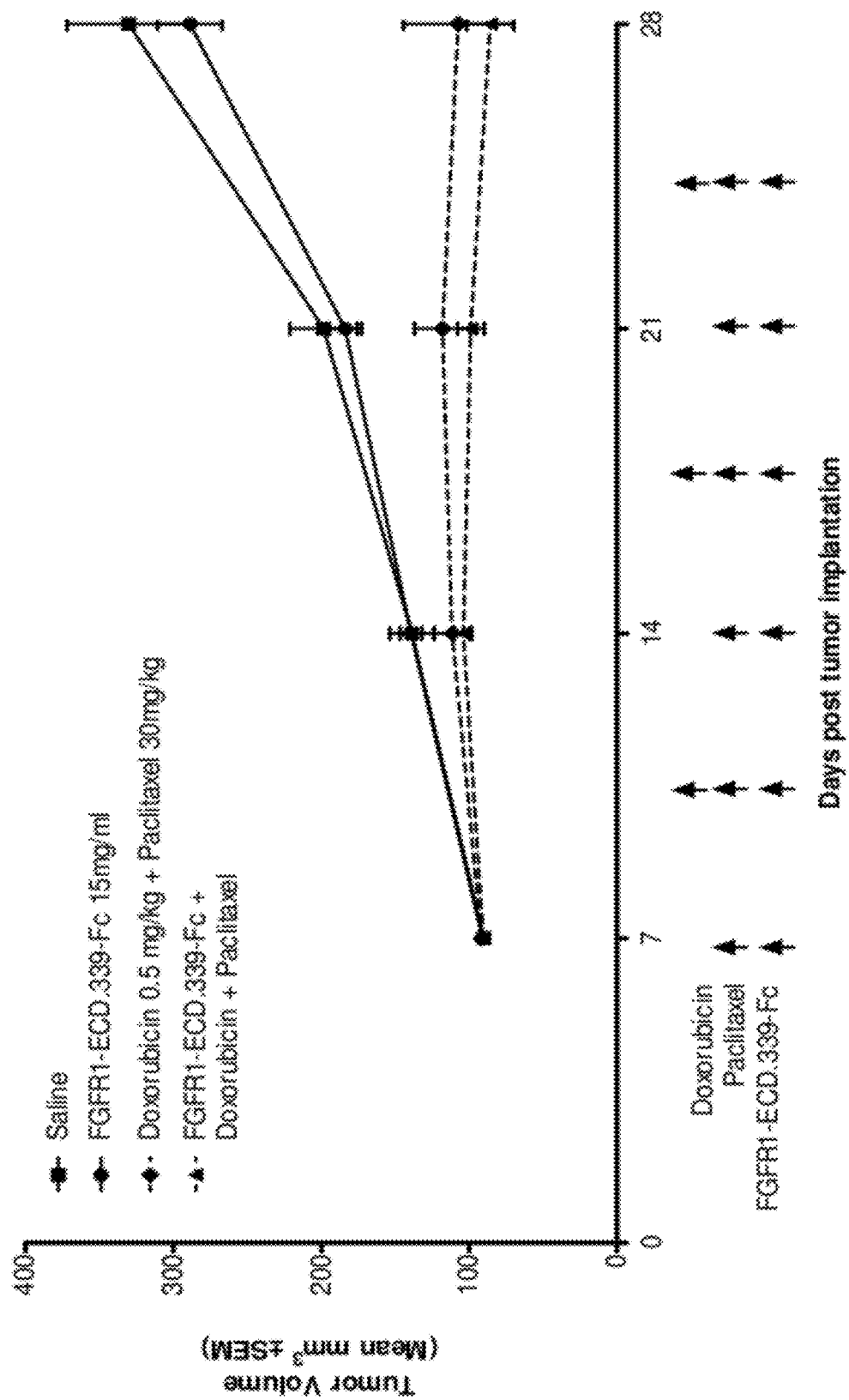
FIG. 13 shows the mean tumor volume in mice administered FGFR1-ECD.339-Fc alone, the combination of doxorubicin and paclitaxel, and the combination of FGFR1-ECD.339-Fc, doxorubicin, and paclitaxel, as described in Example 5.
Figure 14:
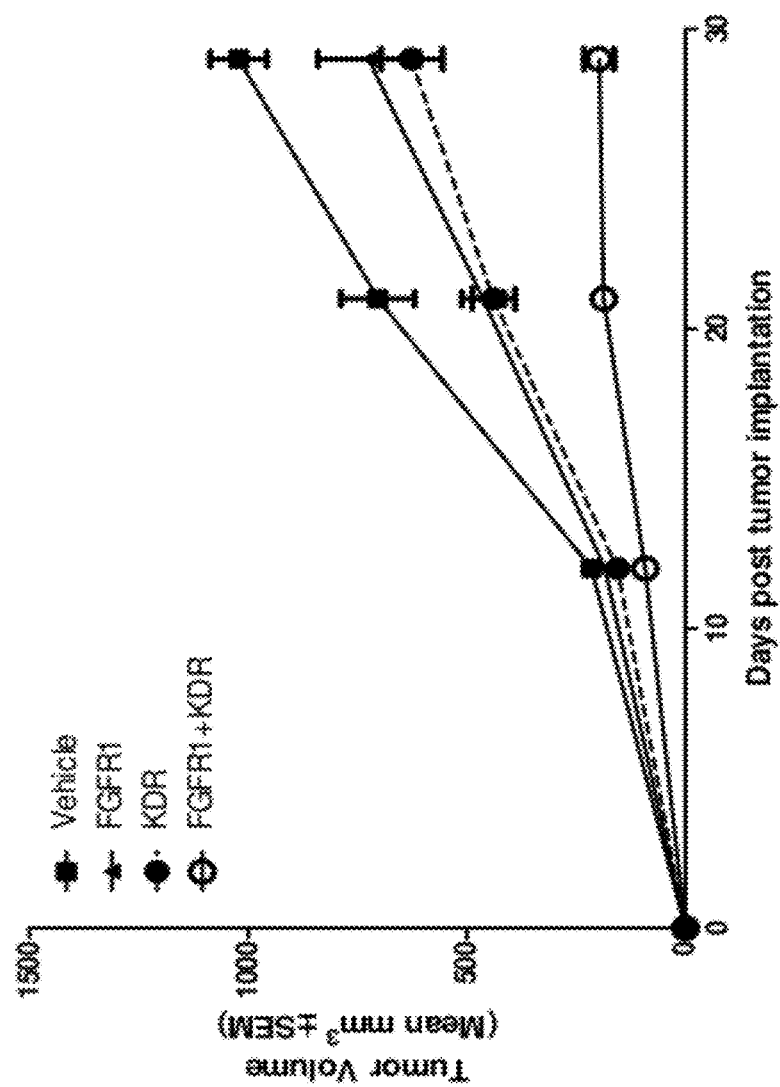
FIG. 14 shows the mean tumor volume in mice administered FGFR1-ECD.339-Fc alone, a Kinase Insert Domain Receptor (KDR)-ECD fusion molecule alone, and the combination of FGFR1-ECD.339-Fc and the KDR-ECD fusion molecule, as described in Example 6.

The mean tumor volume throughout the study for each set of mice is shown in FIG. 13. In that experiment, the combination of FGFR1-ECD.339-Fc, doxorubicin, and paclitaxel inhibited tumor growth more than FGFR1-ECD.339-Fc alone or the combination of doxorubicin and paclitaxel without FGFR1-ECD.339-Fc. No weight loss was observed over the course of the study. (Data not shown.)

Fractional tumor volume analysis was used to assess the degree of enhanced (additive or synergistic) or decreased (antagonistic) tumor growth inhibition by the combination of FGFR1-ECD.339-Fc, doxorubicin, and paclitaxel. The results of that analysis are shown in Table 19.

TABLE 19

Analysis of fractional tumor volume[a] on day 21

|  | FGFR1-ECD.339-Fc | Doxorubicin and paclitaxel | Expected[b] | Observed | Expected/Observed[c] |
|---|---|---|---|---|---|
| Day 21 | 0.93 | 0.59 | 0.55 | 0.50 | 1.10 |

[a]Fractional tumor volume (FTV) = (Mean tumor volume (TV) treated)/(Mean TV control)
[b]Expected = (FTV drug 1) × (FTV drug 2)
[c]Ratio of expected over observed, >2 = synergistic; ~1 = additive; <0.5 = antagonistic.

Those results demonstrate that the combination of FGFR1-ECD.339-Fc, doxorubicin, and paclitaxel resulted in additive inhibition of tumor growth in that experiment.

Example 6

Treatment with FGFR1-ECD.339-Fc and KDR ECD-Fc in Mice Having H520 Lung Xenograft Tumor Cells Showed Tumor Inhibition SCID CB17 mice at 8 weeks of age were administered either vehicle, kinase insert domain receptor (KDR) cDNA (Five Prime Therapeutics, South San Francisco, Calif.) (which expresses a protein that acts as a VEGF antagonist and VEGF trap), FGFR1 cDNA (Five Prime Therapeutics, South San Francisco, Calif.), or a combination of KDR and FGFR1, by hydrodynamic tail vein transfection (TVT), substantially as described in Chen et al., *Human Gene Therapy* 16(1): 126-131 (2005), and then inoculated 4 days later with 5×10$^6$ H520 lung xenograft tumor cells s.c. on the flank, with the cells in a 1:1 mixture of Matrigel in 100 µl total volume. KDR and FGFR1 cDNA constructs each contain their respective extracellular domain fused to an IgG1 Fc domain. Tumor volume measurements were made at approximately 10 day intervals. On day 29, the tumor volume was reduced in groups treated with single agents relative to vehicle (Mann Whitney test P<0.05). On day 29, the tumor volume was reduced in the combination group relative to groups treated with single agents (Mann Whitney test P<0.001).

Example 7

Administration of FGFR1-ECD.339-Fc and Cisplatin/Etoposide in the DMS 53 Small Cell Lung Cancer (SCLC) Xenograft Model Six week old female SCID mice were purchased from Charles River Laboratories (Wilmington, Mass.) and were acclimated for 1 week before the start of the study. Human small cell lung cancer (SCLC) cell line DMS 53 was used as the tumor model and was purchased from ATCC (Manassas, Va.; Cat. No. CRL-2062). The cells were cultured for three passages in Waymouth's MB 752/1 medium+10% FBS+2 mM L-glutamine at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at 5×10$^7$ cells per milliliter. The cells were implanted subcutaneously over the right flank of the mice at 5×10$^6$ cells/100 µl/mouse. After tumors reached a size of 100-125 mm$^3$, mice were sorted and randomized so each group (n=10) has the approximately the same average tumor volume, and treatment initiated according to Table 20 below.

FGFR1-ECD.339-Fc was formulated in PBS at 3 mg/ml and administered intraperitoneally (i.p.) at 15 mg/kg (300 µg/100 µl/mouse) twice a week for four weeks. Cisplatin was purchased from Amatheon, Inc., Miami, Fla. (Cat No. 5539-0112-50) pre-formulated at concentration of 1 mg/ml. 0.45 ml of cisplating stock solution (1 mg/ml) was added to 1.05 ml of 5% dextrose solution, for a 1.5 ml working solution with a concentration of 0.3 mg/ml. Each mouse received 100 µl of working solution (0.3 mg/ml) to provide a dose of 3 mg/kg every 7 or 21 days depending on group. Etoposide was purchased from Amatheon, Inc (Cat. No. 5539-0291-01) pre-formulated at concentration of 20 mg/ml. 0.140 ml of stock solution (20 mg/ml) was added to 3.36 ml of 5% dextrose solution, for a 3.5 ml working solution with a concentration of 0.8 mg/ml. Each mouse received 50 µl of working solution (0.8 mg/ml) to provide a dose of 4 mg/kg for 3 days in a row. Etoposide dosing was repeated every 7 or 21 days depending on group. In combination groups, FGFR1-ECD.339-Fc and cisplatin/etoposide was administered concurrently. Human albumin was purchased from Grifols USA (Los Angeles, Calif.; Cat. No. NDC 61953-0002-1), diluted to a working stock (3 mg/ml) with 0.9% sodium chloride, and was used as negative control at 300 µg/100 µl/mouse (15 mg/kg). The dosing schedule for each set of mice is shown in Table 20.

TABLE 20

| Group | Drugs | Cisplatin (mg/kg, schedule) | Etoposide (mg/kg, schedule) | FGFR1-ECD.339-Fc (mg/kg, schedule) | Route |
|---|---|---|---|---|---|
| 1 | Albumin 15 mg/kg | 0 | 0 | 0 | IP |
| 2 | FGFR1-ECD.339-Fc | 0 | 0 | 15, 2x/week | IP |
| 3 | Cisplatin/Etoposide | 3, once every 21 days | 4, qd × 3 every 21 days | 0 | IP |

TABLE 20-continued

| Group | Drugs | Cisplatin (mg/kg, schedule) | Etoposide (mg/kg, schedule) | FGFR1-ECD.339-Fc (mg/kg, schedule) | Route |
|---|---|---|---|---|---|
| 4 | Cisplatin/Etoposide/FGFR1-ECD.339-Fc | 3, once every 21 days | 4, qd × 3 every 21 days | 15, 2x/week | IP |
| 5 | Cisplatin/Etoposide | 3, once every 7 days | 4, qd × 3 every 7 days | 0 | IP |
| 6 | Cisplatin/Etoposide/FGFR1-ECD.339-Fc | 3, once every 7 days | 4, qd × 3 every 7 days | 15, 2x/week | IP |

Example 8

Administration of FGFR1-ECD.339-Fc and Topotecan in the DMS 53 Small Cell Lung Cancer (SCLC) Xenograft Model Six week old female SCID mice were purchased from Charles River Laboratories (Wilmington, Mass.) and were acclimated for 1 week before the start of the study. Human small cell lung cancer (SCLC) cell line DMS 53 was used as the tumor model and was purchased from ATCC (Manassas, Va.; Cat. No. CRL-2062). The cells were cultured for three passages in Waymouth's MB 752/1 medium+10% FBS+2 mM L-glutamine at 37° C. in a humidified atmosphere with 5% $CO_2$. When the cultured cells reached 85-90% confluence, cells were harvested and resuspended in cold $Ca^{2+}$ and $Mg^{2+}$ free phosphate buffered saline (PBS) containing 50% Matrigel at $5×10^7$ cells per milliliter. The cells were implanted subcutaneously over the right flank of the mice at $5×10^6$ cells/100 μl/mouse. After tumors reached a size of 100-125 $mm^3$, mice were sorted and randomized so each group (n=10) has the approximately the same average tumor volume, and treatment initiated according to Table 21 below.

FGFR1-ECD.339-Fc was formulated in PBS at 3 mg/ml and administered intraperitoneally (i.p.) at 15 mg/kg (300 μg/100 μl/mouse) twice a week for four weeks. Topotecan powder was purchased from Sigma-Aldrich, Inc. (Cat No. T2705-50MG) and a 5 mg/ml stock solution made in a 5% dextrose solution. Dilutions are also made with 5% dextrose solution. 0.6 ml of stock solution (5 mg/ml) was added to 5.4 ml of 5% dextrose solution, for a 6 ml working solution with a concentration of 0.5 mg/ml. Each mouse received 100 μl of working solution (0.5 mg/ml) to give a dose of 2.5 mg/kg. Topotecan dosing was repeated every 7 or 21 days depending on group. In combination groups, FGFR1-ECD.339-Fc and topotecan was administered concurrently. Human albumin was purchased from Grifols USA (Los Angeles, Calif.; Cat. No. NDC 61953-0002-1), diluted to a working stock (3 mg/ml) with 0.9% sodium chloride, and was used as negative control at 300 μg/100 μl/mouse (15 mg/kg). The dosing schedule for each set of mice is shown in Table 21.

TABLE 21

| Group | Drugs | Topotecan (mg/kg, schedule) | FGFR1-ECD.339-Fc (mg/kg, schedule) | Route |
|---|---|---|---|---|
| 1 | Albumin 15 mg/kg | 0 | 0 | IP |
| 2 | FGFR1-ECD.339-Fc | 0 | 15, 2x/week | IP |
| 3 | Topotecan | 2.5, qd × 5 every 21 days | 0 | IP |
| 4 | Topotecan/FGFR1-ECD.339-Fc | 2.5, qd × 5 every 21 days | 15, 2x/week | IP |
| 5 | Topotecan | 2.5, qd × 5 every 7 days | 0 | IP |
| 6 | Topotecan/FGFR1-ECD.339-Fc | 2.5, qd × 5 every 7 days | 15, 2x/week | IP |

Table of Sequences

Table 22 lists certain sequences discussed herein. FGFR1 sequences are shown without the signal peptide, unless otherwise indicated.

TABLE 22

Sequences and Descriptions

| SEQ ID NO | Description | Sequence |
|---|---|---|
| 1 | Full-length human FGFR1 ECD (with signal peptide); SP-hFGFR1-ECD.353 | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |
| 2 | Full-length human FGFR1 ECD (without signal peptide); hFGFR1-ECD.353 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |

TABLE 22-continued

Sequences and Descriptions

| SEQ ID NO | Description | Sequence |
|---|---|---|
| 3 | SP-hFGFR1-ECD.339 | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL |
| 4 | hFGFR1-ECD.339 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL |
| 5 | SP-hFGFR1-ECD.339-Fc | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 6 | hFGFR1-ECD.339-Fc | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 7 | hFGFR1 signal peptide | MWSWKCLLFWAVLVTATLCTA |
| 8 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 9 | Exemplary Fc #1 | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 10 | Exemplary Fc #2 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |

The invention claimed is:

1. A method of treating cancer in a subject comprising administering to the subject an effective amount of a fibroblast growth factor receptor 1 (FGFR1) extracellular domain (ECD) fusion molecule and at least one additional therapeutic agent selected from docetaxel, vincristine, and topotecan, wherein the FGFR1 ECD fusion molecule comprises an FGFR1 ECD comprising an amino acid sequence selected from SEQ ID NOs: 1 to 4 and a fusion partner, and wherein administration of the FGFR1 ECD fusion molecule and the at least one additional therapeutic agent results in synergistic inhibition of tumor growth in a mouse xenograft model of the cancer, wherein the cancer is small cell lung cancer and the mouse xenograft model comprises DMS 53 cells.

2. A method of treating cancer in a subject comprising administering to the subject an effective amount of a fibroblast growth factor receptor 1 (FGFR1) extracellular domain (ECD) fusion molecule and at least one additional therapeutic agent selected from docetaxel, vincristine, and topotecan, wherein the FGFR1 ECD fusion molecule comprises an FGFR1 ECD comprising an amino acid sequence selected from SEQ ID NOs: 1 to 4 and a fusion partner, and wherein administration of the FGFR1 ECD fusion molecule and the at least one additional therapeutic agent results in synergistic inhibition of tumor growth in a mouse xenograft model of the cancer, wherein the cancer is non-small cell lung cancer and the mouse xenograft model comprises H1703 cells.

3. The method of claim 1, wherein the method comprises administering a FGFR1 ECD fusion molecule and topotecan.

4. The method of claim 3, wherein the FGFR1 ECD fusion molecule comprises a sequence selected from SEQ ID NO: 5 and SEQ ID NO: 6.

5. The method of claim 2, wherein the method comprises administering a FGFR1 ECD fusion molecule and docetaxel.

6. The method of claim 5, wherein the FGFR1 ECD fusion molecule comprises a sequence selected from SEQ ID NO: 5 and SEQ ID NO: 6.

* * * * *